(12) United States Patent
Clark et al.

(10) Patent No.: US 8,828,988 B2
(45) Date of Patent: Sep. 9, 2014

(54) 8-AZA TETRACYCLINE COMPOUNDS

(71) Applicants: Roger B. Clark, Lexington, MA (US); Minsheng He, Watertown, MA (US); Louis Plamondon, Montreal (CA); Xiao-Yi Xiao, Lexington, MA (US); Magnus P. Rönn, Melrose, MA (US)

(72) Inventors: Roger B. Clark, Lexington, MA (US); Minsheng He, Watertown, MA (US); Louis Plamondon, Montreal (CA); Xiao-Yi Xiao, Lexington, MA (US); Magnus P. Rönn, Melrose, MA (US)

(73) Assignee: Tetraphase Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 13/731,753

(22) Filed: Dec. 31, 2012

(65) Prior Publication Data

US 2013/0345178 A1    Dec. 26, 2013

Related U.S. Application Data

(63) Continuation of application No. 13/319,307, filed as application No. PCT/US2010/001348 on May 7, 2010, now Pat. No. 8,367,654.

(60) Provisional application No. 61/215,747, filed on May 8, 2009.

(51) Int. Cl.
    *A61K 31/397*    (2006.01)
    *A61K 31/497*    (2006.01)
    *A61K 31/435*    (2006.01)

(52) U.S. Cl.
    USPC .................. 514/210.21; 514/253.02; 514/284

(58) Field of Classification Search
    USPC ................................ 514/210.21, 253.02, 284
    See application file for complete search history.

(56) References Cited

U.S. PATENT DOCUMENTS

| 8,367,654 B2 | 2/2013 | Clark et al. |
| 2012/0108569 A1 | 5/2012 | Clark et al. |

FOREIGN PATENT DOCUMENTS

| WO | WO 99/37307 | 7/1999 |
| WO | WO 2005/112945 A3 | 12/2005 |
| WO | WO 2010/129055 A1 | 11/2010 |

OTHER PUBLICATIONS

Charest, M.G., et al., "A Convergent Enantioselective Route to Structurally Diverse 6-Deoxytetracycline Antibiotics", Science, 308: 395-398 (2005).
Huel, Christiane, et al., "Synthesis of 1-Functionalized-6-hydroxy-4-methyl and 6,11-Dihydroxy-4-methylnaphtho[2,3-g]isoquinoline-5,12-quinoes," *J Heterocyclic Chem.*, 28: 67-71 (1991).
Notification of Transmittal of International Search Report and the Written Opinion of the International Search Authority, or the Declaration, in International Application No. PCT/US2010/001348, Date of Mailing: Jul. 19, 2010.
Notification Concerning Transmittal of International Preliminary Report on Patentability for International Application No. PCT/US2010/001348, Date of Mailing: Nov. 17, 2011.
Notice of Allowance, U.S. Appl. No. 13/319,307, Date of Mailing: Sep. 19, 2012.

*Primary Examiner* — Samantha Shterengarts
(74) *Attorney, Agent, or Firm* — Hamilton, Brook, Smith & Reynolds, P.C.

(57) ABSTRACT

The present invention is directed to a compound represented by Structural Formula (I):

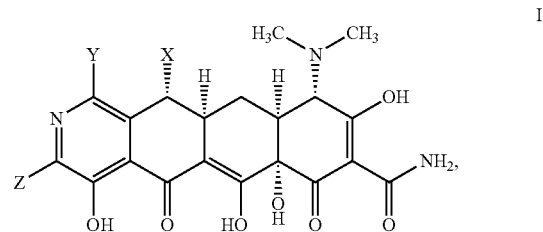

or a pharmaceutically acceptable salt thereof. The variables for Structural Formula I are defined herein. Also described is a pharmaceutical composition comprising the compound of Structural Formula I and its therapeutic use.

14 Claims, No Drawings

8-AZA TETRACYCLINE COMPOUNDS

RELATED APPLICATION

This application is a Continuation of U.S. application Ser. No. 13/319,307, filed Jan. 18, 2012, which is the U.S. National Stage of International Application No. PCT/US2010/001348, filed May 7, 2010, which designates the U.S., published in English, and claims the benefit of U.S. Provisional Application No. 61/215,747, filed May 8, 2009. The entire teachings of the above applications are incorporated herein by reference.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistance to these antibiotics, even among highly susceptible bacterial species. Therefore, there is need for new tetracycline analogs with improved antibacterial activities and efficacies against other tetracycline responsive diseases or disorders.

SUMMARY OF THE INVENTION

Compounds of Formula I are new tetracycline analogs with improved antibacterial activities and efficacies against other tetracycline responsive diseases or disorders:

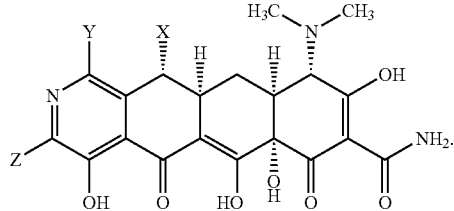

I

Pharmaceutically acceptable salts of the compound of Formula I are also included. A first embodiment of the invention includes values for the variables in Formula I are provided below:

X is selected from hydrogen, $C_1$-$C_6$ alkyl, phenyl, and $C_1$-$C_6$ alkoxy, wherein each $C_1$-$C_6$ alkyl and $C_1$-$C_6$ alkoxy represented by X is optionally substituted with halo, unsubstituted $C_1$-$C_6$ alkyl, halo($C_1$-$C_6$)alkyl, unsubstituted $C_1$-$C_6$ alkoxy or halo($C_1$-$C_6$)alkoxy;

Y is selected from hydrogen, fluoro, chloro, $C_1$-$C_6$ alkyl, $C_1$-$C_6$ alkoxy, ($C_0$-$C_6$) alkylene-N($R^1$)($R^2$) and phenyl, wherein
    each of $R^1$ and $R^2$ is independently selected from hydrogen, and $C_1$-$C_6$ alkyl;
Z is selected from hydrogen, halo, $C_1$-$C_6$ alkyl, phenyl, —N($R^3$)($R^4$), ($C_1$-$C_6$) alkylene-N($R^5$)($R^6$), wherein
    $R^3$ is selected from hydrogen, $C_1$-$C_6$ alkyl, ($C_1$-$C_6$) alkylene-phenyl, phenyl, ($C_1$-$C_6$) alkylene-($C_3$-$C_7$ cycloalkyl), ($C_1$-$C_6$) alkylene-O—($C_1$-$C_6$ alkyl), ($C_1$-$C_6$) alkylene-N($R^5$)($R^6$), —C(O)—($C_0$-$C_6$) alkylene-N($R^5$)($R^6$), and —C(O)—($C_1$-$C_6$ alkyl);
    $R^4$ is selected from hydrogen, $C_1$-$C_6$ alkyl; or $R^3$ and $R^4$ are taken together with the nitrogen atom to which they are bound to form a (4-7 membered) heterocyclic ring optionally containing one additional heteroatom selected from S, O or N;
$R^5$ is selected from hydrogen, $C_1$-$C_6$ alkyl and phenyl;
$R^6$ is selected from hydrogen and $C_1$-$C_6$ alkyl; or
$R^5$ and $R^6$ are taken together with the nitrogen atom to which they are bound to form a (4-7 membered) heterocyclic ring optionally containing one additional heteroatom selected from S, O or N,
wherein each ($C_1$-$C_6$) alkyl, ($C_1$-$C_6$) alkylene or a (4-7 membered) heterocyclic ring in the group represented by Z is optionally substituted with fluoro, —OH, or —CH$_3$; and
wherein each phenyl in the group represented by X, Y, Z, $R^3$ and $R^5$ is optionally substituted with halo, unsubstituted $C_1$-$C_6$ alkyl, halo($C_1$-$C_6$) alkyl, unsubstituted $C_1$-$C_6$ alkoxy, halo($C_1$-$C_6$)alkoxy, cyano or nitro.

In certain aspects of the first embodiment, $R^3$ is additionally selected from —C(O)H, —C(O)-phenyl, and —S(O)$_2$—$R^5$.

In a specific aspect of the first embodiment, Y and Z are not simultaneously hydrogen.

Another embodiment of the present invention is directed to a pharmaceutical composition comprising a pharmaceutically acceptable carrier or diluent and a compound disclosed herein or a pharmaceutically acceptable salt thereof. The pharmaceutical composition is used in therapy, such as treating an infection in a subject.

Another embodiment of the present invention is a method of treating an infection in a subject comprising administering to the subject an effective amount of a compound disclosed herein or a pharmaceutically acceptable salt thereof.

Another embodiment of the present invention is the use of a compound disclosed herein or a pharmaceutically acceptable salt thereof for the manufacture of a medicament for treating an infection in a subject.

Another embodiment of the present invention is the use of a compound disclosed herein or a pharmaceutically acceptable salt thereof for therapy, such as treating an infection in a subject.

DETAILED DESCRIPTION OF THE INVENTION

The present invention is directed to a compound represented by Structural Formula I or a pharmaceutically acceptable salt thereof. Values and alternative values for the variables in Structural Formula I are defined as the following:

X is hydrogen, $C_1$-$C_6$ alkyl, phenyl or $C_1$-$C_6$ alkoxy. Each $C_1$-$C_6$ alkyl or $C_1$-$C_6$ alkoxy in the group represented by X is optionally substituted with halo, unsubstituted $C_1$-$C_6$ alkyl, halo($C_1$-$C_6$)alkyl, unsubstituted $C_1$-$C_6$ alkoxy or halo($C_1$-$C_6$) alkoxy. X is hydrogen or $C_1$-$C_6$ alkyl. Alternatively, X is hydrogen.

Y is hydrogen, fluoro, chloro, $C_1$-$C_6$ alkyl, $C_1$-$C_6$ alkoxy, ($C_0$-$C_6$) alkylene-N($R^1$)($R^2$) or phenyl. Alternatively, Y is fluoro, chloro, $C_1$-$C_6$ alkyl, $C_1$-$C_6$ alkoxy, ($C_0$-$C_6$) alkylene-N($R^1$)($R^2$) or phenyl. Each $C_1$-$C_6$ alkyl, —($C_0$-$C_6$) alkylene or $C_1$-$C_6$ alkoxy in the group represented by Y is optionally substituted with halo, unsubstituted $C_1$-$C_6$ alkyl, halo($C_1$-$C_6$) alkyl, unsubstituted $C_1$-$C_6$ alkoxy or halo($C_1$-$C_6$)alkoxy. Y hydrogen, chloro, fluoro, —N(CH$_3$)(CH$_3$), —OCH$_3$, phenyl or ($C_1$-$C_6$)alkyl.

Z is hydrogen, halo, $C_1$-$C_6$ alkyl, phenyl, —N($R^3$)($R^4$) or ($C_1$-$C_6$) alkylene-N($R^5$)($R^6$). Alternatively, Z is hydrogen, $C_1$-$C_6$ alkyl, phenyl or N($R^3$)($R^4$). Alternatively, Z is hydrogen, —NH$_2$, —NH(CH$_2$)$_2$CH$_3$, —NH(CH$_2$)$_2$OCH$_3$, —NHCH$_2$CF$_3$ or —NHCH$_2$C(CH$_3$)$_2$CH$_2$N(CH$_3$)CH$_3$. In another alternative, Z is hydrogen.

Each R$^1$ and R$^2$ is independently hydrogen or C$_1$-C$_6$ alkyl.

R$^3$ is hydrogen, C$_1$-C$_6$ alkyl, —(C$_1$-C$_6$ alkylene)-phenyl, phenyl, —(C$_1$-C$_6$ alkylene)-(C$_3$-C$_7$ cycloalkyl), —(C$_1$-C$_6$ alkylene)-O—(C$_1$-C$_6$ alkyl), —(C$_1$-C$_6$ alkylene)-N(R$^5$)(R$^6$), —C(O)—(C$_0$-C$_6$ alkylene)-N(R$^5$)(R$^6$) or —C(O)—(C$_1$-C$_6$ alkyl). Alternatively, R$^3$ is additionally selected from —C(O)H, —C(O)-phenyl, and —S(O)$_2$—R$^5$.

R$^4$ is hydrogen or C$_1$-C$_6$ alkyl.

Alternatively, R$^3$ and R$^4$ are taken together with the nitrogen atom to which they are bound to form a (4-7 membered) heterocyclic ring optionally containing one additional heteroatom selected from S, O or N.

R$^5$ is hydrogen, C$_1$-C$_6$ alkyl or phenyl.

R$^6$ is selected from hydrogen and C$_1$-C$_6$ alkyl; or

Alternatively, R$^5$ and R$^6$ are taken together with the nitrogen atom to which they are bound to form a (4-7 membered) heterocyclic ring optionally containing one additional heteroatom selected from S, O or N.

Each (C$_1$-C$_6$) alkyl, (C$_1$-C$_6$) alkylene or a (4-7 membered) heterocyclic ring in the group represented by Z is optionally substituted with fluoro, —OH, or —CH$_3$.

Each phenyl in the group represented by X, Y, Z, R$^3$ and R$^5$ is optionally substituted with halo, unsubstituted C$_1$-C$_6$ alkyl, halo(C$_1$-C$_6$)alkyl, unsubstituted C$_1$-C$_6$ alkoxy, halo(C$_1$-C$_6$) alkoxy, cyano or nitro. Preferably, each phenyl in the group represented by X, Y, Z, R$^3$ and R$^5$ is optionally substituted with halo, unsubstituted C$_1$-C$_6$ alkyl, halo(C$_1$-C$_6$)alkyl, unsubstituted C$_1$-C$_6$ alkoxy or halo(C$_1$-C$_6$)alkoxy. More preferably, each phenyl in the group represented by X, Y, Z, R$^3$ and R$^5$ is optionally substituted with fluoro, —CF$_3$, —OCH$_3$ or —OCF$_3$.

A second embodiment is a compound of Structural Formula II, or a pharmaceutically acceptable salt thereof:

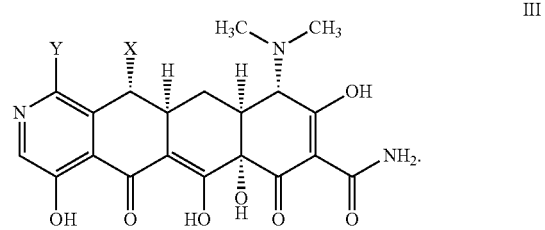

II

Values and alternative values for the variables in Structural Formula II are as defined for Structural Formula I above. Alternatively, for Structural Formulas I or II, Y is hydrogen, chloro, fluoro, —N(CH$_3$)(CH$_3$), —OCH$_3$, (C$_1$-C$_6$) alkyl, or phenyl optionally substituted with halo, unsubstituted C$_1$-C$_6$ alkyl, halo(C$_1$-C$_6$)alkyl, unsubstituted C$_1$-C$_6$ alkoxy, halo(C$_1$-C$_6$)alkoxy, cyano or nitro and Z is selected from hydrogen, C$_1$-C$_6$ alkyl, phenyl and N(R$^3$)(R$^4$), wherein the phenyl in the group represented by Z is optionally substituted with halo, unsubstituted C$_1$-C$_6$ alkyl, halo(C$_1$-C$_6$)alkyl, unsubstituted C$_1$-C$_6$ alkoxy, halo(C$_1$-C$_6$)alkoxy, cyano or nitro. In another alternative, Y is hydrogen, chloro, fluoro, —N(CH$_3$)(CH$_3$)—OCH$_3$, (C$_1$-C$_6$) alkyl, or phenyl optionally substituted with halo, unsubstituted C$_1$-C$_6$ alkyl, halo(C$_1$-C$_6$)alkyl, unsubstituted C$_1$-C$_6$ alkoxy, halo(C$_1$-C$_6$)alkoxy, cyano or nitro, and Z is hydrogen, —NH$_2$, —NH(CH$_2$)$_2$CH$_3$, —NH(CH$_2$)$_2$OCH$_3$, —NHCH$_2$CF$_3$ or —NHCH$_2$C(CH$_3$)$_2$CH$_2$N(CH$_3$)CH$_3$. In yet another alternative, Z is hydrogen, —NH$_2$, —NH(CH$_2$)$_2$CH$_3$, —NH(CH$_2$)$_2$OCH$_3$, —NHCH$_2$CF$_3$ or —NHCH$_2$C(CH$_3$)$_2$CH$_2$N(CH$_3$)CH$_3$ and Y is hydrogen, chloro, fluoro, or —N(CH$_3$)(CH$_3$).

In a specific aspect of the second embodiment, Y and Z are not simultaneously hydrogen.

A third embodiment is a compound of Structural Formula III, or a pharmaceutically acceptable salt thereof:

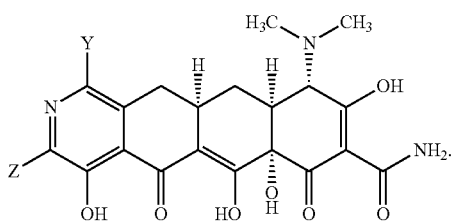

III

Values and alternative values for the variables in Structural Formula III are as defined for Structural Formula I above. Alternatively, Y is hydrogen, chloro, fluoro, —N(CH$_3$)(CH$_3$), —OCH$_3$, phenyl or (C$_1$-C$_6$)alkyl and X is hydrogen or (C$_1$-C$_6$)alkyl. In one specific aspect of the third embodiment, Y is not hydrogen. In another specific aspect of the third embodiment, Y is fluoro, chloro, C$_1$-C$_6$ alkyl, C$_1$-C$_6$ alkoxy, (C$_0$-C$_6$) alkylene-N(R$^1$)(R$^2$) and phenyl.

Specific examples of compounds of the invention are represented by Structural Formula I, wherein X, Y and Z are as defined in the table below:

| Compound # | X | Y | Z |
|---|---|---|---|
| 100 | H | F | CH$_3$-N(CH$_3$)-C(O)-NH- |
| 101 | H | Cl | H$_3$C-NH- |
| 102 | H | H | H |

-continued

| Compound # | X | Y | Z |
|---|---|---|---|
| 103 | H– | Cl– | H₃C– |
| 104 | H– | Cl– | H₃C-CH(–)-CH₂-CH₃ (sec-butyl) |
| 105 | H– | (H₃C)₃C-CH₂-NH-C(–)< | H– |
| 106 | H– | F– | 4-methylpiperazin-1-yl |
| 107 | H– | Cl– | (R)-H₃C-CH(Ph)-NH– |
| 108 | H– | Cl– | pyrrolidin-1-yl-CH₂-C(CH₃)₂-CH₂-NH– |
| 109 | H– | (H₃C)₂N– | H– |
| 110 | H– | Cl– | H₃C-CH₂-NH– |
| 111 | 4-(F₃CO)-C₆H₄– | H– | H– |
| 112 | H– | Cl– | (H₃C)₂CH-CH₂-NH– |
| 113 | H₃C-CH₂– | H– | H– |
| 114 | H– | F– | H₃C-CH₂-CH₂-NH– |

-continued

| Compound # | X | Y | Z |
|---|---|---|---|
| 115 | H— | Cl— | H₃C-C(CH₃)₂-CH₂-NH— |
| 116 | H— | H— | (CH₃)₂CH-CH₂-NH— |
| 117 | H— | Cl— | HO-CH₂-C— |
| 118 | H— | (H₃C)₂N— | H₃C-CH₂-CH₂-NH— |
| 119 | H— | Cl— | (H₃C)₂N-CH₂CH₂CH₂-NH— |
| 120 | H— | F— | (H₃C)₃C-NH-CH₂-C(=O)-NH— |
| 121 | H— | H₃CO— | H— |
| 122 | H— | H— | HO-CH₂-C— |
| 123 | H— | Cl— | H— |
| 124 | H— | Cl— | F₃C-CH₂-NH— |
| 125 | H— | F— | H₂N— |
| 126 | H— | Cl— | (H₃C)₂CH-CH₂-CH₂-NH— |
| 127 | H— | H— | (H₃C)₃C-CH₂-C(=O)-NH— |

-continued

| Compound # | X | Y | Z |
|---|---|---|---|
| 128 | H | H | -N(CH₃)CH₂-... dimethylamino group with methyl |
| 129 | H | Cl | tert-butyl-NH-CH₂-C(CH₃)₂-CH₂-NH- |
| 130 | H | H | (CH₃)₂N-CH₂-C(CH₃)₂-CH₂-NH- |
| 131 | H | Cl | phenyl-NH-C(=O)-NH- |
| 132 | H | Cl | tert-butyl-NH-CH₂-C(=O)-NH- |
| 133 | H | F | (CH₃)₂N-CH₂-C(CH₃)₂-CH₂-NH- |
| 134 | H | Cl | isopropyl-NH-(CH₂)₃-NH- |
| 135 | H | H | tert-butyl-NH-CH₂-C(CH₃)₂-CH₂-NH- |
| 136 | H | Cl | phenyl- |
| 137 | H | H | (CH₃)₃C-CH₂-NH- |
| 138 | H | F | Br- |
| 139 | H | Cl | phenyl-NH- |

-continued

| Compound # | X | Y | Z |
|---|---|---|---|
| 140 | H— | Cl— | (CH3)(H3C)N-CH2-CH2-NH— |
| 141 | H— | (H3C)2N— | H3C-CH2-CH< |
| 142 | H— | (H3C)2N— | CH3-NH-C(=O)-NH— |
| 143 | H— | Cl— | H3C-NH-C(=O)-NH— |
| 144 | H— | F— | H— |
| 145 | H— | (H3C)2N— | (CH3)(H3C)N-CH2-CH2-CH2— |
| 146 | H— | H— | H2N— |
| 147 | H— | Cl— | H2N— |
| 148 | H— | Cl— | (H3C)(H3C)(H3C)C-CH2-CH2-NH— |
| 149 | H— | (H3C)2N— | (H3C)3C-NH-CH2-C(=O)-NH— |
| 150 | H— | Cl— | H3C-O-CH2-CH2-NH— |
| 151 | H— | Cl— | (H3C)(H3C)N-CH2-C(CH3)2-CH2-NH— |
| 152 | H— | H3C— | H— |

-continued

| Compound # | X | Y | Z |
|---|---|---|---|
| 153 | H– | Cl– | (CH3)2CH-O-CH2CH2-NH– |
| 154 | H– | Cl– | H3C-CH2CH2CH2-NH– |
| 155 | H– | (CH3)2CH-CH2-NH-C(CH3)– | H– |
| 156 | H– | Cl– | H3C-CH2CH2-NH– |
| 157 | H– | Cl– | (CH3)2CH-NH– |
| 158 | H– | H– | H3C-C(CH3)2– |
| 159 | H– | H– | (CH3)2N-C(CH3)– |
| 160 | H– | C6H5– | H– |
| 161 | H– | H– | H3C-NH-C(CH3)– |
| 162 | H– | Cl– | cyclopropyl-CH2-NH– |
| 163 | H– | F– | pyrrolidinyl-CH2-C(=O)-NH– |
| 164 | H– | H– | azetidinyl-CH2-C(CH3)– |
| 165 | H– | H– | C6H5-C(CH3)– |

Preferred Examples of the compounds of the invention are selected from any one of Compound 101, 102, 109, 110, 124, 125, 144, 146, 147, 150, 151, and 156, or a pharmaceutically acceptable salt thereof. Alternatively, Preferred Examples of the compounds of the invention are selected from any one of Compound 101, 109, 110, 124, 125, 144, 146, 147, 150, 151, and 156, or a pharmaceutically acceptable salt thereof.

DEFINITIONS

"Alkyl" means a saturated aliphatic branched or straight-chain monovalent hydrocarbon radical having the specified number of carbon atoms. Thus, "$(C_1-C_6)$ alkyl" means a radical having from 1-6 carbon atoms in a linear or branched arrangement. "$(C_1-C_6)$alkyl" includes methyl, ethyl, propyl, butyl, pentyl and hexyl.

"Alkylene" means a saturated aliphatic straight-chain divalent hydrocarbon radical having the specified number of carbon atoms. Thus, "$(C_1-C_6)$ alkylene" means a divalent saturated aliphatic radical having from 1-6 carbon atoms in a linear arrangement. "$(C_1-C_6)$alkylene" includes methylene, ethylene, propylene, butylene, pentylene and hexylene.

"Heterocycle" means a saturated or partially unsaturated (4-7 membered) monocyclic heterocyclic ring containing one nitrogen atom and optionally 1 additional heteroatom independently selected from N, O or S. When one heteroatom is S, it can be optionally mono- or di-oxygenated (i.e. —S(O)— or —S(O)$_2$—).

Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, or isothiazolidine 1,1-dioxide.

"Cycloalkyl" means saturated aliphatic cyclic hydrocarbon ring. Thus, "$C_3-C_7$ cycloalkyl" means (3-7 membered) saturated aliphatic cyclic hydrocarbon ring. $C_3-C_7$ cycloalkyl includes, but is not limited to cyclopropyl, cyclobutyl, cyclopentyl, cyclohexyl and cycloheptyl.

"Alkoxy" means an alkyl radical attached through an oxygen linking atom. "$(C_1-C_6)$-alkoxy" includes methoxy, ethoxy, propoxy, butoxy, pentoxy and hexoxy.

Haloalkyl and halocycloalkyl include mono, poly, and perhaloalkyl groups where each halogen is independently selected from fluorine, chlorine, and bromine.

"Hetero" refers to the replacement of at least one carbon atom member in a ring system with at least one heteroatom selected from N, S, and O. A hetero ring system may have 1 or 2 carbon atom members replaced by a heteroatom.

"Halogen" and "halo" are interchangeably used herein and each refers to fluorine, chlorine, bromine, or iodine.

"Cyano" means —C≡N.

"Nitro" means —NO$_2$.

Another embodiment of the present invention is a pharmaceutical composition comprising one or more pharmaceutically acceptable carrier and/or diluent and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

The present invention also provides a method of treating a subject with a tetracycline-responsive disease or disorder comprising administering to the subject an effective amount of a compound of the present invention or a pharmaceutically acceptable salt thereof.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion, metastasis, acute lung injury, stroke, ischemia, diabetes, aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis; uremic pericarditis; acute and chronic cholecystis; cystic fibrosis, acute and chronic vaginitis; acute and chronic uveitis; drug reactions; insect bites; burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48: 6686-6690 (1988)).

Infections that can be treated using compounds of the invention or a pharmaceutically acceptable salt thereof include, but are not limited to, skin infections, GI infections, urinary tract infections, genito-urinary infections, respiratory tract infections, sinuses infections, middle ear infections, systemic infections, cholera, influenza, bronchitis, acne, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection can be caused bacteria. In another embodiment, the infection is caused by a Gram-positive bacteria. In a specific aspect of this embodiment, the infection is caused by a Gram-positive bacteria selected from *S. aureus, S. pneumoniae, P. granulosum* and *P. acnes.*

In another embodiment, the infection is caused by a Gram-negative bacteria. In a specific aspect of this embodiment, the infection is caused by a Gram-negative bacteria selected from *E. coli* or *B. thetaiotaomicron.*

In another embodiment, the infection is caused by an organism selected from the group consisting of *K. pneumoniae, Salmonella, E. hirae, A. baumanii, B. catarrhalis, H. influenzae, P. aeruginosa, E. faecium, E. coli, S. aureus,* and *E. faecalis.* In another embodiment, the infection is caused by an organism selected from the group consisting of rickettsiae, chlamydiae, and *Mycoplasma pneumoniae.* In another embodiment, the infection is caused by an organism resistant to tetracycline. In another embodiment, the infection is caused by an organism resistant to methicillin. In another embodiment, the infection is caused by an organism resistant to vancomycin. In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria.

In another embodiment, the infection is caused by a Gram-positive bacterium. In a specific aspect of this embodiment, the infection is caused by a Gram-positive bacterium selected from class *Bacilli*, including, but not limited to, *Staphylococcus* spp., *Streptococcus* spp., *Enterococcus* spp., *Bacillus* spp., *Listeria* spp.; phylum Actinobacteria, including, but not limited to, *Propionibacterium* spp., *Corynebacterium* spp., *Nocardia* spp., *Actinobacteria* spp., and class Clostridia, including, but not limited to, *Clostridium* spp.

In another embodiment, the infection is caused by a Gram-negative bacterium. In one aspect of this embodiment, the infection is caused by a phylum *Proteobacteria* (e.g., *Betaproteobacteria* and *Gammaproteobacteria*), including *Escherichia coli, Salmonella, Shigella,* other *Enterobacteriaceae, Pseudomonas, Moraxella, Helicobacter, Stenotrophomonas, Bdellovibrio,* acetic acid bacteria, *Legionella* or alpha-proteobacteria such as *Wolbachia*. In another aspect, the infection is caused by a Gram-negative bacterium selected from cyanobacteria, spirochaetes, green sulfur or green nonsulfur bacteria. In a specific aspect of this embodiment, the infection is caused by a Gram-negative bacteria selected from *Enterobactericeae* (e.g., *E. coli, Klebsiella pneumoniae* including those containing extended-spectrum β-lactamases and/or carbapenemases), *Bacteroidetes* (e.g., *Bacteroides fragilis*), *Vibrionaceae* (*Vibrio cholerae*), *Pasteurellaceae* (e.g., *Haemophilus influenzae*), *Pseudomonadaceae* (e.g., *Pseudomonas aeruginosa*), *Neisseriaceae* (e.g. *Neisseria meningitidis*), *Rickettsiae, Moraxellaceae* (e.g., *Moraxella catarrhalis*), any species of *Proteeae, Acinetobacter* spp., *Helicobacter* spp., and *Campylobacter* spp. In a particular embodiment, the infection is caused by Gram-negative bacterium selected from the group consisting of *Enterobactericeae* (e.g., *E. coli, Klebsiella pneumoniae*), *Pseudomonas,* and *Acinetobacter* spp. In another embodiment, the infection is caused by an organism selected from the group consisting of *K. pneumoniae, Salmonella, E. hirae, A. baumanii, M. catarrhalis, H. influenzae, P. aeruginosa, E. faecium, E. coli, S. aureus,* and *E. faecalis.*

In one embodiment, the infection is caused by an organism that grows intracellularly as part of its infection process.

In another embodiment, the infection is caused by an organism selected from the group consisting of order *Rickettsiales; phylum Chlamydiae;* order *Chlamydiales; Legionella* spp.; class *Mollicutes*, including, but not limited to, *Mycoplasma* spp. (e.g. *Mycoplasma pneumoniae*); *Mycobacterium* spp. (e.g. *Mycobacterium tuberculosis*); and phylum *Spriochaetales* (e.g. *Borrelia* spp. and *Treponema* spp.).

In another embodiment, the infection is caused by a Category A Biodefense organism as described at http://www.bt.cdc.gov/agent/agentlist-category.asp, the entire teachings of which are incorporated herein by reference. Examples of Category A organisms include, but are not limited to, *Bacillus anthracis* (anthrax), *Yersinia pestis* (plague), *Clostridium botulinum* (botulism) or *Francisella tularensis* (tularemia). In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria.

Additional infections that can be treated using compounds of the invention or a pharmaceutically acceptable salt thereof include, but are not limited to, anthrax, botulism, bubonic plague, and tularemia.

In another embodiment, the infection is caused by a Category B Biodefense organism as described at http://www.bt.cdc.gov/agent/agentlist-category.asp, the entire teachings of which are incorporated herein by reference. Examples of Category B organisms include, but are not limited to, *Brucella* spp, *Clostridium perfringens, Salmonella* spp., *Escherichia coli* O157:H7, *Shigella* spp., *Burkholderia mallei, Burkholderia pseudomallei, Chlamydia psittaci, Coxiella burnetii, Staphylococcal enterotoxin* B, *Rickettsia prowazekii, Vibrio cholerae,* and *Cryptosporidium parvum.*

Additional infections that can be treated using compounds of the invention or a pharmaceutically acceptable salt thereof include, but are not limited to, *Brucellosis, Clostridium perfringens*, food-borne illnesses, Glanders, Melioidosis, Psittacosis, Q fever, and water-borne illnesses.

In yet another embodiment, the infection can be caused by one or more than one organism described above. Examples of such infections include, but are not limited to, intra-abdominal infections (often a mixture of a gram-negative species like *E. coli* and an anaerobe like *B. fragilis*), diabetic foot (various combinations of *Streptococcus, Serratia, Staphylococcus* and *Enterococcus* spp., anaerobes (S. E. Dowd, et al., PloS one 2008; 3:e3326, the entire teachings of which are incorporated herein by reference) and respiratory disease (especially in patients that have chronic infections like cystic fibrosis—e.g., *S. aureus* plus *P. aeruginosa* or *H. influenzae*, atypical pathogens), wounds and abscesses (various gram-negative and gram-positive bacteria, notably MSSA/MRSA, coagulase-negative *staphylococci, enterococci, Acinetobacter, P. aeruginosa, E. coli, B. fragilis*), and bloodstream infections (13% were polymicrobial (H. Wisplinghoff, et al., Clin. Infect. Dis. 2004; 39:311-317, the entire teachings of which are incorporated herein by reference)).

In one embodiment, the infection is caused by an organism resistant to one or more antibiotics.

In another embodiment, the infection is caused by an organism resistant to tetracycline or any member of first and second generation of tetracycline antibiotics (e.g., doxycycline or minocycline).

In another embodiment, the infection is caused by an organism resistant to methicillin.

In another embodiment, the infection is caused by an organism resistant to vancomycin.

In another embodiment, the infection is caused by an organism resistant to a quinolone or fluoroquinolone.

In another embodiment, the infection is caused by an organism resistant to tigecycline or any other tetracycline derivative. In a particular embodiment, the infection is caused by an organism resistant to tigecycline.

In another embodiment, the infection is caused by an organism resistant to a β-lactam or cephalosporin antibiotic or an organism resistant to penems or carbapenems.

In another embodiment, the infection is caused by an organism resistant to an antimicrobial peptide or a biosimilar therapeutic treatment. Antimicrobial peptides (also called host defense peptides) are an evolutionarily conserved component of the innate immune response and are found among all classes of life. In this case, antimicrobial peptide refers to any naturally occurring molecule or any semi/synthetic molecule that are analogs of anionic peptides, linear cationic α-helical peptides, cationic peptides enriched for specific amino acids (i.e., rich in proline, arginine, phenylalanine, glycine, tryptophan), and anionic and cationic peptides that contain cystein and form disulfide bonds.

In another embodiment, the infection is caused by an organism resistant to macrolides, lincosamides, streptogramin antibiotics, oxazolidinones, and pleuromutilins.

In another embodiment, the infection is caused by an organism resistant to PTK0796 (7-dimethylamino, 9-(2,2-dimethyl-propyl)-aminomethylcycline).

In another embodiment, the infection is caused by a multidrug-resistant pathogen (having intermediate or full resistance to any two or more antibiotics).

In a further embodiment, the tetracycline responsive disease or disorder is not a bacterial infection. In another embodiment, the tetracycline compounds of the invention are essentially non-antibacterial. For example, non-antibacterial compounds of the invention may have MIC values greater than about 4 μg/ml (as measured by assays known in the art and/or the assay given in Example 1.

Tetracycline responsive disease or disorder also includes diseases or disorders associated with inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity. Examples of matrix metalloproteinase associated states ("MMPAS's") can be treated using compounds of the invention or a pharmaceutically acceptable salt thereof, include, but are not limited to, arteriosclerosis, corneal ulceration, emphysema, osteoarthritis, multiple sclerosis (Liedtke et al., Ann Neurol. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998, 22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compounds of the present invention or a pharmaceutically acceptable salt thereof include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. No. 6,100,248; 5,843,925; 5,837,696; or 5,668,122, incorporated herein by reference in their entirety.

Alternatively, the tetracycline compounds may be useful for preventing or reducing the likelihood of cancer recurrence, for example, to treat residual cancer following surgical resection or radiation therapy. The tetracycline compounds useful according to the invention are especially advantageous as they are substantially non-toxic compared to other cancer treatments.

In a further embodiment, the compounds of the invention are administered in combination with standard cancer therapy, such as, but not limited to, chemotherapy.

Examples of tetracycline responsive states can be treated using the compounds of the invention or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoffs psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compounds of the invention or a pharmaceutically acceptable salt thereof include, but are not limited to, juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorders of the invention also include chronic lung disorders. Examples of chronic lung disorders that can be treated using the compounds of the invention or a pharmaceutically acceptable salt thereof include, but are not limited, to asthma, cystic fibrosis, chronic obstructive pulmonary disease (COPD), and emphysema. In a further embodiment, the acute and/or chronic lung disorders that can be treated using the compounds of the invention or a pharmaceutically acceptable salt thereof include those described in U.S. Pat. Nos. 5,977,091; 6,043,231; 5,523,297; and 5,773,430, each of which is hereby incorporated herein by reference in its entirety.

In yet another embodiment, the tetracycline responsive disease or disorder is ischemia, stroke, or ischemic stroke.

In a further embodiment, the tetracycline compounds of the invention or a pharmaceutically acceptable salt thereof can be used to treat such disorders as described above and in U.S. Pat. Nos. 6,231,894; 5,773,430; 5,919,775 and 5,789,395, incorporated herein by reference.

In still a further embodiment, the tetracycline compounds of the invention or a pharmaceutically acceptable salt thereof can be used to treat pain, for example, inflammatory, nociceptive or neuropathic pain. The pain can be either acute or chronic.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a tetracycline compound of the invention or a pharmaceutically acceptable salt thereof to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e.g., topically). In a further embodiment, the tetracycline compound of the invention or a pharmaceutically acceptable salt thereof is used to treat a skin wound, and other such disorders as described in, for example, U.S. Pat. Nos. 5,827,840; 4,704,383; 4,935,412; 5,258,371; 5,308, 839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The tetracycline compound or a pharmaceutically acceptable salt thereof may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834, 449, incorporated herein by reference in their entirety.

The compounds of the invention or a pharmaceutically acceptable salt thereof can be used alone or in combination with one or more therapeutic agent in the methods of the invention disclosed herein.

The language "in combination with" another therapeutic agent or treatment includes co-administration of the tetracycline compound and with the other therapeutic agent or treatment as either a single combination dosage form or as multiple, separate dosage forms, administration of the tetracycline compound first, followed by the other therapeutic agent or treatment and administration of the other therapeutic agent or treatment first, followed by the tetracycline compound.

The other therapeutic agent may be any agent that is known in the art to treat, prevent, or reduce the symptoms of a tetracycline-responsive disease or disorder. The choice of additional therapeutic agent(s) is based upon the particular tetracycline-responsive disease or disorder being treated. Such choice is within the knowledge of a treating physician. Furthermore, the other therapeutic agent may be any agent of benefit to the patient when administered in combination with the administration of a tetracycline compound.

As used herein, the term "subject" means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

As used herein, the term "treating" or "treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

"Effective amount" means that amount of active compound agent that elicits the desired biological response in a subject. Such response includes alleviation of the symptoms of the disease or disorder being treated. In one embodiment, the effective amount of a compound of the invention is from about 0.01 mg/kg/day to about 1000 mg/kg/day, from about 0.1 mg/kg/day to about 100 mg/kg/day, or from about 0.5 mg/kg/day to about 50 mg/kg/day.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

Compounds of the invention may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration in the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the composition of this invention includes one or more additional agents. The other therapeutic agent may be ay agent that is capable of treating, preventing or reducing the symptoms of a tetracycline-responsive disease or disorder. Alternatively, the other therapeutic agent may be any agent of benefit to a patient when administered in combination with the tetracycline compound in this invention.

EXEMPLIFICATION

The following abbreviations and the terms have the indicated meanings:

| Abbreviations | |
|---|---|
| $(Boc)_2O$ | di-tert-butyl dicarbonate |
| Ac | acetyl |
| aq | aqueous |
| $BBr_3$ | boron tribromide |
| Bn | benzyl |
| Boc | tert-butoxy carbonyl or t-butoxy carbonyl |
| br | broad |
| brine | saturated aqueous sodium chloride |
| Bu | butyl |
| Cbz | benzyloxycarbonyl |
| $CH_2Cl_2$ | methylene chloride |
| $CH_3CN$ or MeCN | acetonitrile |
| d | doublet |
| dba | dibenzylideneacetone |
| DIC | diisopropylcarbodiimide |
| DIEA | N,N-diisopropylethylamine |
| DMAP | 4-(dimethylamino)pyridine |
| DMF | N, N-dimethylformamide |
| DMSO | dimethyl sulfoxide |
| eq or equiv | equivalent |
| ESI | electrospray ionization |
| Et | ethyl |
| $Et_2O$ | ethyl ether |
| EtOAc | ethyl acetate |
| h, hr | hour |
| HCl | hydrochloric acid |
| HOBt | 1-hydroxybenzotriazole |
| HPLC | high performance liquid chromatography |
| J | coupling constant |
| $KHPO_4$ | potassium hydrogenphosphate |
| LDA | lithium diisopropylamide |
| LHMDS | lithium bis(trimethylsilyl)amide |
| m/z | mass-to-charge ratio |
| mCPBA | meta-chloroperoxybenzoic acid |
| Me | methyl |
| MeI | methyl iodide |
| MeOH | methanol |
| min | minute |
| MS | mass spectrum |
| Ms | methanesulfonyl |
| MS | mass spectrometry |
| MW | molecular weight |
| n | normal |
| $Na_2SO_4$ | sodium sulfate |
| $NaHCO_3$ | sodium bicarbonate |
| NaOH | sodium hydroxide |
| NMP | 1-methyl-2-pyrrolidinone |
| NMR | nuclear magnetic resonance spectrometry |
| NOE | nuclear overhauser effect |
| o-tol | ortho-tolyl |
| Ph | phenyl |
| q | quartet |
| $R_f$ | retention factor |
| RP | reverse phase |
| rt | room temperature |
| s | singlet |
| t | triplet |
| TBAF | tetrabutylammonium fluoride |
| TBS | tert-butyldimethylsilyl |
| THF | tetrahydrofuran |
| TLC | thin layer chromatography |
| TMEDA | N,N,N'N'-tetramethylethylenediamine |
| Xantphos | 4,5-bis(diphenylphosphino)-9,9-dimethylxanthene |

Example 1

Preparation of Intermediates Useful in Synthesizing Compounds of the Invention Intermediates useful in synthesizing compounds of the invention were prepared according to Scheme 1.

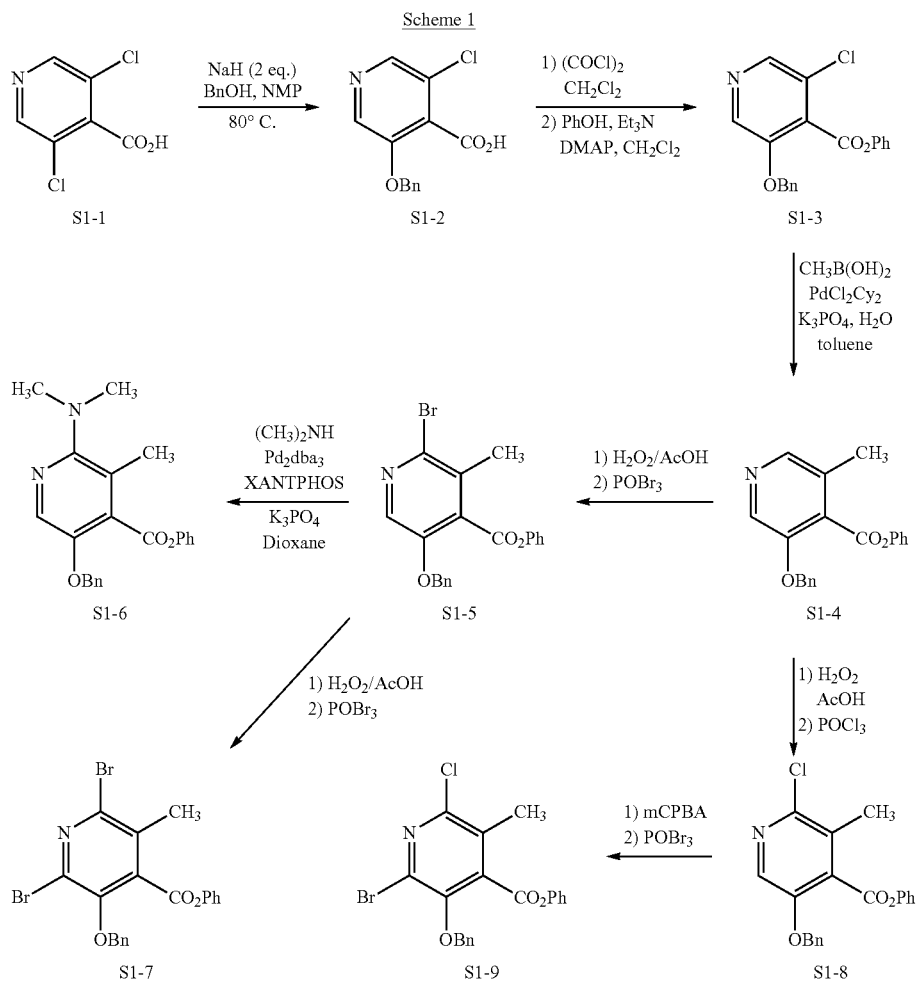

Scheme 1

Synthesis of S1-2

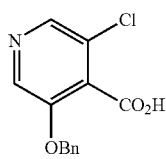

Sodium hydride (60% dispersion in mineral oil, 4.37 g, 109 mmol) was added portion wise to a solution of 3,5-dichloroisonicotinic acid (10.24 g, 53.3 mmol) in NMP (100 mL). After gas evolution ceased, benzyl alcohol (5.52 mL, 53.3 mmol) was added drop wise. After gas evolution ceased, the reaction mixture was heated to 80° C. After 1 hr, the reaction was complete and was allowed to cool to rt and stand overnight. The reaction mixture was diluted with water (300 mL) and was washed with Et$_2$O (2×100 mL, discarded). The aqueous layer was brought to pH ~2 with conc. HCl, causing a precipitate to form. The mixture was diluted with brine (100 mL) and was allowed to stand for 30 minutes. The solid was collected by filtration, washed with water (3×), and was dried in a 45° C. vacuum oven overnight. This gave 9.36 g (67%) of the product as a white solid. $^1$H NMR (400 MHz, DMSO-d6) δ 14.30-14.10 (bs, 1H), 8.52 (s, 1H), 8.34 (s, 1H), 7.50-7.30 (m, 5H), 5.33 (s, 2H); MS (ESI) m/z 264.20 (M+H).

Synthesis of S1-3

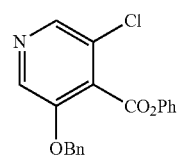

Oxalyl chloride (4.9 mL, 56 mmol) was added to a suspension of S1-2 (3.71 g, 14.1 mmol) in CH$_2$Cl$_2$ (50 mL) over ~2 minutes. DMF was added drop wise in ~20 µL portions every 5 minutes until complete solution was achieved. After stirring for an additional 30 minutes, the reaction mixture was concentrated under reduced pressure. The resulting solid was dissolved in CH$_2$Cl$_2$ (50 mL) and phenol (2.65 g, 28.1 mmol), DMAP (0.172 g, 1.41 mmol), and Et$_3$N (9.76 mL, 70.4 mmol) were added. After 1 hr, the reaction mixture was diluted with CH$_2$Cl$_2$ (50 mL) and was washed with water (2×100 mL) and NaHCO$_3$ (saturated, aqueous, 100 mL). The organics were dried over Na$_2$SO$_4$, filtered, and concentrated under reduced pressure. The material was purified by column chromatography (Biotage 50 g column, 0 to 25% EtOAc in hexanes gradient), yielding 4.20 g (88%) of the product as an off-white solid. R$_f$=0.43 in 30% EtOAc/hexanes. $^1$H NMR (400 MHz, DMSO-d6) δ 8.70 (s, 1H), 8.48 (s, 1H), 7.52-7.30 (m, 8H), 7.15-7.08 (m, 2H), 5.44 (s, 2H); MS (ESI) m/z 340.25 (M+H).

Synthesis of S1-4

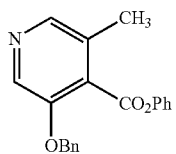

S1-4

Intermediate S1-3 (2.01 g, 5.92 mmol), methyl boronic acid (1.06 g, 17.7 mmol), dichlorobis(tricyclohexylphosphine)palladium(II) (102 mg, 0.296 mmol), and K$_3$PO$_4$ (3.76 g, 17.7 mmol) were heated to 100° C. in toluene (20 mL) and water (2 mL). After 16 hr, the reaction mixture was allowed to cool to rt and was diluted with EtOAc (20 mL). This was washed with water (20 mL) and brine (20 mL), dried over Na$_2$SO$_4$, filtered, and concentrated under reduced pressure. The material was purified by column chromatography (Biotage 50 g column, 0 to 40% EtOAc/hexanes gradient), yielding 1.66 g (88%) of the product as a white solid. R$_f$=0.18 in 30% EtOAc/hexanes. $^1$H NMR (400 MHz, DMSO-d6) δ 8.50 (s, 1H), 8.26 (s, 1H), 7.52-7.30 (m, 8H), 7.20-7.10 (m, 2H), 5.37 (s, 2H), 2.38 (s, 3H); MS (ESI) m/z 320.27 (M+H).

Synthesis of S1-5

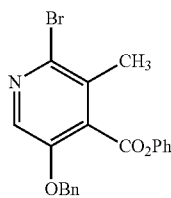

S1-5

Intermediate S1-4 (25.9 g, 81.1 mmol) was heated to 80° C. in acetic acid (160 mL) and hydrogen peroxide (30% aqueous solution, 40 mL). After stirring overnight, LC/MS indicated that the starting material was consumed and the N-oxide present. The reaction mixture was concentrated under reduced pressure, diluted with EtOAc, and washed with NaHCO$_3$ (saturated aqueous solution, 3 times). The organics were dried over Na$_2$SO$_4$, filtered, and concentrated under reduced pressure, yielding 25.4 g (93% crude) of the N-oxide as a tan solid. The material was suspended in toluene (200 mL) and heated to 80° C. at which point most of the solid had dissolved. Phosphorus oxybromide (25 g, 87.2 mmol) was added in one portion. After 30 minutes, LC/MS indicated the reaction was complete. Upon cooling to rt, the reaction mixture was poured into a solution of K$_2$CO$_3$ (83 g) in water (300 mL). Additional water (~50 mL) was used to transfer the remaining material in the reaction flask into the K$_2$CO$_3$ solution. This was stirred for 30 minutes at rt. The layers were separated, and the aqueous layer was extracted with EtOAc. The combined extracts were dried over MgSO4, filtered through Celite, and concentrated under reduced pressure. The material was re-crystallized from EtOAc/hexanes (1:1), yielding 20.6 g (64%) of the product as an off-white solid. Single isomer by 1H-NMR. $^1$H NMR (400 MHz, CDCl$_3$) δ 8.05 (s, 1H), 7.43-7.30 (m, 7H), 7.29-7.20 (m, 1H), 7.07 (d, J=8.2 Hz, 2H), 5.21 (s, 2H), 2.46 (s, 3H); MS (ESI) m/z 398.22, 400.22 (M+H).

Synthesis of S1-6

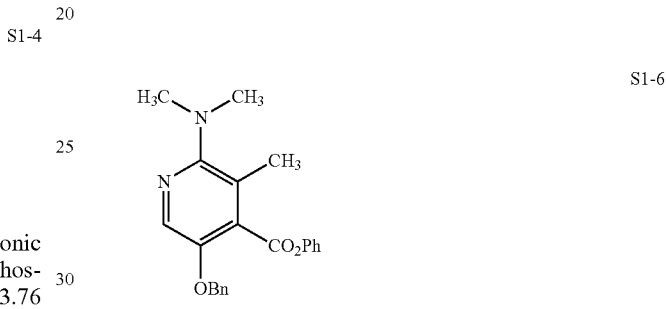

S1-6

Intermediate S1-5 (1.06 g, 2.66 mmol), dimethylamine (2.0 M solution in THF, 4.0 mL, 8.0 mmol), K$_3$PO$_4$ (1.7 g, 8.0 mmol), tris(dibenzylidene-acetone)dipalladium (120 mg, 0.13 mmol) and 9,9-dimethyl-4,5-bis-(diphenyl-phosphinoxanthene (220 mg, 0.40 mmol) were heated to 100° C. in 1,4-dioxane (10 mL) in a sealed pressure vessel. After heating overnight, the reaction mixture was cooled to rt, was diluted with EtOAc (100 mL), and was washed with water (3×50 mL) and brine (50 mL). The organics were dried over Na$_2$SO$_4$, filtered, and concentrated under reduced pressure. The material was purified by column chromatography (Biotage 50 g column, 0 to 15% EtOAc in hexanes gradient), yielding 388 mg (40%) of intermediate S1-6. $^1$H NMR (400 MHz, CDCl$_3$) δ 7.96 (s, 1H), 7.45-7.20 (m, 8H), 7.08 (d, J=8.2 Hz, 2H), 5.16 (s, 2H), 2.76 (s, 6H), 2.37 (s, 3H); MS (ESI) m/z 363.45 (M+H).

Synthesis of S1-7

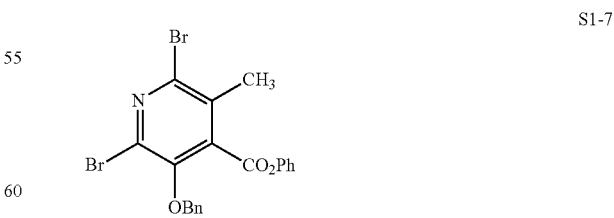

S1-7

Intermediate S1-5 (8.54 g, 21.4 mmol) was heated to 80° C. in acetic acid (120 mL) and hydrogen peroxide (30% aqueous solution, 30 mL). After stirring overnight, LC/MS indicated that the starting material was mostly consumed and the N-oxide present. The reaction mixture was cooled to rt and diluted with brine (150 mL). The mixture was cooled in a −20° C. freezer for 30 minutes. The resulting precipitate was collected by filtration and was washed with water/brine (1:1, 2 times). The solid was dissolved in $CH_2Cl_2$ and was dried over $Na_2SO_4$, filtered, and concentrated under reduced pressure. This gave 7.83 g (88% crude) of the N-oxide as a tan solid. The material was suspended in toluene (200 mL) and was heated to 100° C. at which point most of the solid had dissolved. A solution of phosphorous oxybromide (10.8 g, 37.8 mmol) in toluene (10 mL) was added rapidly. After 45 minutes, LC/MS indicated the reaction was complete. Upon cooling to rt, the reaction mixture was poured into a solution of $K_2CO_3$ (40 g) in water (150 mL). Additional water (~50 mL) was used to transfer the remaining material in the reaction flask into the $K_2CO_3$ solution. This was stirred for 30 minutes at rt. The layers were separated, and the aqueous layer was extracted with EtOAc. The combined extracts were dried over $MgSO_4$, filtered, and concentrated under reduced pressure. The material was purified by column chromatography (Biotage 50 g column, 0 to 8% EtOAc in hexanes gradient to isolate the product then 15% EtOAc in hexanes to recover starting material), yielding 5.02 g (49%) of the product as an off-white solid. Intermediate S1-5 was also recovered. $^1$H NMR (400 MHz, DMSO-d6) δ 7.49-7.32 (m, 8H), 7.10 (d, J=7.3 Hz, 2H), 5.15 (s, 2H), 2.41 (s, 3H); MS (ESI) m/z 476.18, 478.16, 480.16 (M+H).

Synthesis of S1-8

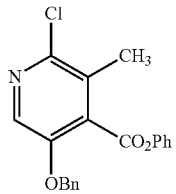

S1-8

Intermediate S1-4 (9.66 g, 30.28 mmol) was heated to 80° C. in acetic acid (50 mL) and hydrogen peroxide (30% aqueous solution, 16.9 mL, 5 equiv). After 6 hr, LC/MS indicated that the starting material was consumed and the N-oxide present. Most of the acetic acid and water were removed by rotovap at 40° C. The material was then diluted with EtOAc (200 mL) and washed with $NaHCO_3$ (saturated aqueous solution, 3×50 mL). The organics were dried over $Na_2SO_4$, filtered, and concentrated under reduced pressure. This gave 9.37 g (92% crude yield) of the N-oxide. This was dissolved in toluene (60 mL). Phosphorous oxychloride (7.69 g, 3 equiv) was added and the reaction mixture was heated to 100° C. After 2 hr, LC/MS indicated that the reaction was complete. Upon cooling to rt, the reaction mixture was poured into a solution of $K_2CO_3$ (40 g) in water (200 mL). This mixture was extracted with EtOAc (3×150 mL), and the combined extracts were dried over $Na_2SO_4$, filtered, and concentrated under reduced pressure. $^1$H-NMR indicated a mixture of regioisomers (4.5:1). The material was re-dissolved in EtOAc (30 mL) with heating and was then allowed to cool to rt and stand overnight. A white crystalline solid was obtained (4.99 g, 51%). Another 1.92 g (19%) of the white crystalline solid was obtained from the mother liquor after standing in a refrigerator overnight. Both are the desired pure regioisomer S1-8 by $^1$H-NMR. $^1$H NMR (400 MHz, CDCl$_3$) δ 8.05 (s, 1H), 7.43-7.30 (m, 7H), 7.29-7.22 (m, 1H), 7.08 (d, J=8.2 Hz, 2H), 5.22 (s, 2H), 2.45 (s, 3H); MS (ESI) m/z 354.11 (M+H).

Synthesis of S1-9

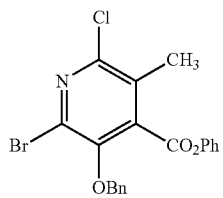

S1-9

Intermediate S1-8 (4.99 g, 14.1 mmol) was dissolved in methylene chloride (30 mL) and 3-chloroperbenzoic acid (77%, 6.33 g, 28.2 mmol, 2) was added in one portion. After 6 hr, another additional 3-chloroperbenzoic acid (3.15 g, 14.10 mmol) was added, and the reaction was stirred at rt overnight. LC/MS indicated that the starting material was consumed and the N-oxide present. The reaction mixture was diluted with methylene chloride (200 mL) and was washed with $Na_2CO_3$ (saturated aqueous solution, 100 mL) and brine. The organics were dried over $Na_2SO_4$, filtered, and concentrated under reduced pressure. The material was purified by column chromatography (Biotage 70 g column, 5 to 50% EtOAc in hexanes gradient), yielding 3.90 g (75%) of the pure N-oxide as an off-white solid ($R_f$=0.33 in 66% EtOAc/hexanes). The N-oxide was dissolved in toluene (30 mL) and phosphorous oxybromide (6.36 g, 22.1 mmol) was added. The reaction mixture was heated to 80° C. After 1 hr, LC/MS indicated that the reaction was complete. Upon cooling to rt, the reaction mixture was poured into a solution of $K_2CO_3$ (10 g) in water (50 mL). This mixture was extracted with EtOAc (3×100 mL), and the combined extracts were dried over $Na_2SO_4$, filtered, and concentrated under reduced pressure. The resulting material was purified by column chromatography (Biotage 50 g column, 0 to 10% EtOAc in hexanes gradient), yielding 2.06 g (45%) of the desired product S1-9 as an oil which slowly solidified after standing overnight. In addition, 1.01 g (20%) intermediate S1-8 was recovered. $^1$H NMR (400 MHz, CDCl$_3$) δ 7.49-7.41 (m, 2H), 7.40-7.27 (m, 7H), 7.02 (d, J=8.2 Hz, 2H), 5.15 (s, 2H), 2.43 (s, 3H); MS (ESI) m/z 432.02, 434.02 (M+H).

Example 2

Preparation of phenyl 5-(benzyloxy)-2-methoxy-3-methylisonicotinate (S2-5)

S2-5, an intermediate useful in synthesizing compounds of the invention was prepared according to Scheme 2.

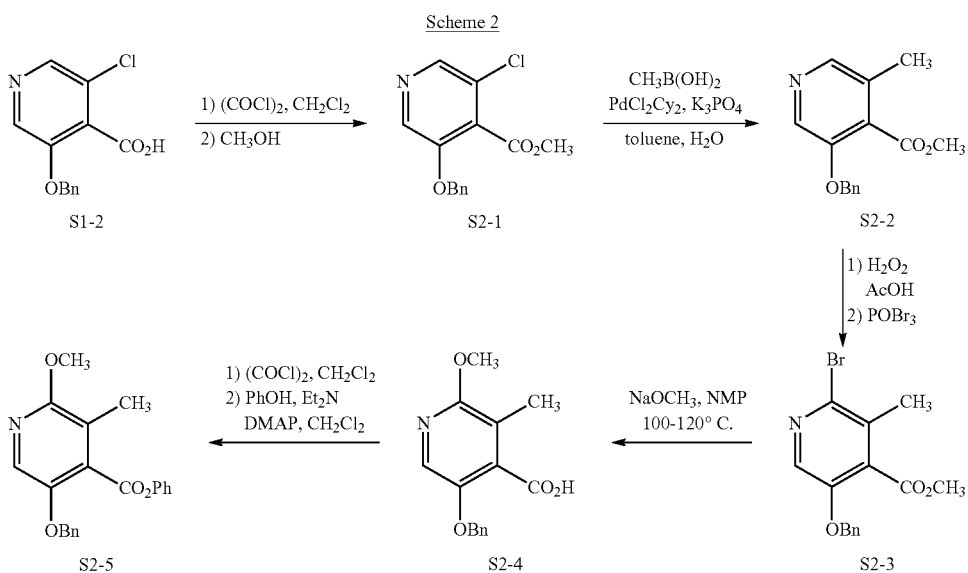

Scheme 2

Synthesis of S2-1

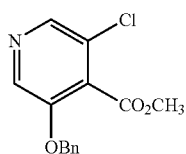

S2-1

Oxalyl chloride (6.6 mL, 76 mmol) was added to a suspension of S1-2 (5.00 g, 19.0 mmol) in CH$_2$Cl$_2$ (100 mL) over ~5 minutes. DMF was added drop wise in ~20 μL portions every 5 minutes until complete solution was achieved. After stirring for an additional 30 minutes, the reaction mixture was concentrated under reduced pressure. The resulting solid was dissolved in methanol (100 mL). After 3 h, the reaction mixture was concentrated under reduced pressure, yielding 6.2 g (>100% crude yield with some residual solvent) of the product as a tan solid. The material was used without purification. $^1$H NMR (400 MHz, DMSO-d6) δ 8.58 (s, 1H), 8.39 (s, 1H), 7.42-7.30 (m, 5H), 5.36 (s, 2H), 3.88 (s, 3H); MS (ESI) m/z 278.24 (M+H).

Synthesis of S2-2

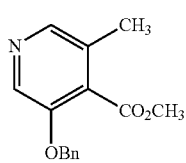

S2-2

The crude intermediate S2-1 (6.2 g, ≤19.0 mmol), methyl boronic acid (3.4 g, 57 mmol), dichlorobis(tricyclohexylphosphine)palladium(II) (326 mg, 0.95 mmol), and K$_3$PO$_4$ (12 g, 57 mmol) were heated to 100° C. in toluene (75 mL) and water (8 mL). After 16 hr, the reaction mixture was allowed to cool to rt and was diluted with EtOAc (100 mL). This was washed with water (100 mL) and brine (100 mL), dried over Na$_2$SO$_4$, filtered, and concentrated under reduced pressure. The material was purified by column chromatography (Biotage 50 g column, 0 to 50% EtOAc/hexanes gradient), yielding 3.99 g (82%) of the product as a thick oil. R$_f$=0.20 in 50% EtOAc/hexanes. $^1$H NMR (400 MHz, DMSO-d6) δ 8.37 (s, 1H), 8.16 (s, 1H), 7.42-7.28 (m, 5H), 5.27 (s, 2H), 3.84 (s, 3H), 2.19 (s, 3H); MS (ESI) m/z 258.27 (M+H).

Synthesis of S2-3

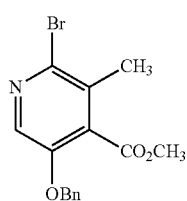

S2-3

Intermediate S2-2 (2.00 g, 7.77 mmol) was heated to 80° C. in acetic acid (10 mL) and hydrogen peroxide (30% aqueous solution, 10 mL). After 3 hr, LC/MS indicated that the starting material was consumed and the N-oxide present. The reaction mixture was concentrated under reduced pressure, diluted with EtOAc (50 mL), and washed with NaHCO$_3$ (saturated aqueous solution, 3×50 mL). The organics were dried over Na$_2$SO$_4$, filtered, and concentrated under reduced pressure. The material was dissolved in toluene (20 mL) and phosphorous oxybromide (4.46 g, 15.5 mmol) was added. The reaction mixture was heated to 80° C. After 30 minutes, LC/MS indicated the reaction was complete. Upon cooling to rt, the reaction mixture was poured into a solution of K$_2$CO$_3$ (25 g) in water (100 mL). Additional water (~50 mL) was used to transfer the remaining material in the reaction flask into the K$_2$CO$_3$ solution. This was extracted with EtOAc (3×100 mL), and the combined extracts were dried over Na$_2$SO$_4$, filtered, and concentrated under reduced pressure. The material was purified by column chromatography (Biotage 20 g column, 0 to 15% EtOAc/hexanes gradient), yielding 1.74 g (67%) of the product as an off-white solid. R$_f$=0.44 in 20% EtOAc/hexanes. 25:1 mixture of regioisomers by $^1$H-NMR. $^1$H NMR (400 MHz, DMSO-d6) δ 8.24 (s, 1H), 7.45-7.28 (m, 5H), 5.28 (s, 2H), 3.86 (s, 3H), 2.21 (s, 3H); MS (ESI) m/z 336.1, 338.1 (M+H).

Synthesis of S2-5

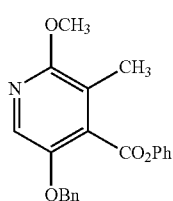

S2-5

Sodium methoxide (38 mg, 0.702 mmol) was added to a solution of intermediate S2-3 (118 mg, 0.351 mmol) in N-methylpyrrolidinone (2 mL), and the reaction mixture was heated to 100° C. After heating overnight, additional sodium methoxide (57 mg, 1.05 mmol) was added and heating was continued at 100° C. After 1 h, the reaction mixture was heated to 120° C. After an additional 1 h, the reaction mixture was cooled to rt, water (20 mL) was added, and the pH was adjusted to 2 with 6 N aqueous HCl. This was extracted with EtOAc (3×20 mL), and the combined extracts were dried over Na$_2$SO$_4$, filtered, and concentrated under reduced pressure. The crude acid intermediate was dissolved in CH$_2$Cl$_2$ (10 mL), and oxalyl chloride (0.123 mL, 1.40 mmol) was added After 1 h, the reaction mixture was concentrated under reduced pressure. The material was dissolved in CH$_2$Cl$_2$ (10 mL) and phenol (66 mg, 0.70 mmol), DMAP (4 mg, 0.035 mmol), and Et$_3$N (0.245 mL, 1.76 mmol) were added. After 1 hr, the reaction mixture was diluted with EtOAc (50 mL) and was washed with water (2×30 mL) and brine (30 mL). The organics were dried over Na$_2$SO$_4$, filtered, and concentrated under reduced pressure. The material was purified by column chromatography (Biotage 10 g column, 0 to 12% EtOAc in hexanes gradient), yielding 20.3 mg (17%) of clean product. An additional 29.1 mg of product contaminated with some residual phenol was also isolated. R$_f$=0.39 in 20% EtOAc/hexanes. $^1$H NMR (400 MHz, CDCl$_3$) δ 7.75 (s, 1H), 7.45-7.24 (m, 9H), 7.10 (d, J=7.3 Hz, 2H), 5.13 (s, 2H), 3.91 (s, 3H), 2.67 (s, 3H).

Example 3

Preparation of Compounds of Formula I, wherein X and Z are Simultaneously Hydrogen Compounds of Formula I, wherein X and Z are simultaneously hydrogen (as well as compounds of Formula II, wherein Z is hydrogen and compounds of Formula III, wherein X is hydrogen) were prepared according to Scheme 3.

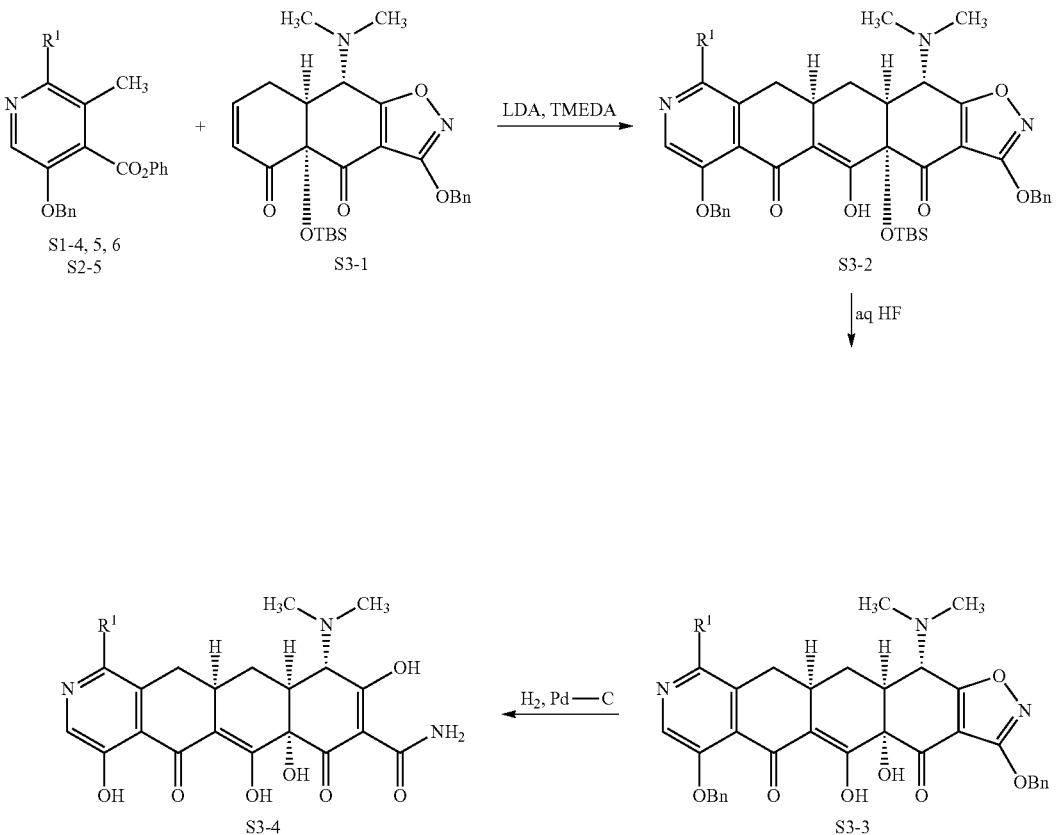

Specific intermediates and compounds of the invention prepared by Scheme 3 are set forth in detail below.

Synthesis of S3-2-1

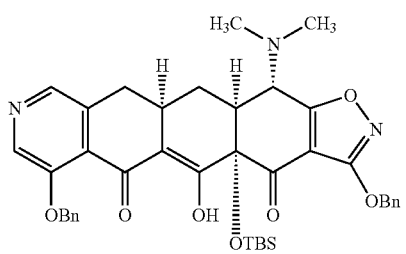

S3-2-1

Lithium diisopropylamide was prepared at −78° C. from n-butyllithium (1.6 M solution in hexane, 0.495 mL, 0.792 mmol) and diisopropylamine (0.112 mL, 0.792 mmol) in THF (5 mL). TMEDA (0.318 mL, 2.11 mmol) was added, followed by drop wise addition of a solution of intermediate S1-4 (169 mg, 0.529 mmol) in THF (2 mL). This resulted in a deep red colored solution. After 5 min, a solution of S3-1 (128 mg, 0.264 mmol) in THF (2 mL) was added. After complete addition, the reaction mixture was allowed to warm to −10° C. over 1 h. The reaction was quenched by the addition of ammonium chloride (saturated, aqueous solution, 20 mL) and was extracted with EtOAc (2×20 mL). The combined extracts were dried over $Na_2SO_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 80→100% B; mass-directed fraction collection], yielding 65.5 mg (35%) of the desired product S3-2-1 as a yellow solid. $^1H$ NMR (400 MHz, $CDCl_3$) δ 15.77 (s, 1H), 8.36 (s, 1H), 8.16 (s, 1H), 7.55-7.24 (m, 10H), 5.40-5.25 (m, 4H), 3.93 (d, J=11.0 Hz, 1H), 3.16-3.04 (m, 1H), 2.98-2.90 (m, 1H), 2.76-2.64 (m, 1H), 2.60-2.40 (m, 8H), 2.12 (d, J=14 Hz, 1H), 0.82 (s, 9H), 0.26 (s, 3H), 0.13 (s, 3H); MS (ESI) m/z 708.72 (M+H).

Compound 102

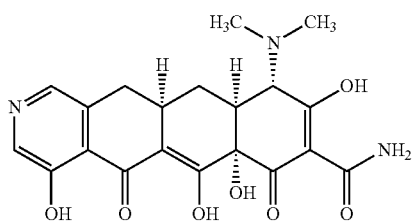

Compound 102

Aqueous HF (0.4 mL, 48%) was added to a solution of S3-2-1 (65.5 mg, 0.093 mmol) in $CH_3CN$ (0.6 mL) in a plastic vial. After 18 h, the reaction mixture was poured into a solution of $K_2HPO_4$ (4.8 g) in water (20 mL). The mixture was extracted with EtOAc (3×20 mL). The combined EtOAc extracts were dried over $Na_2SO_4$, filtered and concentrated under reduced pressure. The material was dissolved in methanol (1 mL) and 1,4-dioxane (1 mL), and palladium on carbon (Degussa, 10 wt %, ~5 mg) was added. An atmosphere of hydrogen was introduced, and the reaction mixture was stirred for 2 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 18.4 mg (41%, 2 steps) of the desired product Compound 102 as a yellow solid. $^1H$ NMR (400 MHz, $CD_3OD$ with 1 drop DCl) δ 8.55 (s, 1H), 8.36 (s, 1H), 4.19 (s, 1H), 3.26-2.98 (m, 9H), 2.71 (t, J=14.2 Hz, 1H), 2.39-2.32 (m, 1H), 1.75-1.63 (m, 1H); MS (ESI) m/z 416.44 (M+H).

Synthesis of S3-2-2

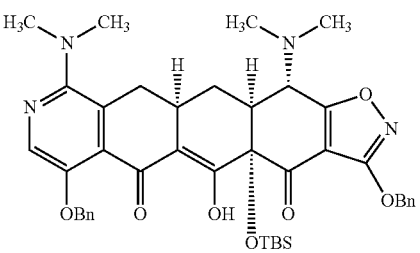

S3-2-2

A solution of intermediate S3-1-6 (412 mg, 1.14 mmol) in THF (1 mL) was added drop wise to a −78° C. solution of lithium diisopropylamide (10 wt % suspension in hexanes, 2.55 mL, 1.70 mmol) and TMEDA (0.684 mL, 4.54 mmol) in THF (10 mL), resulting in a reddish orange colored solution. After 10 min, a solution of S3-1 (274 mg, 0.568 mmol) in THF (1 mL) was added drop wise. The color gradually lightened to orange. After complete addition, the reaction mixture was allowed to warm to 0° C. over 1 h. The reaction was quenched by the addition of ammonium chloride (saturated, aqueous solution), was diluted with water, and was extracted with EtOAc (3×). The combined extracts were dried over $Na_2SO_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 80→100% B; mass-directed fraction collection], yielding 211 mg (50%) of the desired product S3-2-2 as a yellow solid. $^1H$ NMR (400 MHz, $CDCl_3$) δ 15.65 (s, 1H), 8.01 (s, 1H), 7.52-7.22 (m, 10H), 5.36 (s, 2H), 5.17 (q, J=11.0 Hz, 2H), 4.02 (d, J=11.0 Hz, 1H), 3.05 (dd, J=17.2 Hz, J=11.6 Hz, 1H), 2.98-2.86 (m, 1H), 2.73 (s, 6H), 2.62-2.38 (m, 9H), 2.12 (d, J=13.4 Hz, 1H), 0.81 (s, 9H), 0.26 (s, 3H), 0.13 (s, 3H); MS (ESI) m/z 751.79 (M+H).

Compound 109

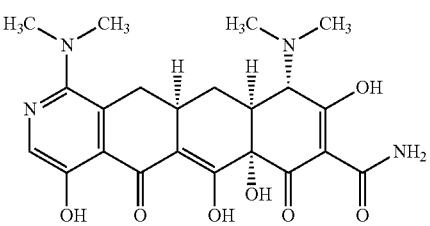

Compound 109

Aqueous HF (1.3 mL, 48%) was added to a solution of S3-2-2 (211 mg, 0.281 mmol) in CH₃CN (1.3 mL) in a plastic vial. After 18 h, the reaction mixture was poured into a solution of K₂HPO₄ (15.6 g) in water (50 mL). The mixture was extracted with EtOAc (3×50 mL). The aqueous layer was diluted with brine (25 mL) and was extracted with EtOAc (2×75 mL). The combined EtOAc extracts were dried over Na₂SO₄, filtered and concentrated under reduced pressure. The material was dissolved in methanol (5 mL) and 1,4-dioxane (5 mL), and palladium on carbon (Degussa, 10 wt %, ~30 mg) was added. An atmosphere of hydrogen was introduced, and the reaction mixture was stirred for 1 h. The reaction mixture was filtered through Celite, and the filtrate was concentrated under reduced pressure. The material was purified on a Waters Autopurification system equipped with a Phenomenex Polymerx 10µ RP 100 A column [10 µm, 30×21.20 mm; flow rate, 20 mL/min; Solvent A: 0.05 N HCl in water; Solvent B: CH₃CN; gradient: 10→100% B; mass-directed fraction collection]. Fractions with the desired MW were collected and freeze-dried to yield 142 mg (96%, 2 steps) of the desired product Compound 109 as a yellow solid. ¹H NMR (400 MHz, CD₃OD with 1 drop DCl) δ 8.22 (s, 1H), 4.19 (s, 1H), 3.38-3.30 (m, 2H), 3.24 (s, 6H), 3.12-2.95 (m, 7H), 2.60 (t, J=14.2 Hz, 1H), 2.42-2.34 (m, 1H), 1.75-1.63 (m, 1H); MS (ESI) m/z 459.50 (M+H).

Synthesis of S3-2-3

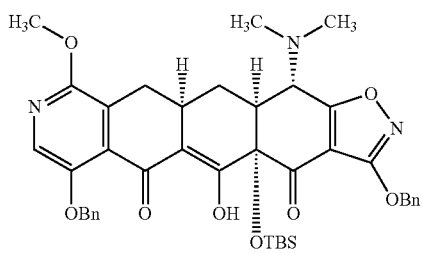

S3-2-3

A solution of intermediate S2-5 (20.3 mg, 0.058 mmol) in THF (1 mL) was added drop wise to a −78° C. solution of lithium diisopropylamide (1.8 M solution in hexanes, 0.050 mL, 0.090 mmol) and TMEDA (0.022 mL, 0.15 mmol) in THF (2 mL). After 10 min, a solution of S3-1 (14 mg, 0.029 mmol) in THF (0.5 mL) was added. After complete addition, the reaction mixture was allowed to warm to 0° C. over 1 h. LC/MS indicated a lot of S2-5 and S3-1 remained. The reaction mixture was again cooled to −78° C., and additional lithium diisopropylamide (1.8 M solution in hexanes, 0.050 mL, 0.090 mmol) was added. This was allowed to warm to 0° C. over 30 min. The reaction was quenched by the addition of ammonium chloride (saturated, aqueous solution, 20 mL), was diluted with water, and was extracted with EtOAc (3×20 mL). The combined extracts were dried over Na₂SO₄, filtered, and concentrated under reduced pressure. The material was purified on a Waters Autopurification system equipped with a Sunfire Prep C18 OBD column [5 µm, 19×50 mm; flow rate, 20 mL/min; Solvent A: H₂O with 0.1% HCO₂H; Solvent B: CH₃CN with 0.1% HCO₂H; gradient: 80→100% B; mass-directed fraction collection], yielding 5.9 mg (27%) of the desired product S3-2-3 as a yellow solid. ¹H NMR (400 MHz, CDCl₃) δ 15.70 (s, 1H), 7.83 (s, 1H), 7.55-7.24 (m, 10H), 5.36 (s, 2H), 5.17 (q, J=13.4 Hz, 2H), 3.98 (d, J=11.0 Hz, 1H), 3.72 (s, 3H), 3.18 (d, J=16.5 Hz, 1H), 3.04-2.96 (m, 1H), 2.60-2.30 (m, 9H), 2.15 (d, J=14 Hz, 1H), 0.82 (s, 9H), 0.26 (s, 3H), 0.13 (s, 3H); MS (ESI) m/z 738.66 (M+H).

Compound 121

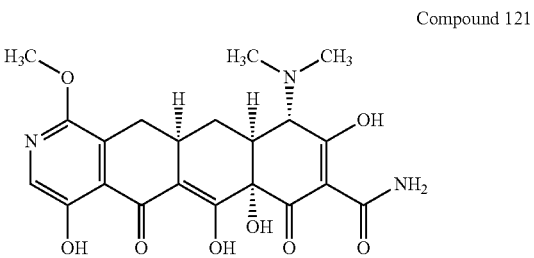 [SMILES: COc1ncc(O)c2c1C[C@H]1C[C@H]3[C@H](N(C)C)C(O)=C(C(N)=O)C(=O)[C@@]3(O)C(O)=C1C2=O]

Compound 121

Aqueous HF (0.4 mL, 48%) was added to a solution of S3-2-3 (5.9 mg, 0.008 mmol) in CH₃CN (0.4 mL) in a plastic vial. After 18 h, the reaction mixture was poured into a solution of K₂HPO₄ (4.8 g) in water (20 mL). The mixture was extracted with EtOAc (3×20 mL). The combined EtOAc extracts were dried over Na₂SO₄, filtered and concentrated under reduced pressure. The material was dissolved in methanol (1 mL) and 1,4-dioxane (1 mL), and palladium on carbon (Degussa, 10 wt %, ~5 mg) was added. An atmosphere of hydrogen was introduced, and the reaction mixture was stirred for 1 h. The reaction mixture was filtered through Celite, and the filtrate was concentrated under reduced pressure. The material was purified on a Waters Autopurification system equipped with a Phenomenex Polymerx 10µ RP 100 A column [10 µm, 30×21.20 mm; flow rate, 20 mL/min; Solvent A: 0.05 N HCl in water; Solvent B: CH₃CN; gradient: 10→100% B; mass-directed fraction collection]. Fractions with the desired MW were collected and freeze-dried to yield 2.1 mg (51%, 2 steps) of the desired product Compound 121 as a yellow solid. ¹H NMR (400 MHz, CD₃OD with 1 drop DCl) δ 7.80 (s, 1H), 4.15 (s, 1H), 3.97 (s, 3H), 3.40-2.98 (m, 9H), 2.32-2.20 (m, 2H), 1.72-1.56 (m, 1H); MS (ESI) m/z 446.39 (M+H).

Example 4

Preparation of Additional Compounds of Formula I, wherein X and Z are Simultaneously Hydrogen Additional compounds of Formula I, wherein X and Z are simultaneously hydrogen (as well as compounds of Formula II, wherein Z is hydrogen and compounds of Formula III, wherein X is hydrogen) were prepared according to Scheme 4.

Scheme 4

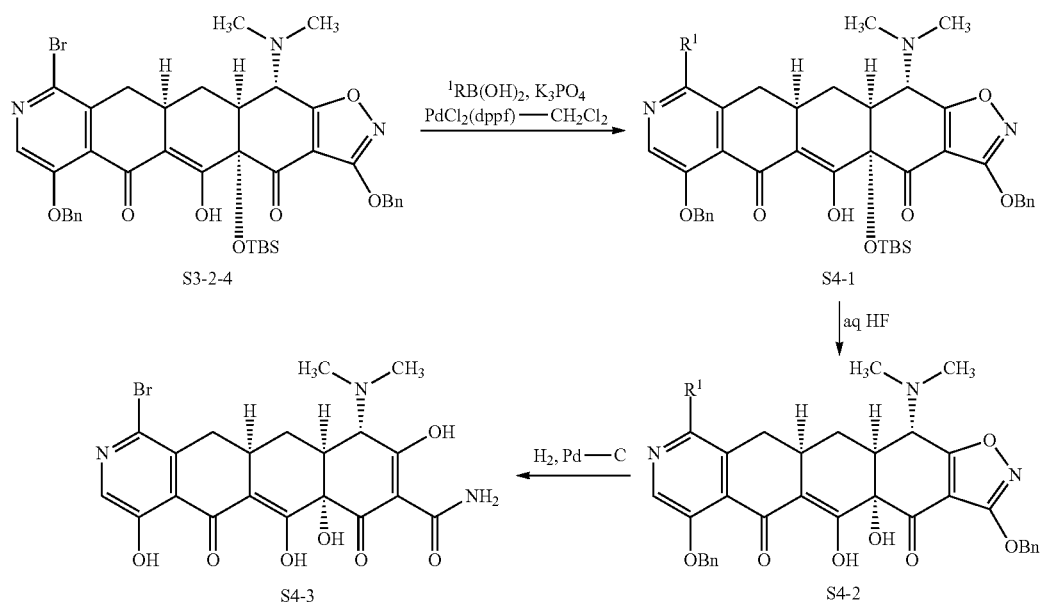

Synthesis of S3-2-4

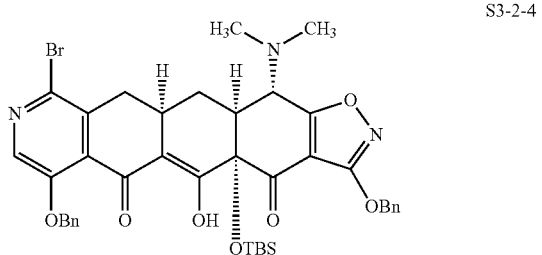 [SMILES: CN(C)[C@@H]1c2onc(OCc3ccccc3)c2C(=O)[C@@]2(O[Si](C)(C)C(C)(C)C)C(O)=C3C(=O)c4c(OCc5ccccc5)cnc(Br)c4C[C@H]3C[C@@H]12]

S3-2-4

Lithium diisopropylamide was prepared at −78° C. from n-butyllithium (1.6 M solution in hexane, 0.850 mL, 1.36 mmol) and diisopropylamine (0.192 mL, 1.36 mmol) in THF (10 mL). TMEDA (0.546 mL, 3.63 mmol) was added, followed by drop wise addition of a solution of intermediate S1-5 (361 mg, 0.907 mmol) in THF (3.5 mL). This resulted in a deep red colored solution. After 5 min, a solution of S3-1 (219 mg, 0.0.454 mmol) in THF (1 mL) was added. After complete addition, the reaction mixture was allowed to warm to 0° C. over 1.5 h. The reaction was quenched by the addition of ammonium chloride (saturated, aqueous solution) and was extracted with EtOAc (3×). The combined extracts were dried over Na$_2$SO$_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 80→100% B; mass-directed fraction collection], yielding 252 mg (71%) of the desired product S3-2-4 as a yellow solid. $^1$H NMR (400 MHz, CDCl$_3$) δ 15.55 (s, 1H), 8.12 (s, 1H), 7.55-7.24 (m, 10H), 5.40-5.22 (m, 4 μl), 3.90 (d, J=11.0 Hz, 1H), 3.25 (dd, J=16.5 Hz, J=4.88 Hz, 1H), 3.12-3.02 (m, 1H), 2.62-2.42 (m, 9H), 2.14 (d, J=14.0 Hz, 1H), 0.82 (s, 9H), 0.26 (s, 3H), 0.13 (s, 3H); MS (ESI) m/z 786.63, 788.63 (M+H).

Specific intermediates and compounds of the invention prepared using S3-2-4 according to Scheme 4 are set forth in detail below.

Synthesis of S4-1-1

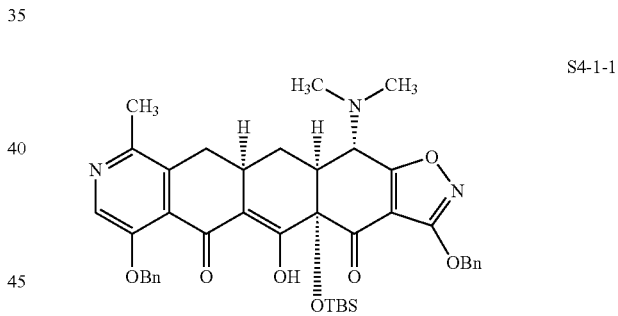

S4-1-1

A solution of intermediate S3-2-4 (52.5 mg, 0.067 mmol), methylboronic acid (40 mg, 0.67 mmol), dichloro[1,1'-bis (diphenylphosphino)-ferrocene]palladium(II) methylene chloride adduct (3 mg, 0.003 mmol) and potassium phosphate (142 mg, 0.667 mmol) in toluene (1 mL), 1,4-dioxane (1 mL), and water (0.2 mL) was heated to 70° C. After 2 h, the reaction mixture was heated to 100° C. After an additional 2 h, the reaction mixture was diluted with EtOAc (20 mL) and was washed with water (15 mL) and brine (15 mL). The organics were dried over Na$_2$SO$_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 80→100% B; mass-directed fraction collection], yielding 18.3 mg (38%) of the desired product S4-1-1 as a yellow solid. $^1$H NMR (400 MHz, CDCl$_3$) δ 15.71 (s, 1H), 8.24 (s, 1H), 7.55-7.24 (m, 10H), 5.36 (s, 2H), 5.30-5.20 (m, 2H), 3.95 (d, J=10.4 Hz, 1H), 3.10-2.92 (m, 2H), 2.62-2.42 (m, 12H), 2.12 (d, J=14.0 Hz, 1H), 0.82 (s, 9H), 0.26 (s, 3H), 0.14 (s, 3H); MS (ESI) m/z 722.72 (M+H).

Compound 152

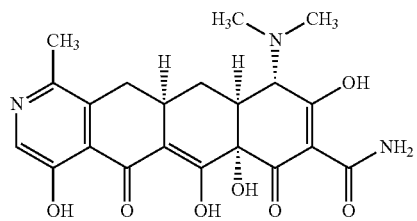

Compound 152

Aqueous HF (0.4 mL, 48%) was added to a solution of S4-1-1 (18.3 mg, 0.025 mmol) in $CH_3CN$ (0.6 mL) in a plastic vial. After 18 h, the reaction mixture was poured into a solution of $K_2HPO_4$ (4.8 g) in water (20 mL). The mixture was extracted with EtOAc (3×20 mL). The combined EtOAc extracts were dried over $Na_2SO_4$, filtered and concentrated under reduced pressure. The material was dissolved in methanol (2 mL) and 1,4-dioxane (2 mL), and palladium on carbon (Degussa, 10 wt %, ~5 mg) was added. An atmosphere of hydrogen was introduced, and the reaction mixture was stirred for 1 h. The reaction mixture was filtered through Celite, and the filtrate was concentrated under reduced pressure. The material was purified on a Waters Autopurification system equipped with a Phenomenex Polymerx 10μ RP 100A column [10 μm, 30×21.20 mm; flow rate, 20 mL/min; Solvent A: 0.05 N HCl in water; Solvent B: $CH_3CN$; gradient: 0→4100% B; mass-directed fraction collection]. Fractions with the desired MW were collected and freeze-dried to yield 4.3 mg (34%, 2 steps) of the desired product Compound 152 as a yellow solid. $^1$H NMR (400 MHz, $CD_3OD$ with 1 drop DCl) δ 8.35 (s, 1H), 4.19 (s, 1H), 3.25-2.95 (m, 9H), 2.80-2.25 (m, 5H), 1.80-1.63 (m, 1H); MS (ESI) m/z 430.46 (M+H).

Synthesis of S4-1-2

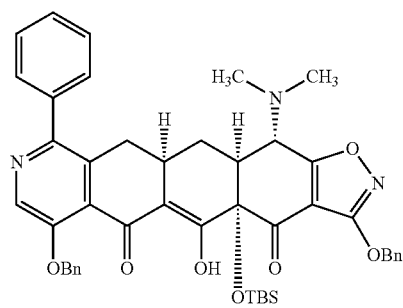

S4-1-2

A solution of intermediate S3-2-4 (31.6 mg, 0.040 mmol), phenylboronic acid (24.5 mg, 0.201 mmol), dichloro[1,1'-bis(diphenylphosphino)-ferrocene]palladium(II) methylene chloride adduct (1.6 mg, 0.002 mmol) and sodium carbonate (21.3 mg, 0.201 mmol) in toluene (1 mL), 1,4-dioxane (1 mL), and water (0.2 mL) was heated to 100° C. via microwave reactor for 10 min. The reaction mixture was diluted with EtOAc (10 mL) and was washed with water (5 mL) and brine (5 mL). The organics were dried over $Na_2SO_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 80→100% B; mass-directed fraction collection], yielding 16.9 mg (54%) of the desired product S4-1-2 as a yellow solid. $^1$H NMR (400 MHz, $CDCl_3$) δ 15.66 (s, 1H), 8.48 (s, 1H), 7.52-7.24 (m, 15H), 5.42-5.30 (m, 4H), 3.97 (d, J=10.4 Hz, 1H), 3.00-2.86 (m, 2H), 2.78-2.62 (m, 1H), 2.58-2.30 (m, 8H), 2.00 (d, J=14.0 Hz, 1H), 0.80 (s, 9H), 0.25 (s, 3H), 0.14 (s, 3H); MS (ESI) m/z 784.75 (M+H).

Compound 160

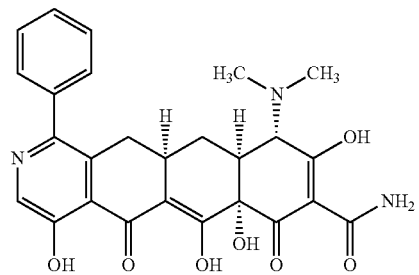

Compound 160

Aqueous HF (0.4 mL, 48%) was added to a solution of S4-1-2 (12.2 mg, 0.0156 mmol) in $CH_3CN$ (0.6 mL) in a plastic vial. After 18 h, the reaction mixture was poured into a solution of $K_2HPO_4$ (4.8 g) in water (20 mL). The mixture was extracted with EtOAc (3×20 mL). The combined EtOAc extracts were dried over $Na_2SO_4$, filtered and concentrated under reduced pressure. The material was dissolved in methanol (2 mL) and 1,4-dioxane (2 mL), and palladium on carbon (Degussa, 10 wt %, ~5 mg) was added. An atmosphere of hydrogen was introduced, and the reaction mixture was stirred for 2 h. The reaction mixture was filtered through Celite, and the filtrate was concentrated under reduced pressure. The material was purified on a Waters Autopurification system equipped with a Phenomenex Polymerx 10μ RP 100A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 2.1 mg (24%, 2 steps) of the desired product Compound 160 as a yellow solid. $^1$H NMR (400 MHz, $CD_3OD$ with 1 drop DCl) δ 8.53 (s, 1H), 7.62 (s, 5H), 4.18 (s, 1H), 3.14-2.82 (m, 9H), 2.81-2.66 (m, 1H), 2.24-2.14 (m, 1H), 1.66-1.52 (m, 1H); MS (ESI) m/z 492.48 (M+H).

Example 5

Preparation of Compounds of Formula I, wherein X is Hydrogen, Y is Cl or Hydrogen and Z is —N($R^3$)($R^4$)

Compounds of Formula I, wherein X is hydrogen, Y is Cl or hydrogen, and Z is —N($R^3$)($R^4$) (as well as compounds of Formula II, wherein Z is —N($R^3$)($R^4$)) were prepared according to Scheme 5.

Scheme 5

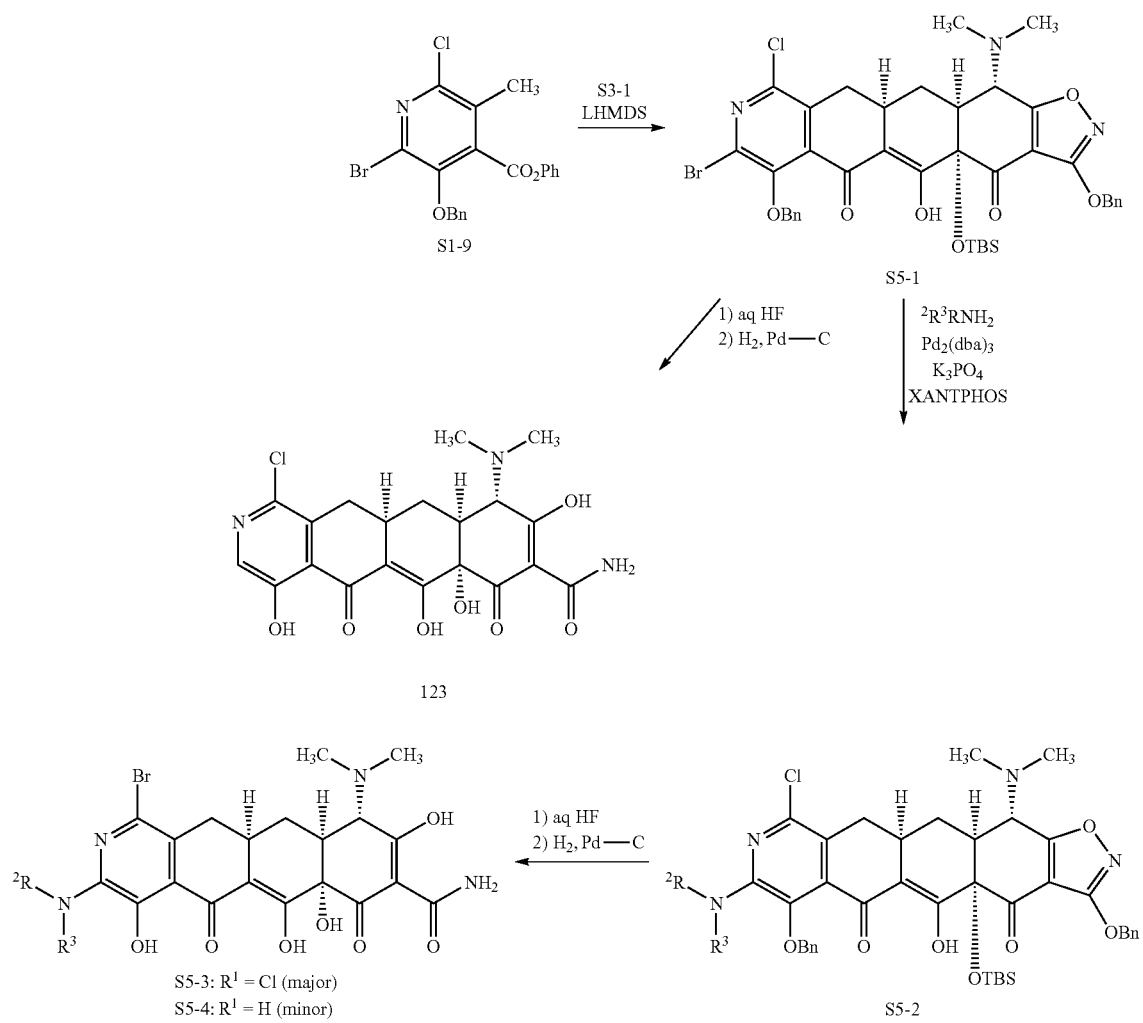

The following specific intermediates and compounds of the invention were prepared according to Scheme 5.

Synthesis of S5-1

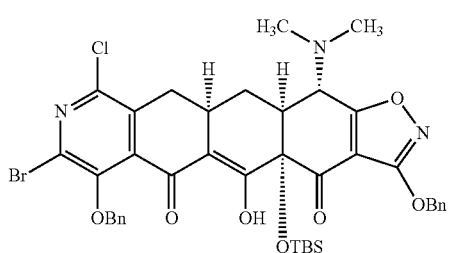

Intermediate S1-9 (793 mg, 1.84 mmol) and S3-1 (885 mg, 1.84 mmol, 1.0 eq) were dissolved in THF (anhydrous, 16 mL) under a nitrogen atmosphere in a flame-dried Schlenck flask. The resulting solution was cooled to −78° C. in a dry ice/acetone bath. LHMDS solution (1.0 M, 5.51 mL, 3.0 equiv) was added slowly via syringe. After 10 min, LC/MS indicated that the starting material was consumed and the product present. The reaction mixture was allowed to slowly warm to 0° C. over 1 hr. A phosphate buffer solution (pH 7.0, 20 mL) was added, followed by the addition of ammonium chloride (saturated, aqueous solution, 50 mL). The resulting mixture was extracted with methylene chloride (3×50 mL), and the combined extracts were dried over $Na_2SO_4$, filtered, and concentrated under reduced pressure. The resulting brown solid was washed with cold methanol (3×5 mL) to afford the desired product S5-1 as a yellow-brown powder (1.11 g, 74%). The organics were concentrated under reduced pressure and purified by column chromatography (Biotage 20 g column, 5 to 20% EtOAc in hexanes gradient), yielding another 150 mg (10%) of intermediate S5-1. $^1$H NMR (400 MHz, $CDCl_3$) δ 15.45 (br, 1H), 7.54-7.48 (m, 4H), 7.40-7.30 (m, 6H), 5.36 (s, 2H), 5.03 (abq, J=10.4 Hz, 2H), 3.87 (d, J=11.0 Hz, 1H), 3.27-3.23 (m, 1H), 3.10-3.00 (m, 1H), 2.65-

2.57 (m, 1H), 2.57-2.43 (m, 8H), 2.16 (d, J=11.0 Hz, 1H), 0.81 (s, 9H), 0.26 (s, 3H), 0.12 (s, 3H); MS (ESI) m/z 820.37, 822.37 (M+H).

Synthesis of S5-2-1

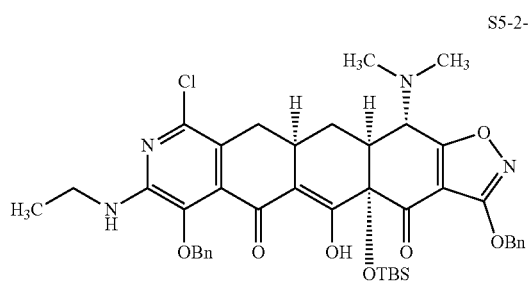

S5-2-1

Intermediate S5-1 (50 mg, 0.061 mmol), K₃PO₄ (39 mg, 0.18 mmol, 3.0 equiv), tris(dibenzylideneacetone)dipalladium (2.8 mg, 0.003 mmol, 5 mol %) and 9,9-dimethyl-4,5-bis-(diphenylphosphino)xanthene (5.1 mg, 0.009 mmol, 15 mol %) were added to a small vial equipped with a septa. After the flask was evacuated and flushed with nitrogen 3 times, 0.5 mL anhydrous dioxane was added, followed by the addition of ethylamine (2.0 M/THF, 0.091 mL, 0.18 mmol, 3 equiv). The reaction mixture was heated to 100° C. and stirred for 3 hr. LC/MS indicated that the starting material was about 40% consumed and the product present. The reaction mixture was allowed to cool to rt and was filtered through a small Celite pad. The crude black oil was purified on a Waters Autopurification system equipped with a Sunfire Prep C18 OBD column [5 µm, 19×50 mm; flow rate, 20 mL/min; Solvent A: H₂O with 0.1% HCO₂H; Solvent B: CH₃CN with 0.1% HCO₂H; gradient: 90→100% B; mass-directed fraction collection]. The fractions with the desired MW were collected and freeze-dried to yield 11 mg (23%) of the desired product S5-2-1 as a yellow solid: ¹H NMR (400 MHz, CCl₃D) δ 15.6 (br, 1H), 7.56-7.49 (m, 4H), 7.42-7.30 (m, 6H), 5.37 (s, 2H), 5.03 (s, 2H), 3.89 (d, J=11.0 Hz, 1H), 3.24-3.04 (m, 3H), 2.97 (dd, J=15.6, 4.9 Hz, 1H), 2.64-2.43 (m, 3H), 2.49 (s, 6H), 2.14 (d, J=15.6 Hz, 1H), 1.25 (t, J=6.8 Hz, 3H), 0.81 (s, 9H), 0.25 (s, 3H), 0.11 (s, 3H); MS (ESI) m/z 785.57 (M+H).

Compound 110

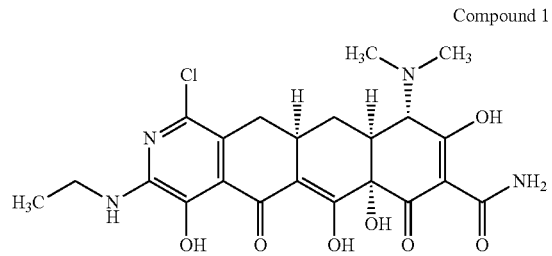

Compound 110

Aqueous HF (0.3 mL, 48%) was added to a solution of S5-2-1 (11 mg, 0.014 mmol) in CH₃CN (7 mL) in a plastic vial. After 18 h, the reaction mixture was poured into a solution of K₂HPO₄ (2 g) in water (10 mL). The mixture was extracted with EtOAc (3×). The combined EtOAc extracts were dried over Na₂SO₄ and concentrated under reduced pressure. The material was dissolved in methanol (2 mL) and dioxane (2 mL), and palladium on carbon (Degussa, 10 wt %, 5.6 mg) was added. An atmosphere of hydrogen was introduced, and the reaction mixture was stirred for 1 h. The reaction mixture was filtered through a small Celite pad, and the filtrate was concentrated under reduced pressure. The material was purified on a Waters Autopurification system equipped with a Phenomenex Polymerx 10µ RP 100 A column [10 µm, 30×21.20 mm; flow rate, 20 mL/min; Solvent A: 0.05 N HCl in water; Solvent B: CH₃CN; gradient: 0→100% B; mass-directed fraction collection]. Fractions with the desired MW were collected and freeze-dried to yield 3.2 mg (46%, 2 steps) of the desired product Compound 110 as a yellow solid. ¹H NMR (400 MHz, CD₃OD) δ 4.08 (s, 1H), 3.43 (q, J=7.4 Hz, 2H), 3.08-2.92 (m, 9H), 2.30-2.15 (m, 2H), 1.67-1.55 (m, 1H), 1.22 (t, J=7.4 Hz, 3H); MS (ESI) m/z 493.24 (M+H).

The following compounds were prepared according to the methods of Compound 110, substituting the appropriate amine for ethylamine:

Compound 156

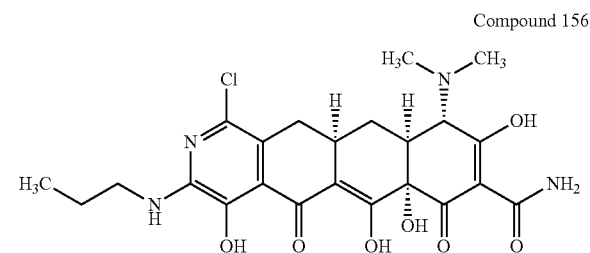 [SMILES: CCCNc1nc(Cl)c2c(c1O)C(=O)C1=C(O)[C@]3(O)C(=O)C(C(N)=O)=C(O)[C@@H](N(C)C)[C@@H]3C[C@@H]1C2]

Compound 156

¹H NMR (400 MHz, CD₃OD with 1 drop DCl) δ 4.16 (s, 1H), 3.47 (t, J=7.3 Hz, 2H), 3.15-2.96 (m, 9H), 2.32-2.20 (m, 2H), 1.78-1.55 (m, 3H), 1.01 (t, J=7.4 Hz, 3H); MS (ESI) m/z 507.29 (M+H).

Compound 112

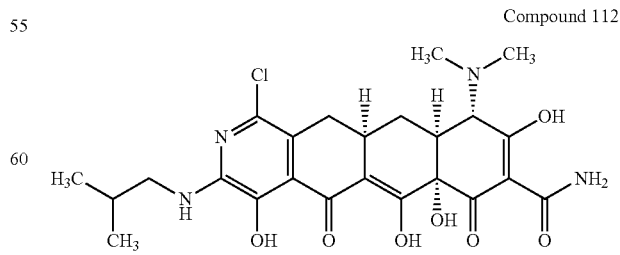

Compound 112

¹H NMR (400 MHz, CD₃OD with 1 drop DCl) δ 4.18 (s, 1H), 3.38 (d, J=7.3 Hz, 2H), 3.20-2.96 (m, 9H), 2.34-2.20 (m, 2H), 2.10-1.98 (m, 1H), 1.68-1.54 (m, 1H), 1.00 (d, J=6.4 Hz, 6H); MS (ESI) m/z 521.40 (M+H).

Compound 150

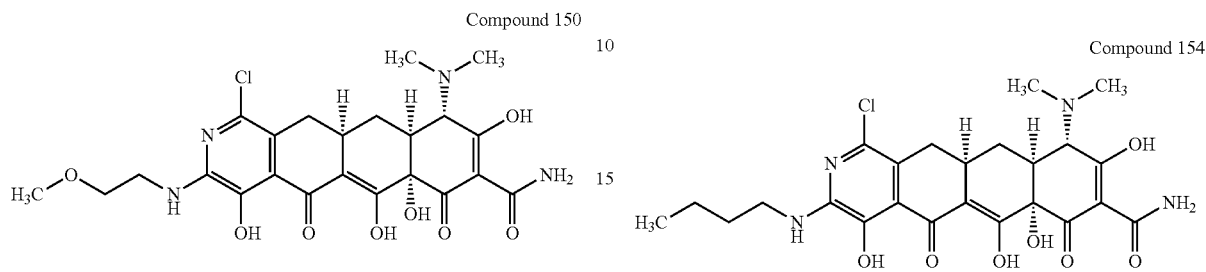

Compound 150

¹H NMR (400 MHz, CD₃OD with 1 drop DCl) δ 4.13 (s, 1H), 3.72-3.60 (m, 4H), 3.40 (s, 3H), 3.12-2.95 (m, 9H), 2.32-2.21 (m, 2H), 1.69-1.56 (m, 1H); MS (ESI) m/z 523.32 (M+H).

Compound 153

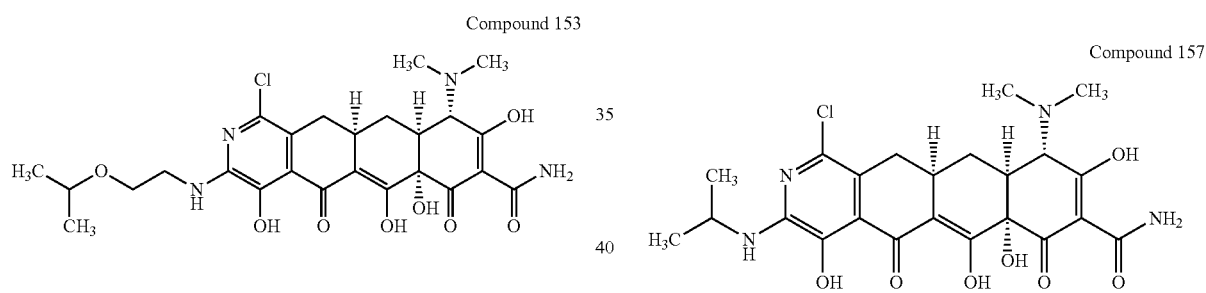

Compound 153

¹H NMR (400 MHz, CD₃OD with 1 drop DCl) δ 4.19 (s, 1H), 3.82-3.69 (m, 5H), 3.20-2.98 (m, 9H), 2.35-2.22 (m, 2H), 1.68-1.56 (m, 1H), 1.18 (d, J=6.4 Hz, 6H); MS (ESI) m/z 551.41 (M+H).

Compound 101

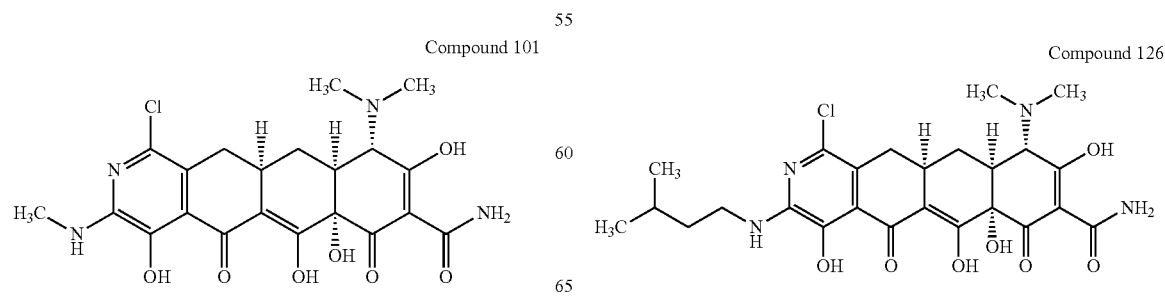

Compound 101

¹H NMR (400 MHz, CD₃OD) δ 4.08 (s, 1H), 3.41 (s, 3H), 3.08-2.92 (m, 9H), 2.30-2.15 (m, 2H), 1.67-1.55 (m, 1H); MS (ESI) m/z 479.22 (M+H).

Compound 154

Compound 154

¹H NMR (400 MHz, CD₃OD) δ 4.09 (s, 1H), 3.42-3.38 (m, 2H), 3.20 (s, 1H), 3.09-2.92 (m, 9H), 2.29-2.16 (m, 2H), 1.66-1.55 (m, 3H), 1.45-1.36 (m, 2H), 0.96 (t, J=7.3 Hz, 3H); MS (ESI) m/z 521.34 (M+H).

Compound 157

Compound 157

¹H NMR (400 MHz, CD₃OD) δ 4.21-4.13 (m, 1H), 4.08 (s, 1H), 3.14-2.92 (m, 9H), 2.31-2.15 (m, 2H), 1.67-1.56 (m, 1H), 1.23 (dd, J=6.4, 1.8 Hz, 6H); MS (ESI) m/z 507.24 (M+H).

Compound 126

Compound 126

¹H NMR (400 MHz, CD₃OD) δ 4.09 (s, 1H), 3.45-3.40 (m, 2H), 3.20 (s, 1H), 3.08-2.93 (m, 9H), 2.30-2.16 (m, 2H), 1.72-1.58 (m, 2H), 1.55-1.48 (m, 2H), 0.96 (d, J=6.4 Hz, 6H); MS (ESI) m/z 535.30 (M+H).

Compound 162

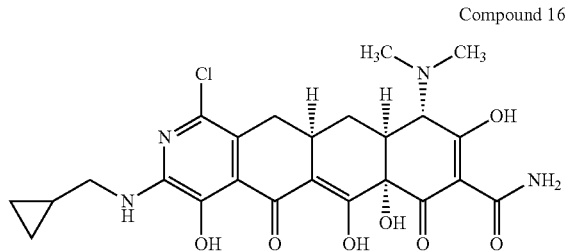

Compound 162

¹H NMR (400 MHz, CD₃OD) δ 4.16 (s, 1H), 3.47-3.42 (m, 2H), 3.11-2.93 (m, 9H), 2.32-2.19 (m, 2H), 1.67-1.57 (m, 1H), 1.19-1.14 (m, 1H), 0.79-0.73 (m, 2H), 0.48-0.42 (m, 2H); MS (ESI) m/z 519.30 (M+H).

Compound 115

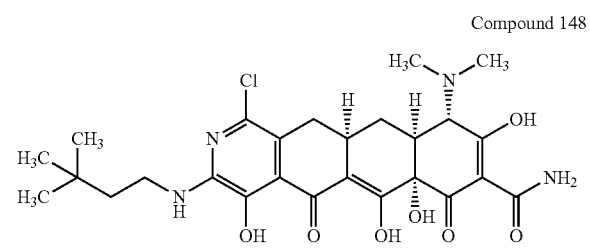 [SMILES: CN(C)[C@@H]1C(O)=C(C(N)=O)C(=O)[C@@]2(O)C(O)=C3C(=O)c4c(O)c(NCCC(C)(C)C)nc(Cl)c4C[C@H]3C[C@@H]12]

Compound 115

¹H NMR (400 MHz, CD₃OD) δ 4.12 (s, 1H), 3.41-3.37 (s, 2H), 3.14-2.93 (m, 9H), 2.34-2.20 (m, 2H), 1.68-1.57 (m, 1H), 1.06 (s, 9H); MS (ESI) m/z 535.34 (M+H).

Compound 148

¹H NMR (400 MHz, CD₃OD) δ 4.09 (s, 1H), 3.44-3.40 (m, 2H), 3.08-2.93 (m, 9H), 2.30-2.16 (m, 2H), 1.67-1.51 (m, 3H), 0.98 (s, 9H); MS (ESI) m/z 549.34 (M+H).

Compound 140

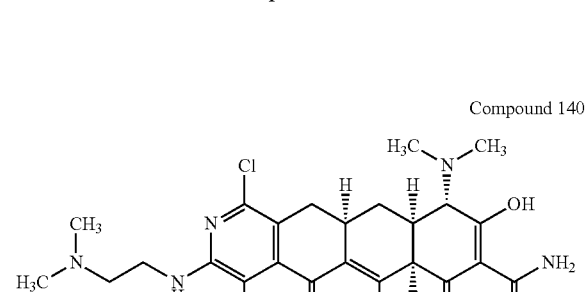

Compound 140

¹H NMR (400 MHz, CD₃OD) δ 4.13 (s, 1H), 3.84-3.77 (m, 2H), 3.44-3.38 (m, 2H), 3.10-2.92 (m, 15H), 2.32-2.20 (m, 2H), 1.68-1.55 (m, 1H); MS (ESI) m/z 536.25 (M+H).

Compound 119

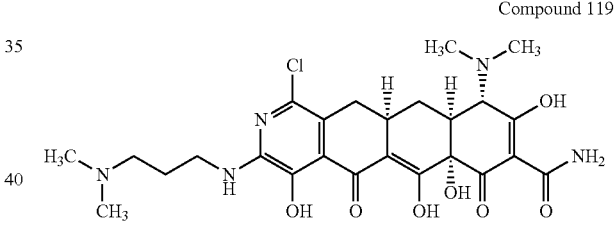

Compound 119

¹H NMR (400 MHz, CD₃OD) δ 4.09 (s, 1H), 3.70-3.46 (m, 4H), 3.10-2.90 (m, 15H), 2.31-2.17 (m, 2H), 2.10-2.00 (m, 2H), 1.68-1.56 (m, 1H); MS (ESI) m/z 550.34 (M+H).

Compound 134

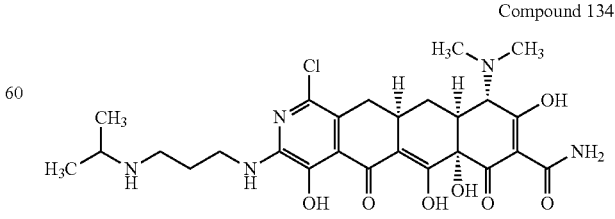

Compound 134

¹H NMR (400 MHz, CD₃OD) δ 4.09 (s, 1H), 3.58-3.50 (m, 1H), 3.12-2.92 (m, 13H), 2.30-2.17 (m, 2H), 2.04-1.95 (m, 2H), 1.67-1.55 (m, 1H), 1.33 (d, J=6.4 Hz, 6H); MS (ESI) m/z 564.39 (M+H).

Compound 124

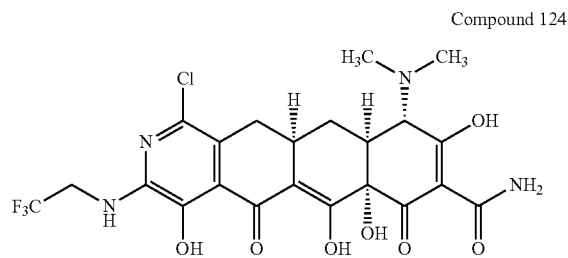 [SMILES: CN(C)[C@@H]1C(O)=C(C(N)=O)C(=O)[C@@]2(O)C(O)=C3C(=O)c4c(O)c(NCC(F)(F)F)nc(Cl)c4C[C@H]3C[C@@H]12]

Compound 124

¹H NMR (400 MHz, CD₃OD) δ 4.22-4.15 (m, 2H), 4.09 (s, 1H), 3.08-2.92 (m, 9H), 2.33-2.18 (m, 2H), 1.68-1.57 (m, 1H) MS (ESI) m/z 547.0 (M+H).

Compound 107

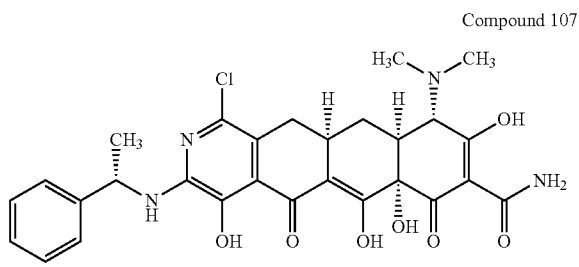 [SMILES: C[C@H](Nc1nc(Cl)c2c(c1O)C(=O)C1=C(O)[C@]3(O)C(=O)C(C(N)=O)=C(O)[C@@H](N(C)C)[C@@H]3C[C@@H]1C2)c1ccccc1]

Compound 107

¹H NMR (400 MHz, CD₃OD) δ 7.29 (d, J=8.2 Hz, 2H), 7.18 (t, J=7.2 Hz, 2H), 7.08 (t, J=7.2 Hz, 1H), 5.12-5.06 (m, 1H), 3.99 (s, 1H), 2.97-2.82 (m, 9H), 2.15-2.07 (m, 2H); 1.58-1.49 (m, 1H), 1.47 (d, J=7.6 Hz, 3H); MS (ESI) m/z 569.1 (M+H).

Compound 139

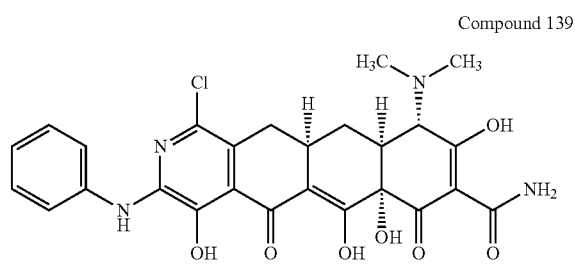 [SMILES: CN(C)[C@@H]1C(O)=C(C(N)=O)C(=O)[C@@]2(O)C(O)=C3C(=O)c4c(O)c(Nc5ccccc5)nc(Cl)c4C[C@H]3C[C@@H]12]

Compound 139

¹H NMR (400 MHz, CD₃OD) δ 7.77 (d, J=8.0 Hz, 2H), 7.31 (t, J=7.2 Hz, 2H), 7.01 (t, J=7.2 Hz, 1H), 4.11 (s, 1H), 3.16-2.95 (m, 9H), 2.41-2.19 (m, 2H), 1.70-1.60 (m, 1H); MS (ESI) m/z 541.1 (M+H).

Synthesis of S5-2-19

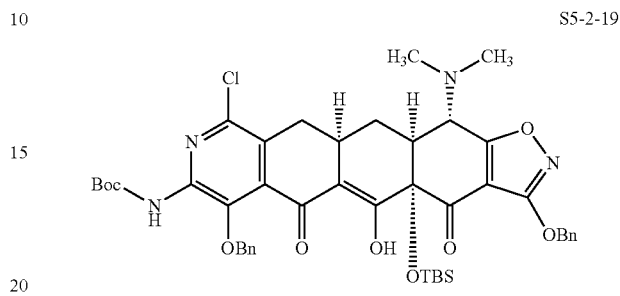

S5-2-19

Intermediate S5-1 (100 mg, 0.122 mmol), t-butylcarbamate (42.9 mg, 0.366 mmol), K₃PO₄ (77.7 mg, 0.366 mmol), tris(dibenzylideneacetone)-dipalladium (5.6 mg, 0.006 mmol) and 9,9-dimethyl-4,5-bis-(diphenylphosphino)-xanthene (10.3 mg, 0.018 mmol) were added to a vial equipped with a septum. After the flask was evacuated and flushed with nitrogen 3 times, 0.5 mL anhydrous dioxane was added. The reaction mixture was heated to 100° C. and stirred for 2 hr. The reaction mixture was allowed to cool to rt, was filtered through Celite, and was concentrated under reduced pressure. The material was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 80→100% B; mass-directed fraction collection]. The fractions with the desired MW were collected and freeze-dried to yield 41.7 mg (40%) of the desired product as a yellow solid.
¹H NMR (400 MHz, CDCl₃) δ 15.65-15.45 (br s, 1H), 7.56-7.50 (m, 2H), 7.43-7.34 (m, 7H), 7.29-7.20 (m, 1H), 5.38 (s, 2H), 4.94 (dd, J=29.3 Hz, J=11.0 Hz, 2H), 3.90 (d, J=11.0 Hz, 1H), 3.27 (dd, J=16.4 Hz, J=11.6 Hz, 1H), 3.12-3.03 (m, 1H), 2.68-2.60 (m, 1H), 2.60-2.45 (m, 8H), 2.18 (d, J=14.6 Hz, 1H), 1.47 (s, 9H), 0.85 (s, 9H), 0.29 (s, 3H), 0.15 (s, 3H); MS (ESI) m/z 857.67 (M+H).

Compound 147

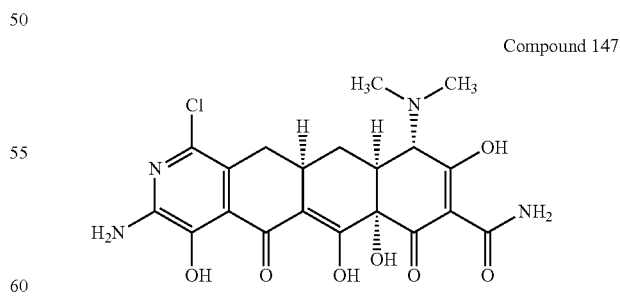

Compound 147

Aqueous HF (0.4 mL, 48%) was added to a solution of S5-2-19 (41.7 mg, 0.049 mmol) in CH₃CN (0.6 mL) in a plastic vial. After 18 h, the reaction mixture was poured into a solution of K₂HPO₄ (7.8 g) in water (15 mL). The mixture was extracted with EtOAc (3×). The combined EtOAc extracts were dried over Na₂SO₄ and concentrated under reduced pressure. The material was dissolved in methanol (1 mL) and dioxane (1 mL), and palladium on carbon (Degussa, 10 wt %, ~2 mg) was added. An atmosphere of hydrogen was introduced, and the reaction mixture was stirred for 3 h. The reaction mixture was filtered through a small Celite pad, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 17.7 mg (68%, 2 steps) of Compound 148 as a yellow solid. $^1$H NMR (400 MHz, $CD_3OD$ with 1 drop DCl) δ 4.19 (s, 1H), 3.20-2.98 (m, 8H), 2.35-2.22 (m, 2H), 1.68-1.56 (m, 1H); MS (ESI) m/z 465.32 (M+H).

intermediate. The reaction mixture was filtered through Celite, and the filtrate was concentrated under reduced pressure. Approximately half of the isolated intermediate was re-subjected to the hydrogenation conditions above. After 2 days, the reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 1.7 mg (18%, 2 steps) of Compound 147 as a yellow solid. $^1$H NMR (400 MHz, $CD_3OD$ with 1 drop DCl) δ 7.29 (s, 1H), 4.18 (s, 1H), 3.20-2.80 (m, 8H), 2.34-2.18 (m, 2H), 1.66-1.52 (m, 1H); MS (ESI) m/z 431.33 (M+H).

Compound 146

Compound 123

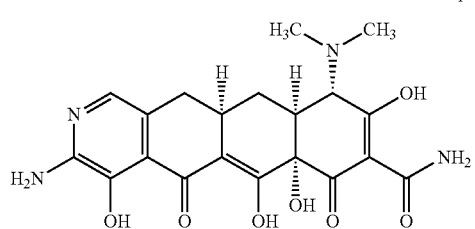

Compound 146

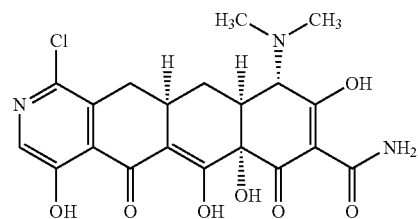

Compound 123

Aqueous HF (0.4 mL, 48%) was added to a solution of S5-2-19 (31.3 mg, 0.037 mmol) in $CH_3CN$ (0.6 mL) in a plastic vial. After 18 h, the reaction mixture was poured into a solution of $K_2HPO_4$ (7.8 g) in water (15 mL). The mixture was extracted with EtOAc (3×). The combined EtOAc extracts were dried over $Na_2SO_4$ and concentrated under reduced pressure. The material was dissolved in methanol (1 mL) and dioxane (1 mL), and palladium on carbon (Degussa, 10 wt %, ~10 mg) was added. An atmosphere of hydrogen was introduced, and the reaction mixture was stirred overnight. LC/MS indicated that the major product was the chlorinated Prepared from S5-1 by HF treatment and hydrogenation: $^1$H NMR (400 MHz, $CD_3OD$) δ 8.08 (d, J=6.0 Hz, 1H), 4.09 (s, 1H), 3.08-2.92 (m, 9H), 2.30-2.15 (m, 2H), 1.70-1.58 (m, 1H); MS (ESI) m/z 450.18 (M+H).

Example 6

Preparation of Compound 159

Compound 159 was prepared according to Scheme 6.

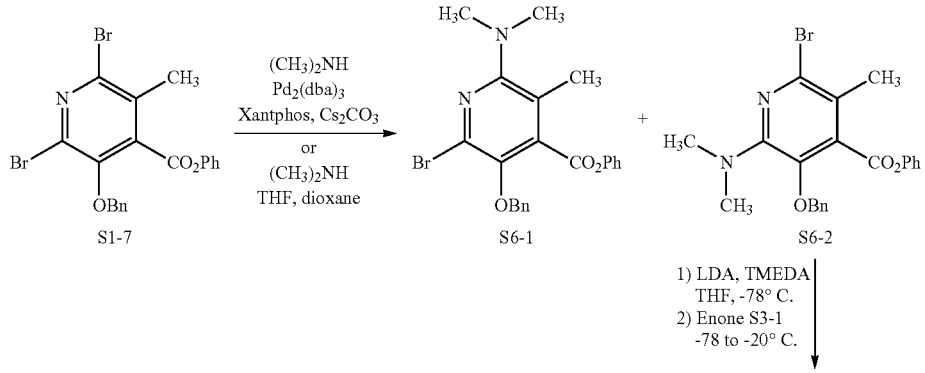

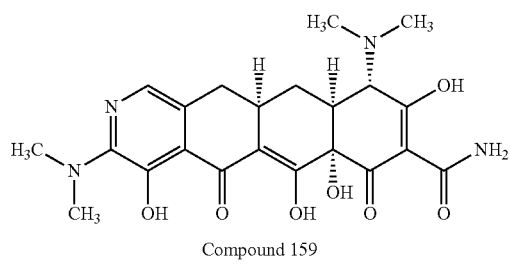

Compound 159

1) aq HF
2) H₂, Pd—C

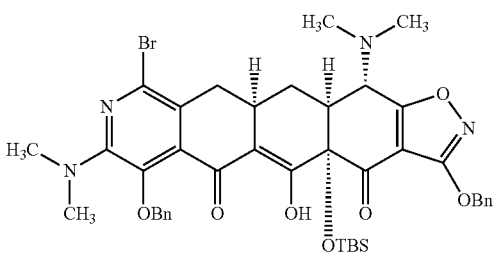

S6-3

Synthesis of S6-1

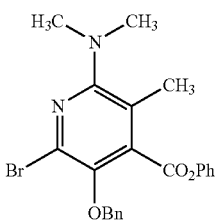

S6-1

Intermediate S1-7 (1.51 g, 3.16 mmol), Cs₂CO₃ (3.1 g, 9.5 mmol), tris(dibenzylideneacetone)dipalladium (145 mg, 0.158 mmol) and 9,9-dimethyl-4,5-bis-(diphenylphosphino)xanthene (267 mg, 0.474 mmol) were added to a vial equipped with a septum. After the flask was evacuated and flushed with nitrogen 3 times, 1,4-dioxane (7 mL) and dimethylamine (2.0 M solution in THF, 4.75 mL, 9.50 mmol) were added. The reaction mixture was heated to 60° C. and stirred for 4 h. The reaction mixture was allowed to cool to rt, was filtered through Celite, and was concentrated under reduced pressure. The material was purified by column chromatography (Biotage 50 g column, 0 to 10% EtOAc in hexanes gradient), yielding 868 mg (58%) of the major regioisomer S6-1. 354 mg (24%) of the minor regioisomer S6-2 was also obtained. ¹H NMR (400 MHz, CDCl₃) δ 7.50-7.46 (m, 2H), 7.41-7.30 (m, 5H), 7.30-7.24 (m, 1H), 7.08-7.02 (m, 2H), 5.08 (s, 2H), 2.85 (s, 6H), 2.32 (s, 3H); MS (ESI) m/z 441.19, 443.18 (M+H); $R_f$=0.29 in 10% EtOAc/hexanes. The regiochemistry was confirmed by an NOE between the methyl protons and the N,N-dimethylamino protons (0.61%).

Synthesis of S6-2

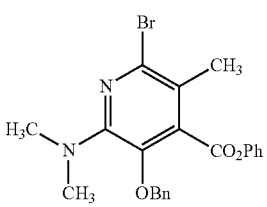

S6-2

Intermediate S1-7 (344 mg, 0.721 mmol) and dimethylamine (2.0 M solution in THF, 0.72 mL, 1.44 mmol) were heated to 80° C. in 1,4-dioxane (1.3 mL) in a sealed vial. After 6 h, additional dimethylamine (0.35 mL, 0.70 mmol) was added. After stirring overnight, the reaction mixture was cooled to rt and was concentrated under reduced pressure. The material was purified by column chromatography (Biotage 20 g column, 0 to 8% EtOAc in hexanes gradient), yielding 103 mg (33%) of the major regioisomer S6-2. Additional S6-2 was also isolated as a mixture with the minor regioisomer, S6-1. ¹H NMR (400 MHz, CDCl₃) δ 7.41-7.31 (m, 7H), 7.30-7.20 (m, 1H), 7.01 (d, J=7.3 Hz, 2H), 4.94 (s, 2H), 3.04 (s, 6H), 2.33 (s, 3H); MS (ESI) m/z 441.19, 443.18 (M+H); $R_f$=0.40 in 10% EtOAc/hexanes. The regiochemistry was confirmed by NOE between the benzylic protons of the O-benzyl group and the N,N-dimethylamino protons (0.44%).

Synthesis of S6-3

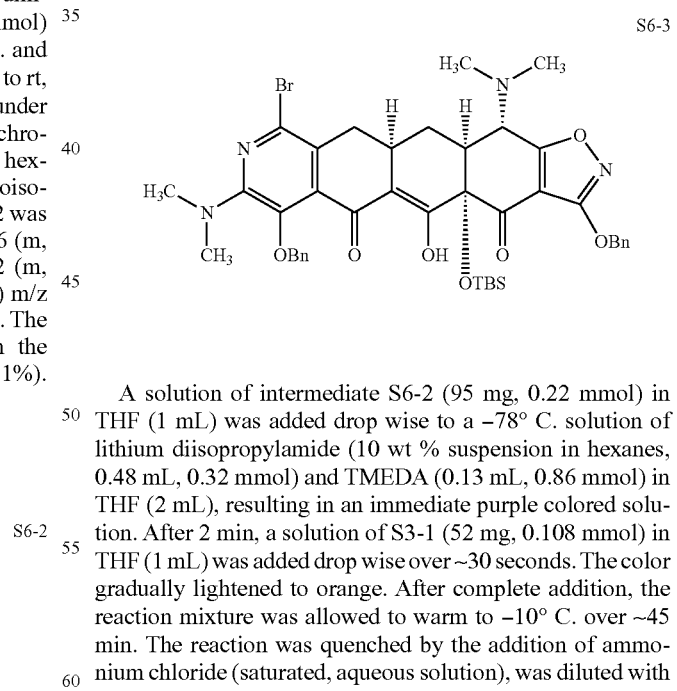

S6-3

A solution of intermediate S6-2 (95 mg, 0.22 mmol) in THF (1 mL) was added drop wise to a −78° C. solution of lithium diisopropylamide (10 wt % suspension in hexanes, 0.48 mL, 0.32 mmol) and TMEDA (0.13 mL, 0.86 mmol) in THF (2 mL), resulting in an immediate purple colored solution. After 2 min, a solution of S3-1 (52 mg, 0.108 mmol) in THF (1 mL) was added drop wise over ~30 seconds. The color gradually lightened to orange. After complete addition, the reaction mixture was allowed to warm to −10° C. over ~45 min. The reaction was quenched by the addition of ammonium chloride (saturated, aqueous solution), was diluted with water, and was extracted with EtOAc (2×). The combined extracts were dried over Na₂SO₄, filtered, and concentrated under reduced pressure. The material was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 90→100% B; mass-directed fraction collection], yielding 31.1 mg (35%) of the desired product as a yellow solid. MS (ESI) m/z 829.44, 831.43 (M+H).

Compound 159

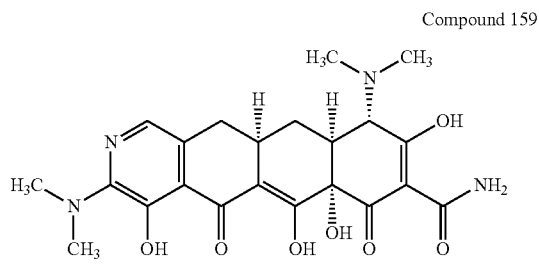 [SMILES: CN(C)c1ncc2c(c1O)C(=O)C1=C(O)[C@]3(O)C(=O)C(C(N)=O)=C(O)[C@@H](N(C)C)[C@@H]3C[C@@H]1C2]

Compound 159

Aqueous HF (0.4 mL, 48%) was added to a solution of S6-3 (10 mg, 0.012 mmol) in $CH_3CN$ (0.4 mL) in a plastic vial. After 18 h, the reaction mixture was poured into a solution of $K_2HPO_4$ (4.8 g) in water (15 mL). The mixture was extracted with EtOAc (3×). The combined EtOAc extracts were dried over $Na_2SO_4$, filtered and concentrated under reduced pressure. The material was dissolved in methanol (1 mL) and 1,4-dioxane (1 mL), and palladium on carbon (Degussa, 10 wt %, ~2 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 4.5 mg (70%, 2 steps) of the desired product as a yellow solid. $^1H$ NMR (400 MHz, $CD_3OD$ with 1 drop DCl) δ 7.38 (s, 1H), 4.20 (s, 1H), 3.44 (s, 6H), 3.18-2.86 (m, 9H), 2.42-2.26 (m, 2H), 1.64-1.52 (m, 1H); MS (ESI) m/z 459.39 (M+H).

Example 7

Preparation of Compound 118

Compound 118 was prepared according to Scheme 7.

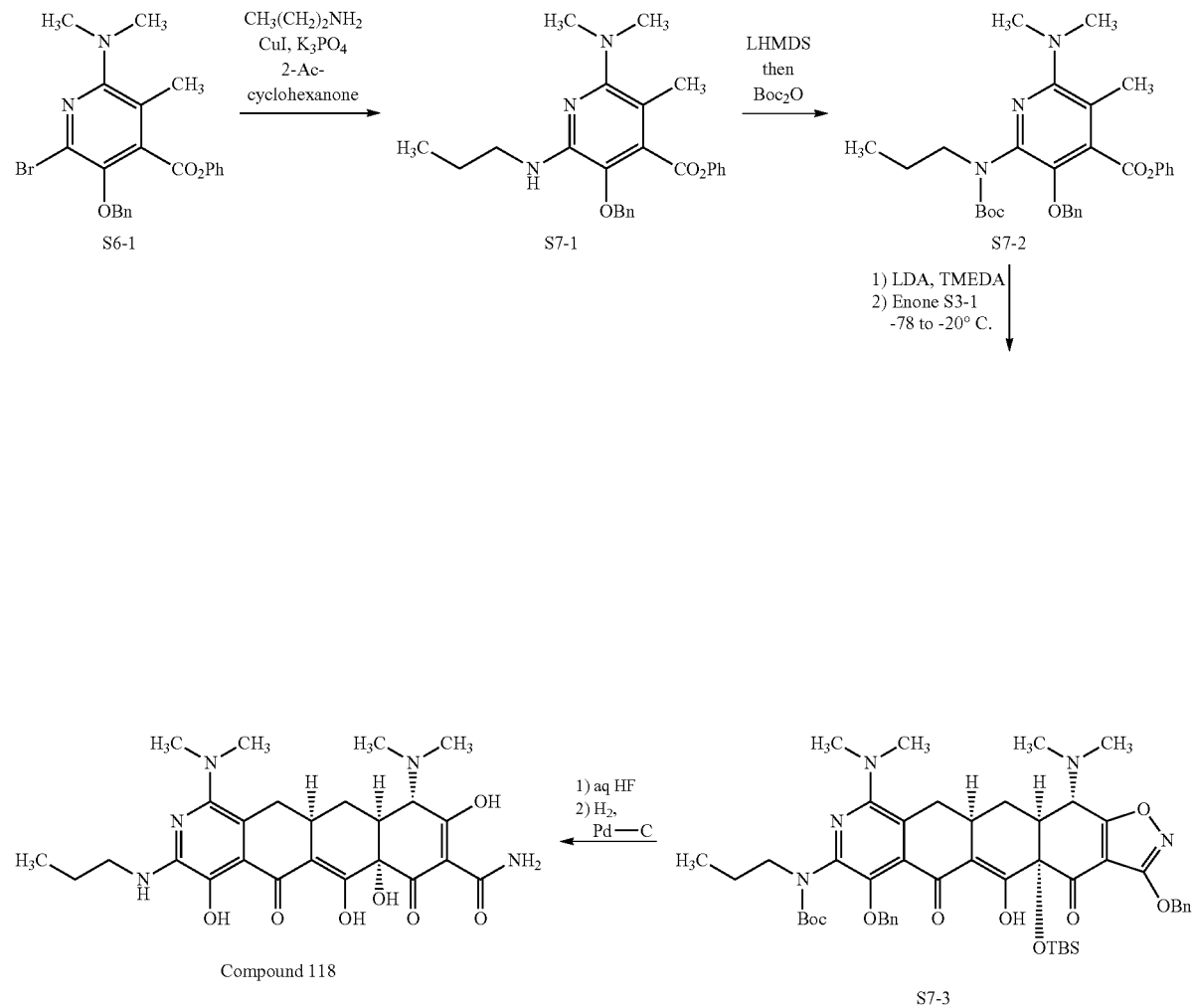

Synthesis of S7-1

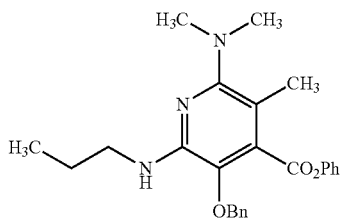

Copper(I) iodide (4.7 mg, 0.025 mmol) and K₃PO₄ (209 mg, 0.984 mmol) were added to a vial equipped with a septum. After the vial was evacuated and flushed with nitrogen (3×), a solution of intermediate S6-1 (217 mg, 0.492 mmol) in DMF (2 mL), 1-propylamine (0.162 mL, 1.97 mmol) and 2-acetylcyclohexanone (0.013 mL, 0.098 mmol) were added. The reaction mixture was heated to 100° C. for 3 h. The reaction mixture was allowed to cool to rt, was diluted with EtOAc (50 mL), and was washed with water (3×40 mL). The organics were dried over Na₂SO₄, filtered, and concentrated under reduced pressure. The material was purified by column chromatography (Biotage 10 g column, 0 to 12% EtOAc in hexanes gradient), yielding 74.6 mg (36%) of the product as a thick oil. MS (ESI) m/z 420.34 (M+H); $R_f$=0.32 in 10% EtOAc/hexanes.

Synthesis of S7-2

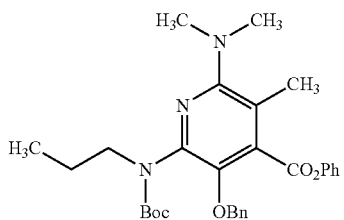

LHMDS (1.0 M solution in THF, 0.167 mL, 0.167 mmol) was added to a solution of S7-1 (63.5 mg, 0.152 mmol) in THF (2 mL), resulting in a bright yellow solution. A solution of di-t-butyldicarbonate (99.5 mg, 0.456 mmol) in THF (1 mL) was added. After 10 min, the reaction was quenched by the addition of ammonium chloride (saturated, aqueous solution) and was extracted with EtOAc (2×). The organics were dried over Na₂SO₄, filtered, and concentrated under reduced pressure. The material was purified by column chromatography (Biotage 10 g column, 0 to 12% EtOAc in hexanes gradient), yielding 13.6 mg (17%) of the product. ¹H NMR (400 MHz, CDCl₃) δ 7.40-7.28 (m, 7H), 7.28-7.22 (m, 1H), 7.05-7.00 (m, 2H), 4.90 (s, 2H), 2.79 (s, 6H), 2.34 (s, 3H), 1.76-1.66 (m, 2H), 1.56-1.50 (m, 2H), 0.91 (t, J=7.56 Hz, 3H); MS (ESI) m/z 520.38 (M+H); $R_f$=0.22 in 10% EtOAc/hexanes.

Synthesis of S7-3

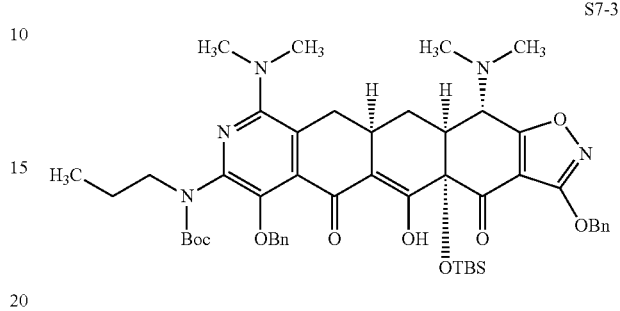

A solution of intermediate S7-2 (24 mg, 0.047 mmol) in THF (0.5 mL) was added drop wise to a −78° C. solution of lithium diisopropylamide (0.5 M solution in THF, 0.102 mL, 0.051 mmol) and TMEDA (0.041 mL, 0.27 mmol) in THF (2 mL), resulting in a yellowish orange colored solution. After 10 min, a solution of S3-1 (16.4 mg, 0.034 mmol) in THF (0.5 mL) was added drop wise. After complete addition, the reaction mixture was allowed to warm to −20° C. over ~45 min. The reaction was quenched by the addition of ammonium chloride (saturated, aqueous solution) and was extracted with EtOAc (2×). The combined extracts were dried over Na₂SO₄, filtered, and concentrated under reduced pressure. The material was purified on a Waters Autopurification system equipped with a Sunfire Prep C18 OBD column [5 µm, 19×50 mm; flow rate, 20 mL/min; Solvent A: H₂O with 0.1% HCO₂H; Solvent B: CH₃CN with 0.1% HCO₂H; gradient: 90→100% B; mass-directed fraction collection], yielding 6.1 mg (20%) of the desired product as a yellow solid. ¹H NMR (400 MHz, CDCl₃) δ 15.56 (s, 1H), 7.52-7.24 (m, 10H), 5.36 (s, 2H), 4.99-4.64 (m, 2H), 4.02 (d, J=11.0 Hz, 1H), 3.10-2.81 (m, 2H), 2.78 (s, 6H), 2.62-2.40 (m, 10H), 2.20-2.14 (m, 1H), 1.80-1.45 (m, 2H), 1.44-1.15 (m, 11H), 1.00-0.70 (m, 12H), 0.25 (s, 3H), 0.12 (s, 3H); MS (ESI) m/z 908.65 (M+H).

Compound 118

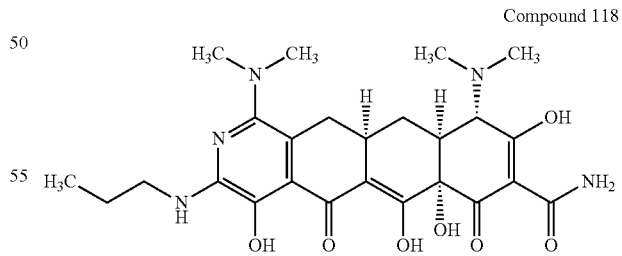

Aqueous HF (0.4 mL, 48%) was added to a solution of S7-3 (6.1 mg, 0.007 mmol) in CH₃CN (0.6 mL) in a plastic vial. After 18 h, the reaction mixture was poured into a solution of K₂HPO₄ (4.8 g) in water (15 mL). The mixture was extracted with EtOAc (3×). The combined EtOAc extracts were dried over Na₂SO₄, filtered and concentrated under reduced pressure. The material was dissolved in methanol (1 mL) and 1,4-dioxane (1 mL), and palladium on carbon (Degussa, 10 wt %, ~2 mg) was added. An atmosphere of hydrogen was introduced, and the reaction mixture was stirred for 4 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 2.8 mg (70%, 2 steps) of Compound 118 as a yellow solid. $^1$H NMR (400 MHz, $CD_3OD$ with 1 drop DCl) δ 4.19 (s, 1H), 3.44 (t, J=7.6 Hz, 2H), 3.24-3.12 (m, 7H), 3.12-2.97 (m, 8H), 2.39-2.26 (m, 2H), 1.73-1.56 (m, 3H), 0.98 (t, J=8.4 Hz, 3H); MS (ESI) m/z 516.42 (M+H).

Example 8

Preparation of Compounds 138 and 144

Compounds 138 and 144 were prepared according to Scheme 8.

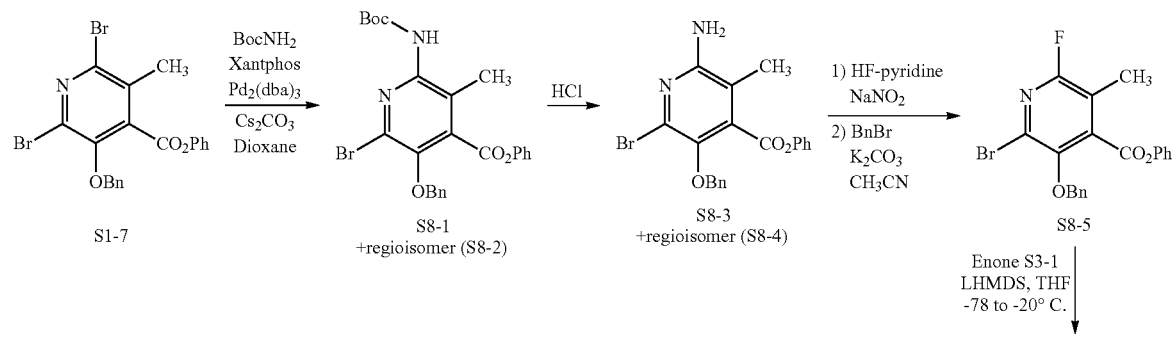

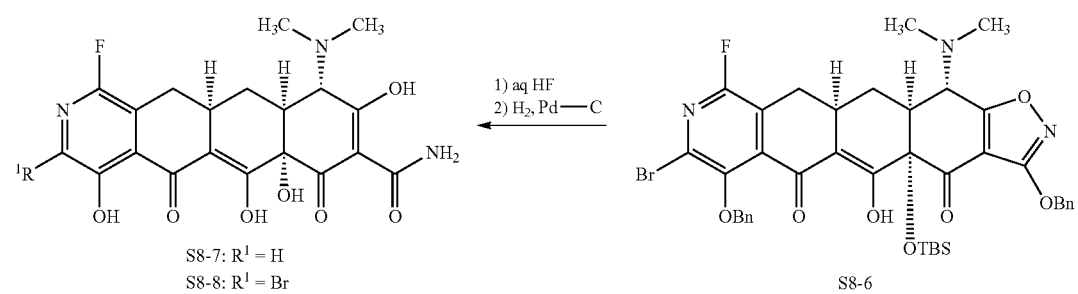

Synthesis of S8-1 and S8-2

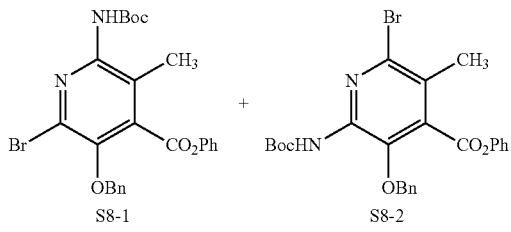

Intermediate S1-7 (2.15 g, 4.50 mmol), t-butylcarbamate (633 mg, 5.40 mmol), Cs$_2$CO$_3$ (2.93 g, 9.00 mmol), tris(dibenzylideneacetone)-dipalladium (206 mg, 0.225 mmol) and 9,9-dimethyl-4,5-bis-(diphenylphosphino)-xanthene (380 mg, 0.673 mmol) were weighed into a flask. This was evacuated and back-flushed with nitrogen (3×), and 1,4-dioxane (15 mL) was added. The reaction mixture was heated to 80° C. After 3 h, the reaction mixture was cooled to rt, was diluted with EtOAc (100 mL) and was washed with water (2×50 mL). The organics were dried over Na$_2$SO$_4$, filtered, and concentrated under reduced pressure. The material was purified by column chromatography (Biotage 50 g column, 0 to 12% EtOAc in hexanes gradient), yielding 1.43 g (62%) of a 4:1 mixture of the two regioisomeric compounds. $^1$H NMR (400 MHz, CDCl$_3$) δ 7.51-7.46 (m, 2H), 7.42-7.32 (m, 7H), 7.30-7.24 (m, 1H), 7.12 (d, J=8.2 Hz, 0.5H), 7.03 (d, J=8.2 Hz, 2H), 6.88 (s, 0.25H), 6.71 (s, 1H), 5.12 (s, 2H), 5.02 (s, 0.5H), 2.43 (s, 0.75H), 2.34 (s, 3H), 1.50 (s, 9H), 1.47 (s, 2.25H); MS (ESI) m/z 535.10, 537.10 (M+Na).

Synthesis of S8-3 and S8-4

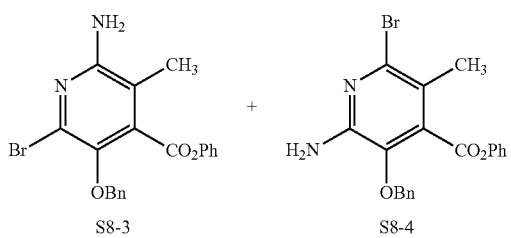

The mixture of S8-1 and S8-2 (1.43 g, 2.78 mmol) was stirred in 4 M HCl in 1,4-dioxane (20 mL) and 1,4-dioxane (5 mL) overnight. The reaction mixture was diluted with EtOAc (100 mL) and was washed with NaHCO$_3$ (saturated, aqueous solution, 2×100 mL). The organics were dried over Na$_2$SO$_4$, filtered and concentrated under reduced pressure. The material was purified by column chromatography (Biotage 20 g column, 0 to 30% EtOAc in hexanes gradient), yielding 805 mg (70%) of the major regioisomer S8-3 and 270 mg (24%) of the minor regioisomer S8-4. Data for S8-3: R$_f$=0.39 in 40% EtOAc/hexanes; $^1$H NMR (400 MHz, CDCl$_3$) δ 7.50-7.42 (m, 2H), 7.40-7.30 (m, 5H), 7.30-7.24 (m, 1H), 7.04 (d, J=8.2 Hz, 2H), 5.06 (s, 2H), 4.56 (s, 2H), 2.16 (s, 3H); MS (ESI) m/z 413.11, 415.01 (M+H). Data for S8-4: R$_f$=0.72 in 40% EtOAc/hexanes; $^1$H NMR (400 MHz, CDCl$_3$) δ 7.42-7.34 (m, 8H), 7.13-7.10 (m, 2H), 5.01 (s, 2H), 4.64 (s, 2H), 2.35 (s, 3H); MS (ESI) m/z 413.09, 415.09 (M+H).

Synthesis of S8-5

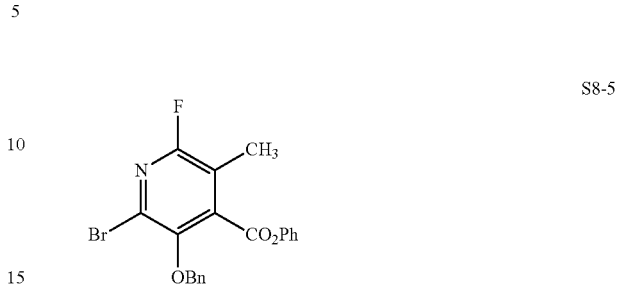

HF-Pyridine solution (~70% HF, 2 mL) was added to a 0° C. solution of intermediate S8-3 (884 mg, 2.14 mmol) in pyridine (1 mL). Sodium nitrite (177 mg, 2.57 mmol) was added (bubbling), and the reaction was allowed to slowly warm to rt. After 3 days, the reaction mixture was poured into Na$_2$CO$_3$ (saturated, aqueous solution, 30 mL) and was extracted with EtOAc (3×30 mL). The combined extracts were washed with HCl (1 N aqueous solution, 2×50 mL) and were dried over Na$_2$SO$_4$, filtered and concentrated under reduced pressure. The material was purified by column chromatography (Biotage 20 g column, 0 to 6% EtOAc in hexanes gradient), yielding 687 mg (77%) of the product as a colorless oil that slowly solidified on standing. R$_f$=0.39 in 10% EtOAc/hexanes; $^1$H NMR (400 MHz, CDCl$_3$) δ 7.50-7.42 (m, 2H), 7.40-7.30 (m, 5H), 7.30-7.24 (m, 1H), 7.08-7.02 (m, 2H), 5.14 (s, 2H), 2.33 (s, 3H); MS (ESI) m/z 416.17, 418.15 (M+H).

Synthesis of S8-6

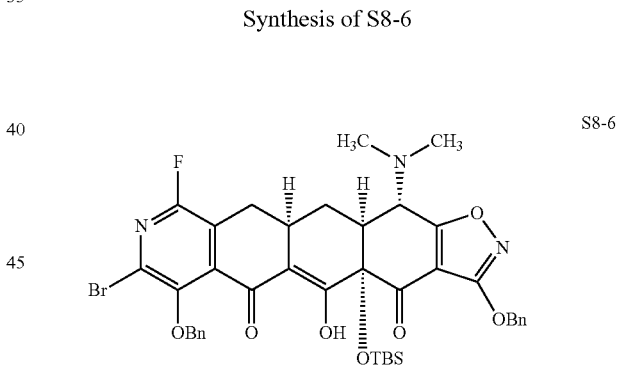

LHMDS solution (1.0 M, 0.621 mL, 0.621 mmol) was added over ~2 min to a −78° C. solution of intermediate S8-5 (86 mg, 0.207 mmol) and S3-1 (99 mg, 0.207 mmol) in THF (2 mL). After 45 min, the reaction mixture was allowed to slowly warm to −20° C. over 1 hr. The reaction mixture was quenched by the addition of NH$_4$Cl (saturated, aqueous solution) and was extracted with EtOAc. The extracts were dried over Na$_2$SO$_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 80→100% B; mass-directed fraction collection], yielding 75.3 mg (45%) of the desired product as a yellow solid. $^1$H NMR (400 MHz, CDCl$_3$) δ 15.55 (s, 1H), 7.56-7.26 (m, 10H), 5.36 (s, 2H), 5.02 (s, 2H), 3.88 (d, J=10.4 Hz, 1H), 3.18-3.04 (m, 2H), 2.62-2.58 (m, 1H), 2.58-2.40 (m, 8H), 2.17 (d, J=14.6 Hz, 1H), 0.81 (s, 9H), 0.25 (s, 3H), 0.12 (s, 3H); MS (ESI) m/z 804.34, 806.34 (M+H).

Compound 144

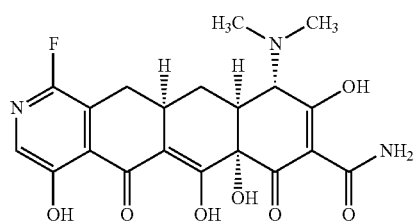

Compound 144

Aqueous HF (0.4 mL, 48%) was added to a solution of S8-6 (37.5 mg, 0.0466 mmol) in $CH_3CN$ (0.6 mL) in a plastic vial. After 18 h, the reaction mixture was poured into a solution of $K_2HPO_4$ (4.8 g) in water. The mixture was extracted with EtOAc, and the combined extracts were dried over $Na_2SO_4$, filtered and concentrated under reduced pressure. The material was dissolved in methanol (2 mL) and 1,4-dioxane (2 mL), and palladium on carbon (Degussa, 10 wt %, ~5 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 14.9 mg (68%, 2 steps) of Compound 144 as a yellow solid. In addition, 3.8 mg (15%) of the 9-Br compound, Compound 138, were also isolated (see below). Data for Compound 144: $^1$H NMR (400 MHz, $CD_3OD$ with 1 drop DCl) δ 7.81 (s, 1H), 4.17 (s, 1H), 3.26-2.96 (m, 9H), 2.42-2.25 (m, 2H), 1.70-1.58 (m, 1H); MS (ESI) m/z 434.27 (M+H).

Compound 138

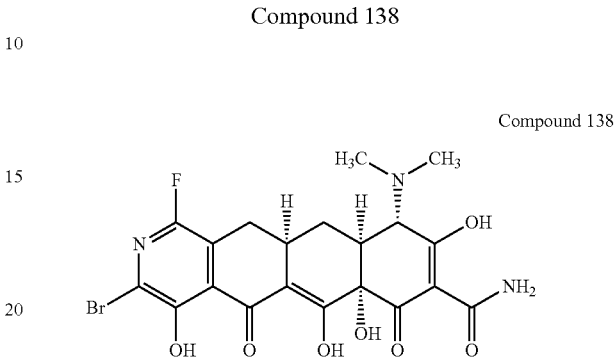

Compound 138

$^1$H NMR (400 MHz, $CD_3OD$ with 1 drop DCl) δ 4.18 (s, 1H), 3.26-2.94 (m, 9H), 2.42-2.26 (m, 2H), 1.72-1.57 (m, 1H); MS (ESI) m/z 512.17, 514.17 (M+H).

Example 9

Preparation of Compounds of Formula I, wherein X is hydrogen and Z is —NH($R^3$)

Compounds of Formula I, wherein X is hydrogen and Z is —NH($R^3$) (as well as compounds of Formula II, wherein Z is —NH($R^3$)) were prepared according to Scheme 9.

Scheme 9

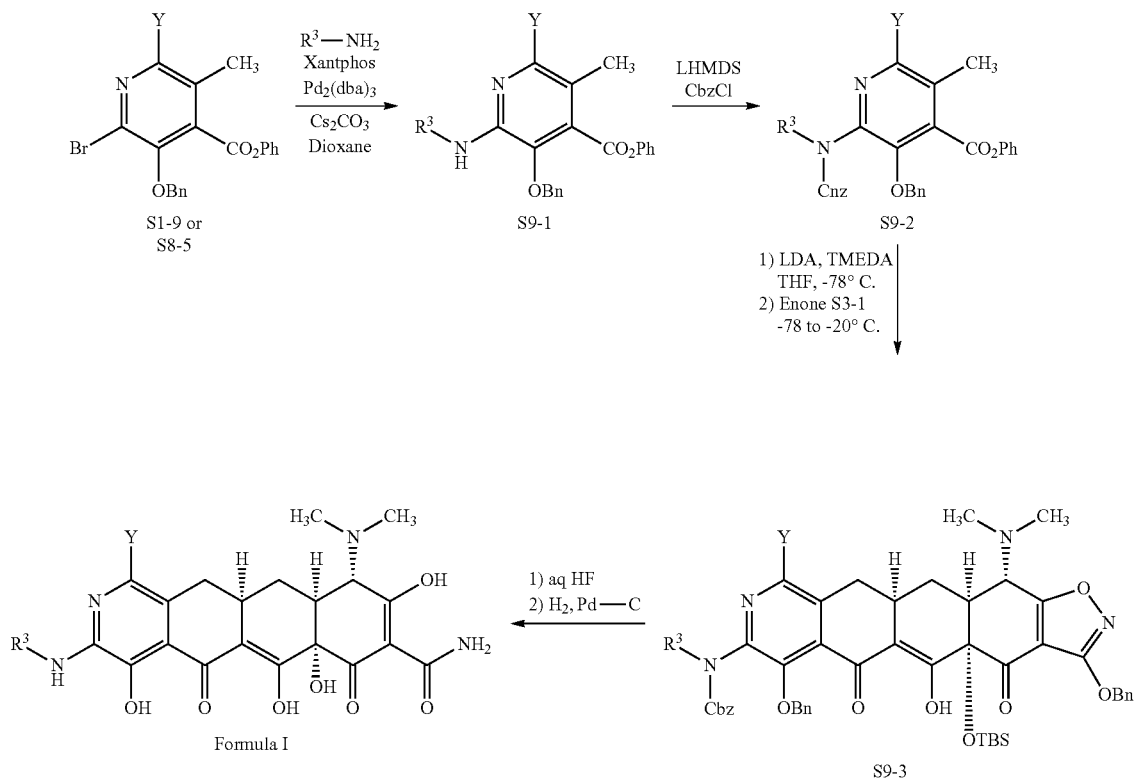

Specific intermediates and compounds of the invention prepared according to Scheme 9 are described below.

Synthesis of S9-1-1

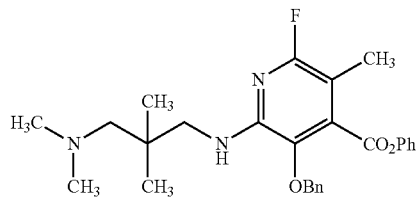

S9-1-1

Intermediate S8-5 (100 mg, 0.24 mmol), Cs$_2$CO$_3$ (235 mg, 0.720 mmol), tris(dibenzylideneacetone)dipalladium (11 mg, 0.012 mmol) and 9,9-dimethyl-4,5-bis-(diphenylphosphino)xanthene (20 mg, 0.036 mmol) were weighed into a flask. This was evacuated and back-flushed with nitrogen (3×), and 1,4-dioxane (0.5 mL) and N,N-dimethylneopentanediamine (0.057 mL, 0.36 mmol) were added. The reaction mixture was heated to 70° C. After 1.5 h, the reaction mixture was cooled to rt and was filtered through Celite. The filtrate was concentrated under reduced pressure and was purified by column chromatography (Biotage 10 g column, 0 to 3% methanol in CH$_2$Cl$_2$ gradient), yielding 76.9 mg (69%) of the product. R$_f$=0.25 in 5% methanol/CH$_2$Cl$_2$; MS (ESI) m/z 466.28 (M+H).

Synthesis of S9-2-1

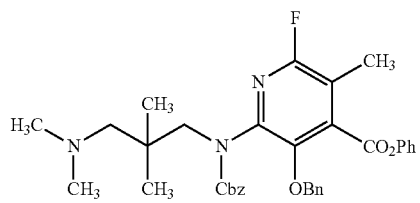

S9-2-1

LHMDS solution (1.0 M, 0.22 mL, 0.22 mmol) was added drop wise to a −78° C. solution of S9-1-1 (93 mg, 0.20 mmol) in THF (5 mL). After 5 min, benzyl chloroformate (0.084 mL, 0.60 mmol) was added. After 15 min, the reaction mixture was quenched by the addition of NH$_4$Cl (saturated, aqueous solution, 15 mL) and was extracted with EtOAc. The organics were dried over Na$_2$SO$_4$, filtered, and concentrated under reduced pressure. The material was purified by column chromatography (Biotage 10 g column, 0 to 7% methanol in CH$_2$Cl$_2$ gradient), yielding 111 mg (93%) of the product. R$_f$=0.42 in 10% methanol/CH$_2$Cl$_2$; $^1$H NMR (400 MHz, CDCl$_3$) δ 7.45-7.20 (m, 13H), 7.06-6.98 (m, 2H), 5.16 (s, 2H), 4.87 (s, 2H), 3.78 (br s, 2H), 2.38 (s, 3H), 2.18 (br s, 6H), 1.62 (br s, 2H), 0.90 (br s, 6H); MS (ESI) m/z 600.28 (M+H).

Synthesis of S9-3-1

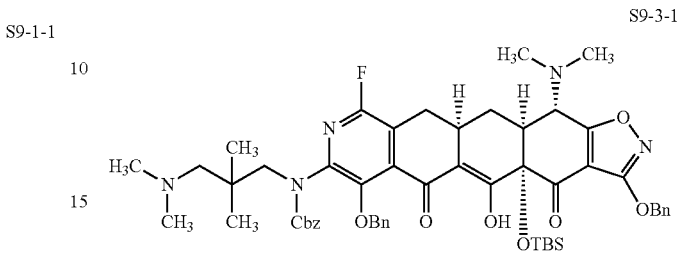

S9-3-1

A solution of intermediate S9-2-1 (54 mg, 0.090 mmol) in THF (0.5 mL) was added drop wise to a −78° C. solution of lithium diisopropylamide (2.0 M solution in THF, 0.112 mL, 0.224 mmol) and TMEDA (0.081 mL, 0.54 mmol) in THF (2 mL), resulting in an orange colored solution. After 10 min, a solution of S3-1 (43 mg, 0.090 mmol) in THF (0.5 mL) was added drop wise over ~30 seconds. After complete addition, the reaction mixture was allowed to warm to −10° C. over 1 h. The reaction was quenched by the addition of ammonium chloride (saturated, aqueous solution), was diluted with water, and was extracted with EtOAc (2×). The combined extracts were dried over Na$_2$SO$_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 20→100% B; mass-directed fraction collection], yielding 22.9 mg (26%) of the desired product as a yellow solid. $^1$H NMR (400 MHz, CDCl$_3$) δ 15.55 (br s, 1H), 7.52-7.20 (m, 15H), 5.36 (s, 2H), 5.20-5.00 (m, 2H), 4.80 (s, 2H), 3.90 (d, J=11.0 Hz, 1H), 3.19-3.05 (m, 2H), 2.62-2.57 (m, 1H), 2.56-2.12 (m, 19H), 0.94-0.74 (m, 15H), 0.26 (s, 3H), 0.12 (s, 3H); MS (ESI) m/z 988.59 (M+H).

Compound 133

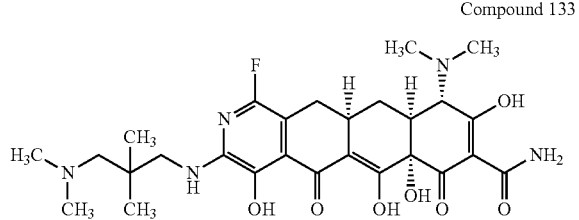 [SMILES: CN(C)CC(C)(C)CNc1nc(F)c2c(c1O)C(=O)C1=C(O)[C@]3(O)C(=O)C(C(N)=O)=C(O)[C@@H](N(C)C)[C@@H]3C[C@@H]1C2]

Compound 133

Aqueous HF (0.4 mL, 48%) was added to a solution of S9-3-1 (22.9 mg, 0.0232 mmol) in CH$_3$CN (0.8 mL) in a plastic vial. After 18 h, the reaction mixture was poured into a solution of K$_2$HPO$_4$ (4.8 g) in water. The mixture was extracted with EtOAc, and the combined extracts were dried over Na$_2$SO$_4$, filtered and concentrated under reduced pressure. The material was dissolved in methanol (1 mL), 0.5 M HCl in methanol (0.2 mL) and 1,4-dioxane (1 mL), and palladium on carbon (Degussa, 10 wt %, ~2 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 0→100% B; mass-directed fraction collection]. Fractions with the desired MW were collected and freeze-dried to yield 9.9 mg (67%, 2 steps) of Compound 133 as a yellow solid. ¹H NMR (400 MHz, CD₃OD with 1 drop DCl) δ 4.16 (s, 1H), 3.43 (s, 2H), 3.15-2.90 (m, 17H), 2.30-2.22 (m, 1H), 2.22-2.12 (m, 1H), 1.65-1.54 (m, 1H), 1.17, (s, 6H); MS (ESI) m/z 562.43 (M+H).

The following compounds were prepared similarly to Compound 133 by substituting the appropriate amine for N,N-dimethylneopentanediamine Compound 114

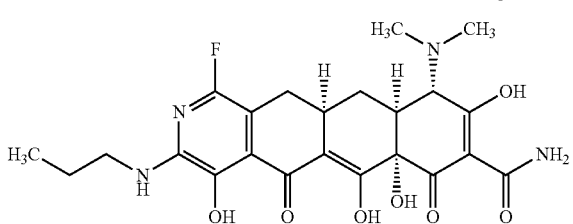

Compound 114

¹H NMR (400 MHz, CD₃OD) δ 4.09 (s, 1H), 3.33 (t, J=6.9 Hz, 2H) 3.42-3.38 (m, 2H), 3.20 (s, 1H), 3.07-2.94 (m, 8H), 2.91 (dd, J=14.6, 4.6 Hz, 1H), 2.23-2.12 (m, 2H), 1.68-1.55 (m, 3H), 0.96 (t, J=7.3 Hz, 3H); MS (ESI) m/z 491.23 (M+H).

Compound 108

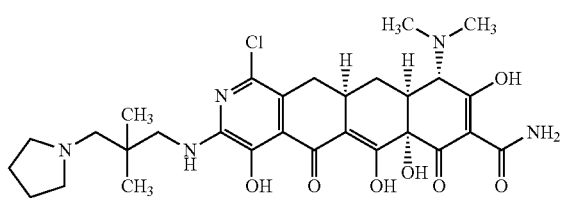

Compound 108

¹H NMR (400 MHz, CD₃OD) δ 4.09 (s, 1H), 3.88-3.78 (m, 2H), 3.50-3.39 (m, 2H), 3.18-2.92 (m, 9H), 2.32-2.08 (m, 6H), 1.67-1.56 (m, 1H), 1.15 (s, 6H); MS (ESI) m/z 604.29 (M+H).

Compound 129

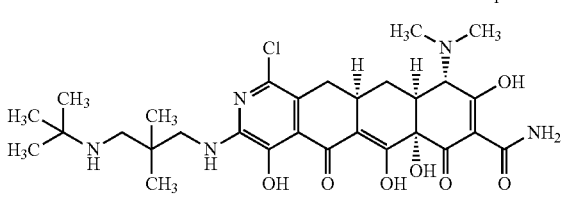

Compound 129

¹H NMR (400 MHz, CD₃OD) δ 4.11 (s, 1H), 3.54-3.39 (m, 4H), 3.15-2.92 (m, 9H), 2.38-2.20 (m, 2H), 1.69-1.55 (m, 1H), 1.48 (s, 9H); MS (ESI) m/z 606.34 (M+H).

Compound 135

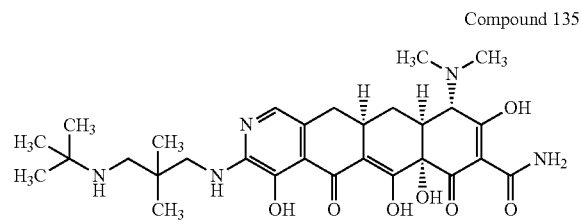 [SMILES: CN(C)[C@@H]1C(O)=C(C(N)=O)C(=O)[C@@]2(O)C(O)=C3C(=O)c4c(cnc(NCC(C)(C)CNC(C)(C)C)c4O)C[C@H]3C[C@@H]12]

Compound 135 was isolated as a side product in the synthesis of Compound 129. ¹H NMR (400 MHz, CD₃OD) δ 7.85 (s, 1H), 4.12 (s, 1H), 3.68-3.45 (m, 4H), 3.17-2.94 (m, 9H), 2.42-2.21 (m, 2H), 1.69-1.59 (m, 1H), 1.47 (s, 9H); MS (ESI) m/z 572.28 (M+H).

Compound 151

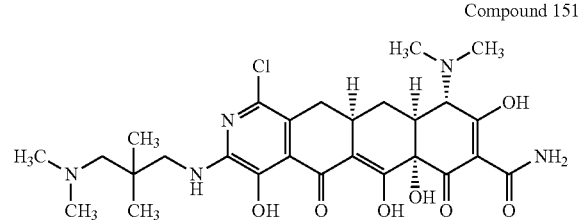

Compound 151

¹H NMR (400 MHz, CD₃OD) δ 4.10 (s, 1H), 3.51-3.36 (m, 4H), 3.10-2.92 (m, 15H), 2.33-2.18 (m, 2H), 1.68-1.57 (m, 1H), 1.174 (s, 3H), 1.169 (s, 3H); MS (ESI) m/z 578.35 (M+H).

Compound 130

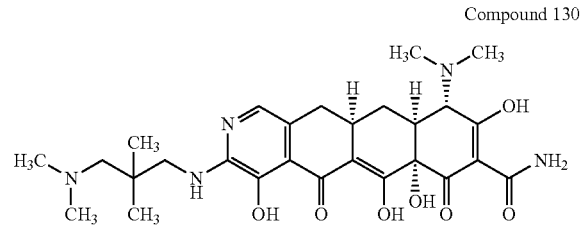 [SMILES: CN(C)CC(C)(C)CNc1ncc2c(c1O)C(=O)C1=C(O)[C@]3(O)C(=O)C(C(N)=O)=C(O)[C@@H](N(C)C)[C@@H]3C[C@@H]1C2]

Compound 130 was isolated as a side product in the synthesis of Compound 151. ¹H NMR (400 MHz, CD₃OD) δ 7.75 (s, 1H), 4.10 (s, 1H), 3.72-3.54 (m, 4H), 3.09-2.94 (m, 15H), 2.44-2.26 (m, 2H), 1.70-1.57 (m, 1H), 1.22 (s, 3H), 1.17 (s, 3H); MS (ESI) m/z 544.49 (M+H).

Example 10

Preparation of Compounds of Formula I, wherein X is Hydrogen and Z is —N(R³)(R⁴)

Compounds of Formula I, wherein X is hydrogen and Z is —N(R³)(R⁴) (as well as compounds of Formula II, wherein Z is —N(R³)(R⁴)) were prepared according to Scheme 10.

Scheme 10

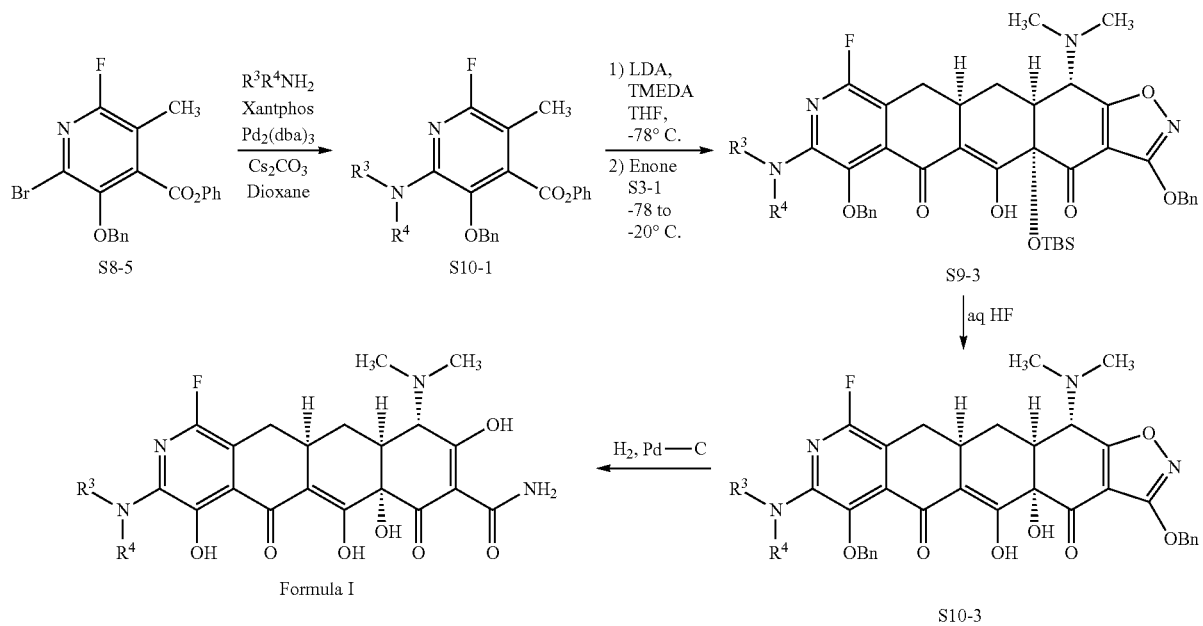

Specific intermediates and compounds of the invention prepared according to Scheme 10 are described below.

Synthesis of S10-1-1

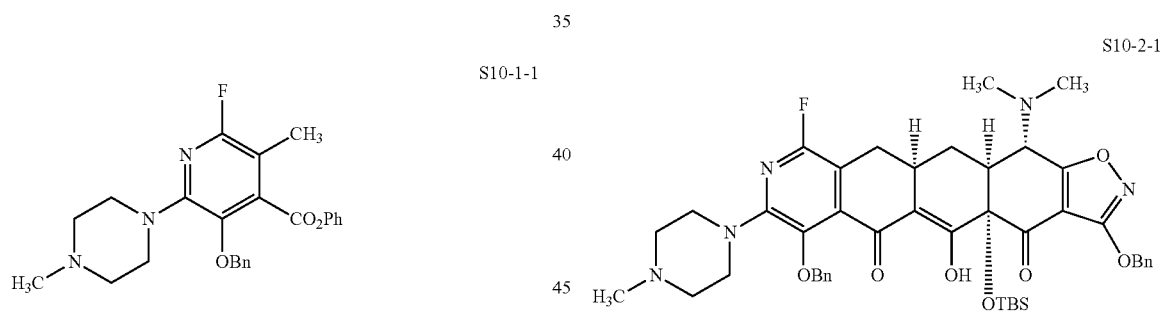

Intermediate S8-5 (63 mg, 0.15 mmol), Cs$_2$CO$_3$ (147 mg, 0.453 mmol), tris(dibenzylideneacetone)dipalladium (6.9 mg, 0.008 mmol) and 9,9-dimethyl-4,5-bis-(diphenylphosphino)xanthene (13 mg, 0.023 mmol) were weighed into a vial. This was evacuated and back-flushed with nitrogen (3×), and 1,4-dioxane (0.4 mL) and N-methylpiperazine (0.020 mL, 0.182 mmol) were added. The reaction mixture was heated to 70° C. After 3 h, an additional portion of N-methylpiperazine (0.020 mL, 0.182 mmol) was added, and the reaction mixture was heated to 100° C. After heating overnight, the reaction mixture was cooled to rt and was filtered through Celite. The filtrate was concentrated under reduced pressure and was purified by column chromatography (Biotage 10 g column, 0 to 3% methanol in CH$_2$Cl$_2$ gradient), yielding 18.7 mg (28%) of the product. R$_f$=0.23 in 5% methanol/CH$_2$Cl$_2$; MS (ESI) m/z 436.16 (M+H).

Synthesis of S10-2-1

A solution of intermediate S10-1-1 (18.7 mg, 0.043 mmol) in THF (0.5 mL) was added drop wise o a −78° C. solution of lithium diisopropylamide (2.0 M solution in THF, 0.043 mL, 0.086 mmol) and TMEDA (0.052 mL, 0.34 mmol) in THF (2 mL), resulting in a red colored solution. A solution of S3-1 (20.7 mg, 0.043 mmol) in THF (0.5 mL) was added, and the reaction mixture was allowed to warm to −10° C. The reaction was quenched by the addition of ammonium chloride (saturated, aqueous solution), was diluted with water, and was extracted with EtOAc (2×). The combined extracts were dried over Na$_2$SO$_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 20→100% B; mass-directed fraction collection], yielding 4.3 mg (12%) of the desired product as a yellow solid. $^1$H NMR (400 MHz, CDCl$_3$) δ 15.80 (br s, 1H), 7.52-7.20 (m, 10H), 5.36 (s, 2H), 4.83 (q, J=31.8 Hz, J=9.76 Hz, 2H), 3.88 (d, J=10.4 Hz, 1H), 3.85-3.72 (m, 4H), 3.01-2.94 (m, 2H), 2.88-2.76 (m, 4H), 2.60-2.32 (m, 12H), 2.16-2.10 (m, 1H), 0.81 (s, 9H), 0.26 (s, 3H), 0.12 (s, 3H); MS (ESI) m/z 824.51 (M+H).

Compound 106

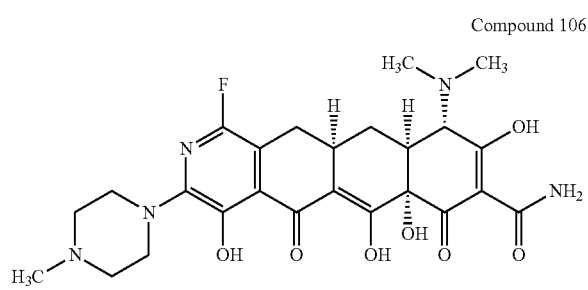 [SMILES: CN1CCN(c2nc(F)c3c(c2O)C(=O)C2=C(O)[C@]4(O)C(=O)C(C(N)=O)=C(O)[C@@H](N(C)C)[C@@H]4C[C@@H]2C3)CC1]

Compound 106

Aqueous HF (0.4 mL, 48%) was added to a solution of S10-2-1 (4.3 mg, 0.0052 mmol) in CH$_3$CN (0.8 mL) in a plastic vial. After 18 h, the reaction mixture was poured into a solution of K$_2$HPO$_4$ (4.8 g) in water. The mixture was extracted with EtOAc, and the combined extracts were dried over Na$_2$SO$_4$, filtered and concentrated under reduced pressure. The material was dissolved in methanol (1 mL), 0.5 M HCl in methanol (0.2 mL) and 1,4-dioxane (1 mL), and palladium on carbon (Degussa, 10 wt %, ~2 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH$_3$CN; gradient: 0→100% B; mass-directed fraction collection]. Fractions with the desired MW were collected and freeze-dried to yield 1.9 mg (61%, 2 steps) of Compound 106 as a yellow solid. $^1$H NMR (400 MHz, CD$_3$OD with 1 drop DCl) δ 4.40-4.28 (m, 2H), 4.18 (s, 1H), 3.60-3.54 (m, 2H), 3.15-2.92 (m, 12H), 2.32-2.22 (m, 6H), 1.66-1.54 (m, 1H); MS (ESI) m/z 532.15 (M+H).

Example 11

Preparation of Compounds of Formula I, wherein X is Hydrogen and Z is —NH—C(O)—(C$_0$-C$_6$) alkylene-N(R$^5$)(R$^6$) or —NH—C(O)—(C$_1$-C$_6$ alkyl)

Compounds of Formula I, wherein X is hydrogen and Z is —NH—C(O)—(C$_0$-C$_6$) alkylene-N(R$^5$)(R$^6$), —NH—S(O)$_2$—R$^5$ or —NH—C(O)—R$^5$ (as well as compounds of Formula II, wherein Z is —NH—C(O)—(C$_0$-C$_6$) alkylene-N(R$^5$)(R$^6$), —NH—S(O)$_2$—R$^5$ or —NH—C(O)—R$^5$) were prepared according to Scheme 11.

Scheme 11

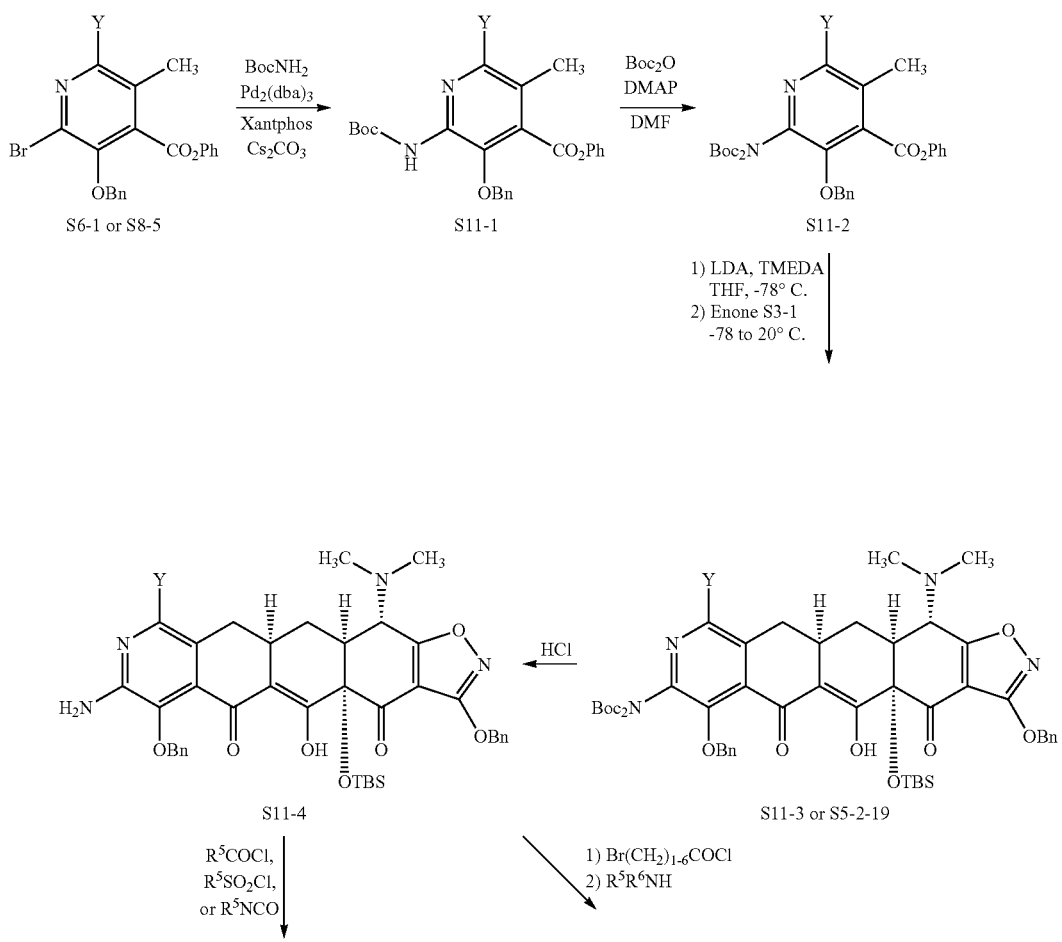

-continued

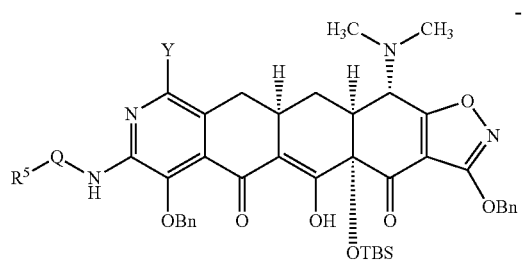

S11-5
Q = CO, SO$_2$, NHCO 1) aq HF
2) H$_2$, Pd—C

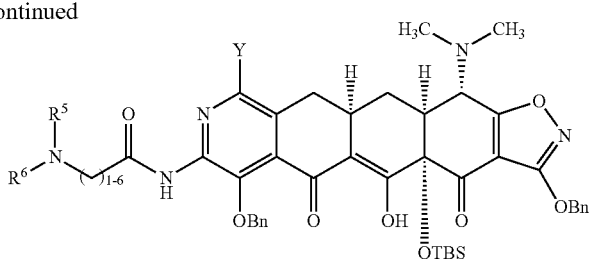

S11-7

1) aq HF
2) H$_2$, Pd—C

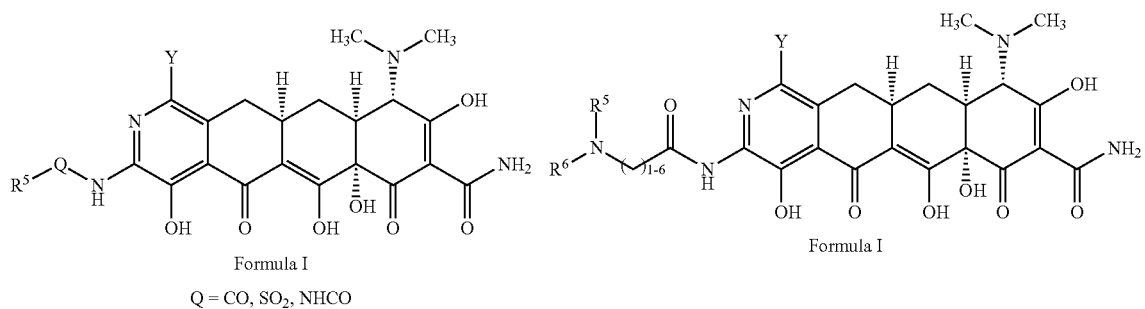

Formula I
Q = CO, SO$_2$, NHCO

Formula I

Specific intermediates and compounds of the invention prepared according to Scheme 11 are described below.

Synthesis of S11-1-1

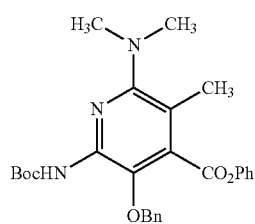

S11-1-1

Intermediate S6-1 (467 mg, 1.06 mmol), t-butylcarbamate (372 mg, 3.17 mmol), Cs$_2$CO$_3$ (1.04 g, 3.17 mmol), tris(dibenzylideneacetone)dipalladium (48 mg, 0.053 mmol) and 9,9-dimethyl-4,5-bis-(diphenylphosphino)xanthene (89.3 mg, 0.159 mmol) were weighed into a vial. This was evacuated and back-flushed with nitrogen (3×), and 1,4-dioxane (3 mL) was added. The reaction mixture was heated to 100° C. After 4 h, the reaction mixture was cooled to rt and was filtered through Celite. The filtrate was concentrated under reduced pressure, and the material was purified by column chromatography (Biotage 20 g column, 0 to 16% EtOAc in hexanes gradient), yielding 493 mg (98%) of the product containing ~20% of an unidentified impurity. R$_f$=0.45 in 30% EtOAc/hexanes; $^1$H NMR (400 MHz, CDCl$_3$) δ 7.43-7.32 (m, 8H), 7.30-7.24 (m, 1H), 7.15-7.10 (m, 2H), 6.80 (s, 1H), 4.94 (s, 2H), 2.85 (s, 6H), 2.31 (s, 3H), 1.48 (s, 9H); MS (ESI) m/z 478.27 (M+H).

Synthesis of S11-2-1

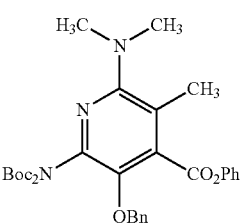

S11-2-1

Intermediate S11-1-1 (490 mg, 1.03 mmol) was treated with d-t-butyldicarbonate (672 mg, 3.08 mmol) and 4-dimethylaminopyridine (12.5 mg, 0.103 mmol) in DMF (5 mL). After stirring overnight, the reaction mixture was diluted with EtOAc (25 mL) and was washed with water (3×20 mL) and brine (20 mL). The organics were dried over Na$_2$SO$_4$, filtered, and concentrated under reduced pressure. The material was purified by column chromatography (Biotage 10 g column, 0 to 10% EtOAc in hexanes gradient), yielding 424 mg (72%) of the product. R$_f$=0.22 in 15% EtOAc/hexanes; $^1$H NMR (400 MHz, CDCl$_3$) δ 7.42-7.24 (m, 8H), 7.06-7.00 (m, 2H), 4.92 (s, 2H), 2.79 (s, 6H), 2.36 (s, 3H), 1.39 (s, 18H); MS (ESI) m/z 578.33 (M+H).

Synthesis of S11-3-1

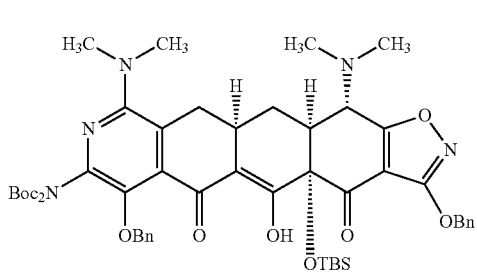

S11-3-1

Lithium diisopropylamide was prepared at –40° C. by the addition of n-BuLi (1.84 M solution in hexane, 0.458 mL, 0.843 mmol) to a solution of diisopropylamine (0.119 mL, 0.843 mmol) in THF (7 mL). TMEDA (0.507 mL, 3.37 mmol) was added, and the reaction mixture was cooled to –78° C. A solution of intermediate S11-2-1 (422 mg, 0.731 mmol) in THF (1.5 mL) was added drop wise, giving a reddish orange colored solution. After 5 min, a solution of S3-1 (271 mg, 0.562 mmol) in THF (1.5 mL) was added. The reaction mixture was allowed to warm to –10° C. over ~30 min. The reaction mixture was quenched by the addition of NH$_4$Cl (saturated, aqueous solution) and was extracted with EtOAc (2×). The extracts were dried over Na$_2$SO$_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 90→100% B; mass-directed fraction collection], yielding 288 mg (53%) of the desired product as a yellow solid. $^1$H NMR (400 MHz, CDCl$_3$) δ 15.50 (s, 1H), 7.52-7.24 (m, 10H), 5.36 (s, 2H), 4.85 (q, J=86.1 Hz, J=9.76 Hz, 2H), 4.02 (d, J=10.4 Hz, 1H), 3.08-3.00 (m, 1H), 3.00-2.82 (m, 1H), 2.77 (s, 6H), 2.62-2.38 (m, 9H), 2.20-2.12 (m, 1H), 1.35, (br s, 18H), 0.79 (s, 9H), 0.26 (s, 3H), 0.12 (s, 3H); MS (ESI) m/z 966.59 (M+H).

Synthesis of S11-4-1

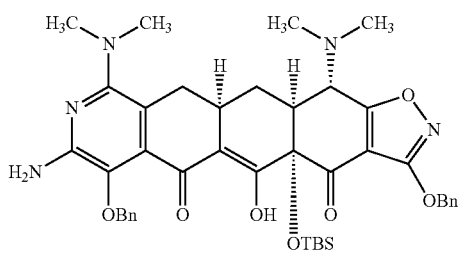

S11-4-1

Intermediate S11-3-1 (284 mg, 0.294 mmol) was stirred in 1,4-dioxane (3 mL) and 4 M HCl in 1,4-dioxane (3 mL) overnight. The reaction mixture was concentrated under reduced pressure, yielding 261 mg (>100% crude) of the desired product as a dark orange solid. The material was used without purification. MS (ESI) m/z 766.38 (M+H).

Synthesis of S11-5-1

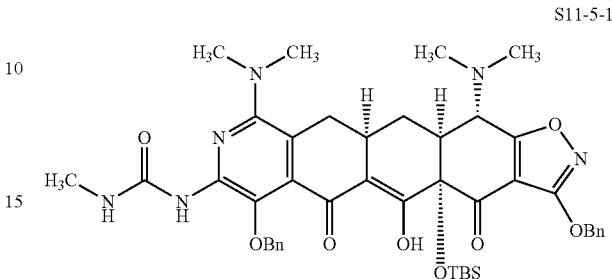

S11-5-1

Methylisocyanate (0.0032 mL, 0.056 mmol) was added to a solution of intermediate S11-4-1 (23.3 mg, 0.028 mmol) in THF (1 mL). After 1 h, additional methylisocyanate was added, and the reaction mixture was heated to 50° C. After heating overnight, additional methylisocyanate was added and heating was continued. After 1 h, the reaction mixture was cooled to rt and was concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 80→100% B; mass-directed fraction collection], yielding 10.9 mg (47%) of the desired product contaminated with ~20% of the starting amine, S11-4-1. $^1$H NMR (400 MHz, CDCl$_3$) δ 15.64 (s, 0.2H), 15.52 (s, 0.8H), 9.10 (s, 0.8H), 7.58-7.24 (m, 10H), 5.36 (s, 2H), 4.98-4.78 (m, 2H), 4.02-3.98 (m, 1H), 3.00-2.75 (m, 11H), 2.62-2.40 (m, 9H), 2.20-2.10 (m, 1H), 0.80 (s, 9H), 0.26 (s, 3H), 0.12 (s, 3H); MS (ESI) m/z 823.51 (M+H).

Compound 142

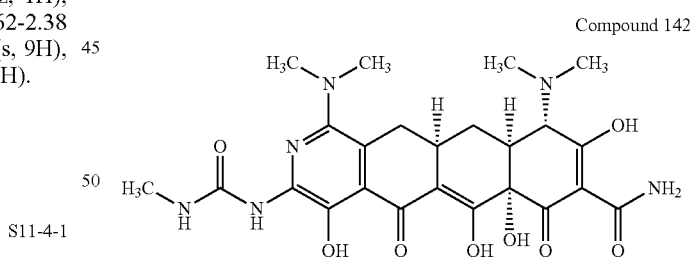

Compound 142

Aqueous HF (0.4 mL, 48%) was added to a solution of S11-5-1 (10.9 mg, 0.013 mmol) in CH$_3$CN (0.6 mL) in a plastic vial. After 18 h, the reaction mixture was poured into a solution of K$_2$HPO$_4$ (4.8 g) in water (15 mL). The mixture was extracted with EtOAc (3×15 mL), and the combined extracts were dried over Na$_2$SO$_4$, filtered and concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH$_3$CN; gradient: 0→100% B; mass-directed fraction collection]. Fractions with the desired MW were collected and freeze-dried to yield 3.4 mg (36%, 2 steps) of the desired desilylated intermediate as a yellow solid. The material was dissolved in methanol (2 mL), 0.5 M HCl in methanol (0.2 mL), and 1,4-dioxane (2 mL), and palladium on carbon (Degussa, 10 wt %, ~2 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 2.5 mg (86%) of Compound 142 as a yellow solid. $^1$H NMR (400 MHz, $CD_3OD$ with 1 drop DCl) δ 4.20 (s, 1H), 3.35-3.15 (m, 6H), 3.14-2.90 (m, 12H), 2.56-2.45 (m, 1H), 2.40-2.32 (m, 1H), 1.71-1.60 (m, 1H); MS (ESI) m/z 531.44 (M+H).

Synthesis of S11-4-2

S11-4-2

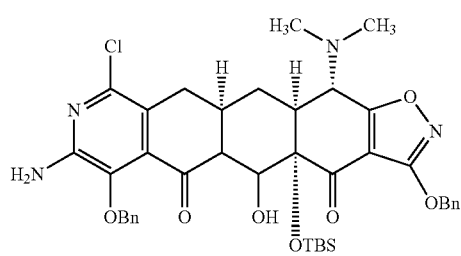

Intermediate S5-2-19 (113.7 mg, 0.133 mmol) was stirred in 4 M HCl in 1,4-dioxane (3 mL) and 1,4-dioxane (1 mL) for 1 h. The reaction mixture was concentrated under reduced pressure. The material was used without further purification or characterization. MS (ESI) m/z 757.30 (M+H).

Synthesis of S11-5-2

S11-5-2

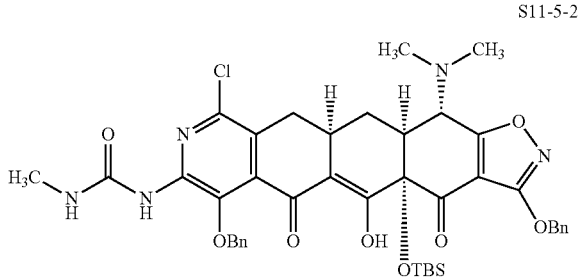 [SMILES: CNC(=O)Nc1nc(Cl)c2c(c1OCc1ccccc1)C(=O)C1=C(O)[C@]3(O[Si](C)(C)C(C)(C)C)C(=O)c4c(OCc5ccccc5)noc4[C@@H](N(C)C)[C@@H]3C[C@@H]1C2]

Methylsiocyanate (19 mg, 0.033 mmol) was added to a solution of intermediate S11-4-2 (27 mg, 0.33 mmol) in THF (1 mL), and the reaction mixture was heated to 50° C. After heating overnight, the reaction mixture was heated to 70° C. After 4 h, the reaction mixture was heated to 90° C. After stirring overnight, the reaction mixture was concentrated under reduced pressure and was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 70→100% B; mass-directed fraction collection]. This gave 14.4 mg of the desired product S11-5-2 mixed with un-reacted intermediate S11-4-2. The material was used directly in the next step. MS (ESI) m/z 814.41 (M+H).

Compound 143

Compound 143

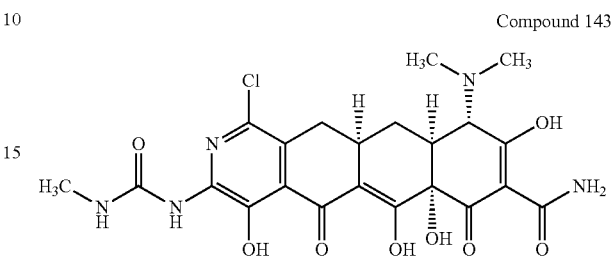

Aqueous HF (0.4 mL, 48%) was added to a solution of S11-5-2 (14.4 mg, 0.018 mmol) in $CH_3CN$ (0.8 mL) in a plastic vial. After 18 h, the reaction mixture was poured into a solution of $K_2HPO_4$ (4.8 g) in water. The mixture was extracted with EtOAc. The combined EtOAc extracts were dried over $Na_2SO_4$, filtered and concentrated under reduced pressure. The material was dissolved in methanol (1 mL), 1,4-dioxane (1 mL) and 0.5 M HCl in methanol (0.1 mL), and palladium on carbon (Degussa, 10 wt %, ~5 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried. The material was re-purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 10→50% B; mass-directed fraction collection]. Fractions with the desired MW were collected and freeze-dried to yield 3.3 mg (33%, 2 steps) of Compound 143 as a yellow solid. $^1$H NMR (400 MHz, $CD_3OD$ with 1 drop DCl) δ 4.19 (s, 1H), 3.20-2.90 (m, 12H), 2.56-2.45 (m, 1H), 2.40-2.32 (m, 1H), 1.71-1.60 (m, 1H); MS (ESI) m/z 522.13 (M+H).

Synthesis of S11-5-3

S11-5-3

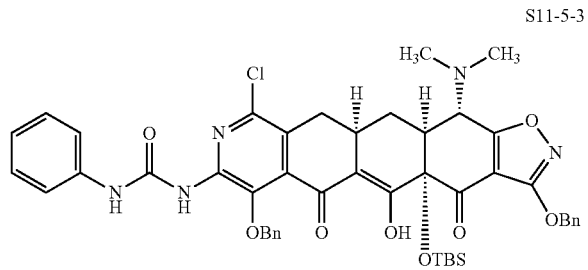 [SMILES: CN(C)[C@@H]1c2onc(OCc3ccccc3)c2C(=O)[C@@]2(O[Si](C)(C)C(C)(C)C)C(O)=C3C(=O)c4c(c(Cl)nc(NC(=O)Nc5ccccc5)c4OCc4ccccc4)C[C@H]3C[C@@H]12]

Phenylisocyanate (0.036 mL, 0.33 mmol) was added to a solution of intermediate S11-4-2 (27 mg, 0.033 mmol) in THF (1 mL), and the reaction mixture was heated to 50° C. After heating overnight, the reaction mixture was heated to 70° C. After 4 h, the reaction mixture was heated to 90° C. After stirring overnight, the reaction mixture was concentrated under reduced pressure and was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 70→100% B; mass-directed fraction collection]. This gave 10.1 mg of the desired product which was used directly in the next step. MS (ESI) m/z 876.43 (M+H).

Compound 131

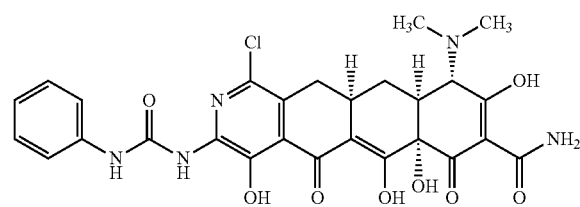

Compound 131

Aqueous HF (0.4 mL, 48%) was added to a solution of S11-5-3 (10.1 mg, 0.0115 mmol) in $CH_3CN$ (0.8 mL) in a plastic vial. After 18 h, the reaction mixture was poured into a solution of $K_2HPO_4$ (4.8 g) in water. The mixture was extracted with EtOAc. The combined EtOAc extracts were dried over $Na_2SO_4$, filtered and concentrated under reduced pressure. The material was dissolved in methanol (1 mL), 1,4-dioxane (1 mL) and 0.5 M HCl in methanol (0.1 mL), and palladium on carbon (Degussa, 10 wt %, ~5 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 3.8 mg (54%, 2 steps) of Compound 131 as a yellow solid. $^1H$ NMR (400 MHz, $CD_3OD$ with 1 drop DCl) δ 7.55-7.45 (m, 2H), 7.40-7.25 (m, 2H), 7.12-7.02 (m, 1H), 4.18 (s, 1H), 3.20-2.90 (m, 9H), 2.38-2.22 (m, 2H), 1.70-1.58 (m, 1H); MS (ESI) m/z 584.28 (M+H).

Synthesis of S11-7-1

S11-7-1

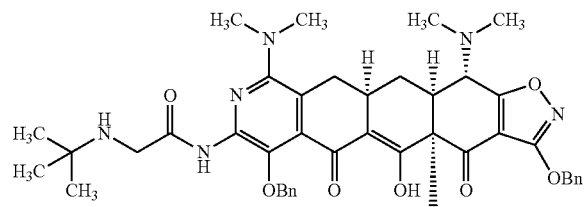

Bromoacetylchloride (11.5 mg, 0.073 mmol) was added to a solution of intermediate S11-4-1 (51 mg, 0.061 mmol) in THF (1 mL). After 2 h, additional bromoacetylchloride was added. After an additional 1 h, t-butylamine (0.064 mL, 0.61 mmol) was added, and the reaction mixture was heated to 50° C. After heating overnight, additional t-butylamine (0.060 mL, 0.57 mmol) was added, and the reaction was heated to 70° C. After 2 h, the reaction mixture was heated to 100° C. (sealed). After 1 h, the reaction mixture was cooled to rt and was concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 50-100% B; mass-directed fraction collection], yielding 23.2 mg (43%) of the desired product as a yellow solid. $^1H$ NMR (400 MHz, $CDCl_3$) δ 15.4 (br s, 1H), 7.52-7.24 (m, 10H), 5.36 (s, 2H), 4.98-4.82 (m, 2H), 4.00 (d, J=11.0 Hz, 1H), 3.02-2.79 (m, 9H), 2.63-2.40 (m, 10H), 2.18 (d, J=14.1 Hz, 1H), 1.40 (br s, 9H), 0.80 (s, 9H), 0.26 (s, 3H), 0.12 (s, 3H); MS (ESI) m/z 879.63 (M+H).

Compound 149

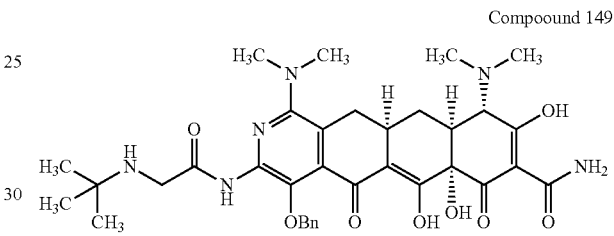

Compoound 149

Aqueous HF (0.4 mL, 48%) was added to a solution of S11-7-1 (23.2 mg, 0.0246 mmol) in $CH_3CN$ (0.8 mL) in a plastic vial. After 18 h, the reaction mixture was poured into a solution of $K_2HPO_4$ (4.8 g) in water. The mixture was extracted with EtOAc, and the combined extracts were dried over $Na_2SO_4$, filtered and concentrated under reduced pressure. The material was dissolved in methanol (2 mL) and 1,4-dioxane (2 mL), and palladium on carbon (Degussa, 10 wt %, ~5 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 9.5 mg (55%, 2 steps) of Compound 149 as a yellow solid. $^1H$ NMR (400 MHz, $CD_3OD$ with 1 drop DCl) δ 4.30-4.40 (m, 3H), 3.40-3.25 (m, 8H), 3.12-3.04 (m, 4H), 2.99 (s, 3H), 2.62-2.52 (m, 1H), 2.41-2.35 (m, 1H), 1.73-1.60 (m, 1H), 1.45 (s, 9H); MS (ESI) m/z 587.43 (M+H).

Synthesis of S11-1-2

S11-1-2

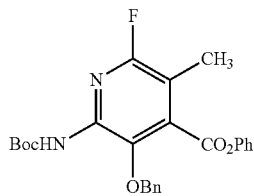

Intermediate S8-5 (538 mg, 1.29 mmol), t-butylcarbamate (302 mg, 2.58 mmol), Cs$_2$CO$_3$ (840 mg, 2.58 mmol), tris(dibenzylideneacetone)dipalladium (59 mg, 0.065 mmol) and 9,9-dimethyl-4,5-bis-(diphenylphosphino)xanthene (109 mg, 0.190 mmol) were weighed into a flask. This was evacuated and back-flushed with nitrogen (3×), and 1,4-dioxane (3 mL) was added. The reaction mixture was heated to 80° C. After 4 h, the reaction mixture was cooled to rt, was diluted with EtOAc (50 mL) and was washed with water (2×25 mL). The organics were dried over Na$_2$SO$_4$, filtered, and concentrated under reduced pressure. The material was purified by column chromatography (Biotage 20 g column, 0 to 12% EtOAc in hexanes gradient), yielding 451 mg (77%) of the product. R$_f$=0.35 in 20% EtOAc/hexanes; $^1$H NMR (400 MHz, CDCl$_3$) δ 7.42-7.24 (m, 8H), 7.04-6.99 (m, 2H), 4.99 (s, 2H), 2.38 (s, 3H), 1.40 (s, 18H); MS (ESI) m/z 453.14 (M+H).

Synthesis of S11-2-2

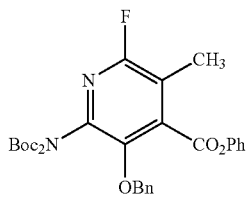

S11-2-2

Intermediate S11-2-1 (451 mg, 1.00 mmol) was treated with d-t-butyldicarbonate (1.09 g, 5.00 mmol) and 4-dimethylaminopyridine (24 mg, 0.20 mmol) in DMF (15 mL). After 30 min, the reaction mixture was diluted with EtOAc (100 mL) and was washed with water (3×50 mL) and brine (50 mL). The organics were dried over Na$_2$SO$_4$, filtered, and concentrated under reduced pressure. The material was purified by column chromatography (Biotage 10 g column, 0 to 8% EtOAc in hexanes gradient), yielding 481 mg (87%) of the product. R$_f$=0.16 in 10% EtOAc/hexanes; $^1$H NMR (400 MHz, CDCl$_3$) δ 7.42-7.24 (m, 8H), 7.04-6.99 (m, 2H), 4.99 (s, 2H), 2.38 (s, 3H), 1.40 (s, 18H); MS (ESI) m/z 575.25 (M+Na).

Synthesis of S11-3-2

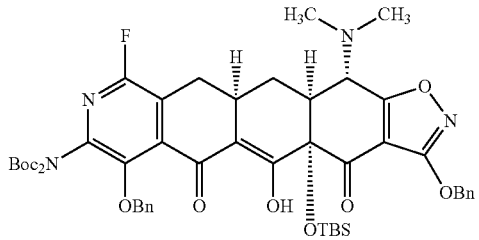

S11-3-2

LHMDS solution (1.0 M, 2.6 mL, 2.6 mmol) was added over ~1 min to a −78° C. solution of intermediate S11-2-2 (480 mg, 0.868 mmol) and S3-1 (418 mg, 0.867 mmol) in THF (8 mL). After 1 h, the reaction mixture was allowed to slowly warm to −10° C. over 1 hr. The reaction mixture was quenched by the addition of NH$_4$Cl (saturated, aqueous solution, 15 mL) and was extracted with EtOAc (20 mL). The extracts were washed with water (15 mL) and were dried over Na$_2$SO$_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 80→100% B; mass-directed fraction collection], yielding 459 mg (56%) of the desired product as a yellow solid. $^1$H NMR (400 MHz, CDCl$_3$) δ 15.59 (s, 1H), 7.56-7.24 (m, 10H), 5.36 (s, 2H), 4.92 (q, J=67.8 Hz, J=9.16 Hz, 2H), 3.91 (d, J=11.0 Hz, 1H), 3.20-3.02 (m, 2H), 2.62-2.45 (m, 9H), 2.19-2.12 (m, 1H), 1.37, (s, 18H), 0.82 (s, 9H), 0.26 (s, 3H), 0.13 (s, 3H); MS (ESI) m/z 941.59 (M+H).

Synthesis of S11-4-3

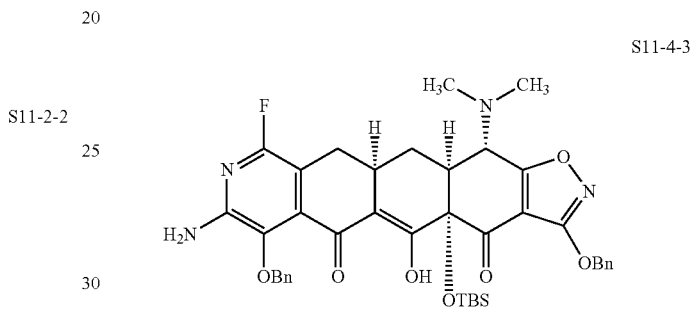

S11-4-3

Intermediate S11-3-2 (459 mg, 0.488 mmol) was stirred in 1,4-dioxane (5 mL) and 4 M HCl in 1,4-dioxane (5 mL) overnight. The reaction mixture was concentrated under reduced pressure, yielding 389 mg (98%) of the desired product as a yellow solid. The material was used without purification. MS (ESI) m/z 742.23 (M+H).

Compound 125

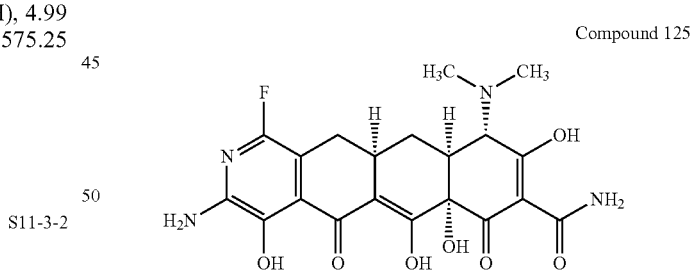

Compound 125

Aqueous HF (0.4 mL, 48%) was added to a solution of S11-4-3 (15 mg, 0.018 mmol) in CH$_3$CN (0.6 mL) in a plastic vial. After 18 h, the reaction mixture was poured into a solution of K$_2$HPO$_4$ (4.8 g) in water. The mixture was extracted with EtOAc, and the combined extracts were dried over Na$_2$SO$_4$, filtered and concentrated under reduced pressure. The material was dissolved in methanol (1 mL), 0.5 M HCl in methanol (0.2 mL) and 1,4-dioxane (1 mL), and palladium on carbon (Degussa, 10 wt %, ~5 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 0→100% B; mass-directed fraction collection]. Fractions with the desired MW were collected and freeze-dried to yield 4.4 mg (49%, 2 steps) of Compound 125 as a yellow solid. $^1$H NMR (400 MHz, CD₃OD with 1 drop DCl) δ 4.20 (s, 1H), 3.40-2.90 (m, 9H), 2.42-2.22 (m, 2H), 1.70-1.54 (m, 1H); MS (ESI) m/z 449.27 (M+H).

Synthesis of S11-7-2

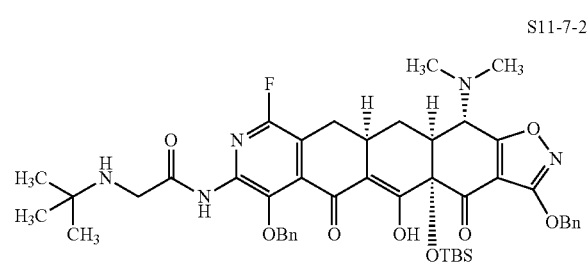 [SMILES: CN(C)[C@@H]1c2onc(OCc3ccccc3)c2C(=O)[C@@]2(O[Si](C)(C)C(C)(C)C)C(O)=C3C(=O)c4c(c(F)nc(NC(=O)CNC(C)(C)C)c4OCc4ccccc4)C[C@H]3C[C@@H]12]

S11-7-2

Bromoacetylbromide (0.008 mL, 0.09 mmol) was added to a solution of intermediate S11-4-3 (50 mg, 0.061 mmol) in THF (1 mL). After 1.5 h, t-butylamine (0.032 mL, 0.31 mmol) was added. After 1 h, the reaction mixture was concentrated under reduced pressure. The material was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 50→100% B; mass-directed fraction collection], yielding 35.4 mg (68%) of the desired product as a yellow solid. $^1$H NMR (400 MHz, CDCl₃) δ 15.6 (br s, 1H), 7.51-7.48 (m, 2H), 7.42-7.30 (m, 8H), 5.36 (s, 2H), 4.94 (q, J=23.2 Hz, J=10.4 Hz, 2H), 3.89 (d, J=11.0 Hz, 1H), 3.17-3.02 (m, 2H), 2.63-2.58 (m, 1H), 2.56-2.40 (m, 10H), 2.15 (d, J=14.1 Hz, 1H), 1.07 (br s, 9H), 0.82 (s, 9H), 0.26 (s, 3H), 0.13 (s, 3H); MS (ESI) m/z 854.51 (M+H).

Compound 120

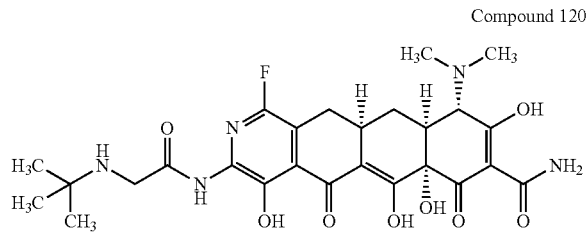 [SMILES: CN(C)[C@@H]1C(O)=C(C(N)=O)C(=O)[C@@]2(O)C(O)=C3C(=O)c4c(O)c(NC(=O)CNC(C)(C)C)nc(F)c4C[C@H]3C[C@@H]12]

Compound 120

Aqueous HF (0.4 mL, 48%) was added to a solution of S11-7-2 (35.4 mg, 0.0414 mmol) in CH₃CN (0.8 mL) in a plastic vial. After 18 h, the reaction mixture was poured into a solution of K₂HPO₄ (4.8 g) in water. The mixture was extracted with EtOAc, and the combined extracts were dried over Na₂SO₄, filtered and concentrated under reduced pressure. The material was dissolved in methanol (1 mL), 0.5 M HCl in methanol (0.2 mL) and 1,4-dioxane (1 mL), and palladium on carbon (Degussa, 10 wt %, ~5 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 0→100% B; mass-directed fraction collection]. Fractions with the desired MW were collected and freeze-dried to yield 15.3 mg (58%, 2 steps) of the desired product as a yellow solid. $^1$H NMR (400 MHz, CD₃OD with 1 drop DCl) δ 4.24-4.65 (m, 3H), 3.26-2.97 (m, 9H), 2.38-2.28 (m, 2H), 1.69-1.56 (m, 1H), 1.44 (s, 9H); MS (ESI) m/z 562.37 (M+H).

The following Compounds were prepared similarly to Compound 120 above:

Compound 163

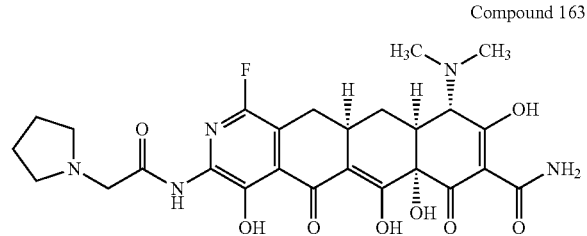 [SMILES: CN(C)[C@@H]1C(O)=C(C(N)=O)C(=O)[C@@]2(O)C(O)=C3C(=O)c4c(O)c(NC(=O)CN5CCCC5)nc(F)c4C[C@H]3C[C@@H]12]

Compound 163

$^1$H NMR (400 MHz, CD₃OD with 1 drop DCl) δ 4.58-4.48 (m, 2H), 4.20 (s, 1H), 3.86-3.77 (m, 2H), 3.34-3.14 (m, 2H), 3.14-2.97 (m, 9H), 2.38-2.28 (m, 2H), 2.26-2.02 (m, 4H), 1.70-1.56 (m, 1H); MS (ESI) m/z 560.34 (M+H).

Compound 100

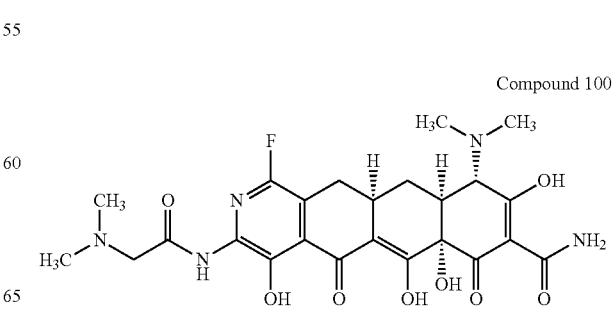

Compound 100

¹H NMR (400 MHz, CD₃OD with 1 drop DCl) δ 4.50-4.40 (m, 2H), 4.19 (s, 1H), 3.14-3.01 (m, 12H), 2.98 (s, 3H), 2.39-2.28 (m, 2H), 1.69-1.57 (m, 1H); MS (ESI) m/z 534.33 (M+H).

Compound 132

¹H NMR (400 MHz, CD₃OD with 1 drop DCl) δ 4.30-4.20 (s, 2 μl), 4.19 (s, 1H), 3.25-2.96 (m, 9H), 2.48-2.28 (m, 2H), 1.72-1.58 (m, 1H), 1.43 (s, 9 μl); MS (ESI) m/z 578.48 (M+H).

Example 12

Preparation of Compounds of Formula I, wherein X is Hydrogen, Y is Cl or Hydrogen, and Z is —(C₁-C₆) alkylene-N(R⁵)(R⁶)

Compounds of Formula I, wherein X is hydrogen, Y is Cl or hydrogen, and Z is —(C₁-C₆) alkylene-N(R⁵)(R⁶) (as well as compounds of Formula II, wherein Z is —(C₁-C₆) alkylene-N(R⁵)(R⁶)) were prepared according to Scheme 12.

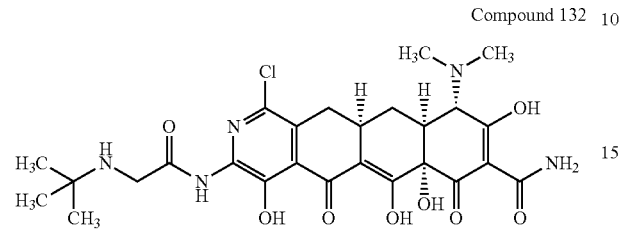

Compound 132

Scheme 12

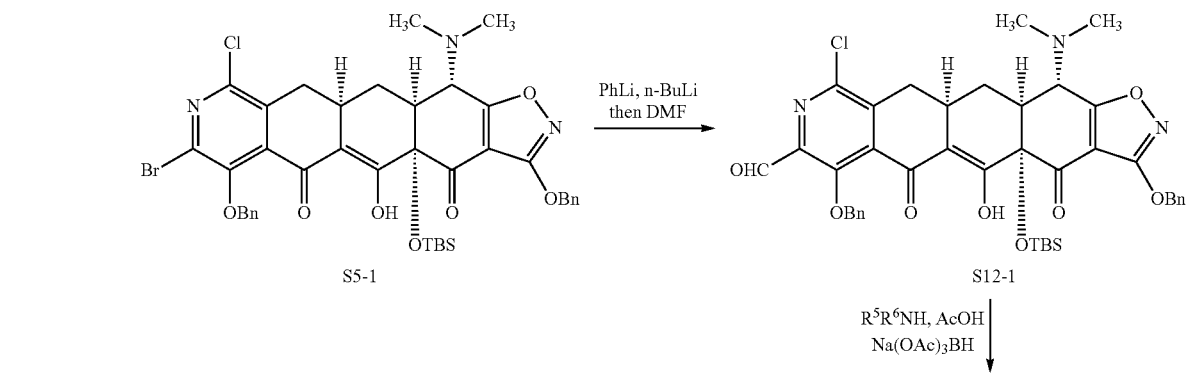

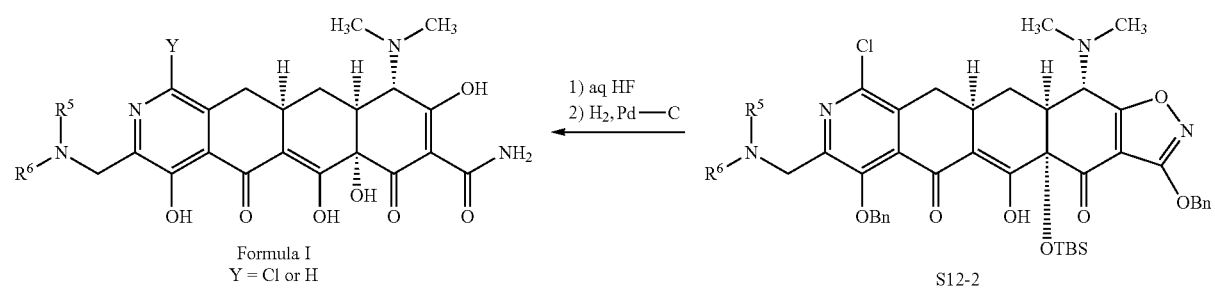

The following specific intermediates and compounds of the invention were prepared according to Scheme 12.

Synthesis of S12-1

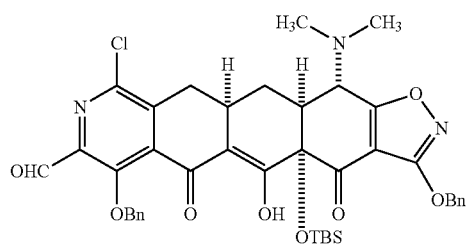

S12-1

A solution of phenyllithium (0.384 mL, 1.8 M in di-n-butyl ether, 0.69 mmol) was added drop wise to a solution of intermediate S5-1 (284 mg, 0.345 mmol, 1.0 equiv) in THF (4 mL) at −78° C., forming an orange solution. After 1 min, a solution of n-butyllithium (216 μL, 1.6 M in hexanes, 0.345 mmol) was added drop wise at −78° C., followed 2 min later by the addition of N,N-dimethylformamide (133 μL, 1.73 mmol). The resulting dark red reaction mixture was stirred at −78° C. for 30 min and was then warmed to −40° C. and stirred for one hr. Ammonium chloride (saturated, aqueous solution, 10 mL) was added drop wise at −40° C. The reaction mixture was allowed to warm to 25° C., was diluted with ammonium chloride (saturated, aqueous solution), and was extracted with EtOAc (2×25 mL). The organic extracts were combined, dried over anhydrous sodium sulfate, filtered, and concentrated, affording 239 mg of the crude product as a yellow oil: MS (ESI) m/z 770.67 (M+H). This was used directly in the next reactions.

Synthesis of S12-2-1

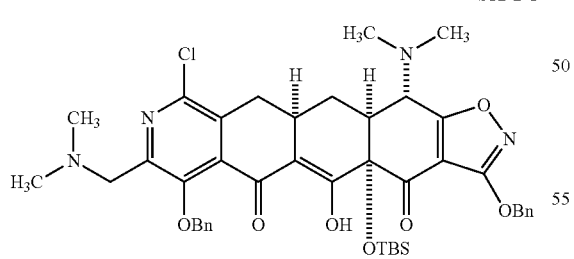

S12-2-1

Dimethylamine (179 μL, 1.0 mmol), acetic acid (57.2 μL, 1.0 mmol) and sodium triacetoxyborohydride (212 mg, 1.0 mmol) were added sequentially to a solution of intermediate S12-1 (80 mg, 0.1 mmol) in methylene chloride (2 mL) at 25° C. After stirring overnight, the reaction mixture was quenched by the addition of saturated aqueous sodium bicarbonate and brine (1:1, 15 mL) and was extracted with methylene chloride (2×15 mL). The combined organic extracts were dried over anhydrous sodium sulfate, filtered, and concentrated to yield the crude product: MS (ESI) m/z 799.57 (M+H).

Compound 128

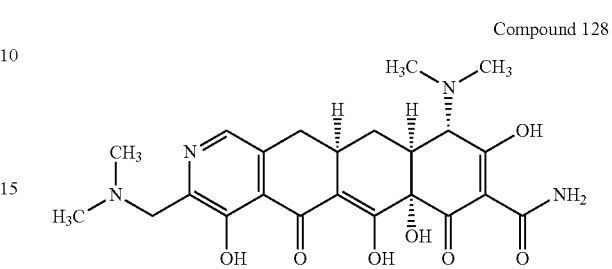

Compound 128

Aqueous HF (48-50%, 0.6 mL) was added to a solution of intermediate S12-2-1 (59 mg, crude) in acetonitrile (3 mL) in a polypropylene reaction vessel at 25° C. The mixture was stirred vigorously at 25° C. overnight and was poured into a solution of K$_2$HPO$_4$ (4.0 g) in water (20 mL). The mixture was extracted with EtOAc (3×25 mL). The combined organic extracts were dried over anhydrous sodium sulfate, filtered, and concentrated. Pd—C (10 wt %, 5 mg) was added in one portion into the yellow solution of the above crude product in a mixture of 1,4-dioxane (2 mL) and methanol (2 mL) at 25° C. The reaction vessel was sealed and purged with hydrogen by briefly evacuating the flask followed by flushing with hydrogen gas (1 atm). The resulting mixture was stirred at 25° C. for 2 hr. The reaction mixture was then filtered through a small Celite pad. The filtrate was concentrated. The residue was purified by preparative reverse phase HPLC on a Waters Autopurification system using a Phenomenex Polymerx 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water); gradient: 0→100% B over 10 min; mass-directed fraction collection]. Fractions containing the desired product were collected and freeze-dried to yield Compound 128 (3.6 mg, 6.6% for 4 steps): $^1$H NMR (400 MHz, CD$_3$OD) δ 8.19 (s, 1H), 4.54 (s, 2H), 4.12 (s, 1H), 3.08-2.92 (m, 15H), 2.64-2.54 (m, 1H), 2.30-2.22 (m, 1H), 1.70-1.60 (m, 1H); MS (ESI) m/z 473.39 (M+H).

The following compounds were prepared similarly to Compound 128 using the appropriate amine in place of dimethylamine:

Compound 161

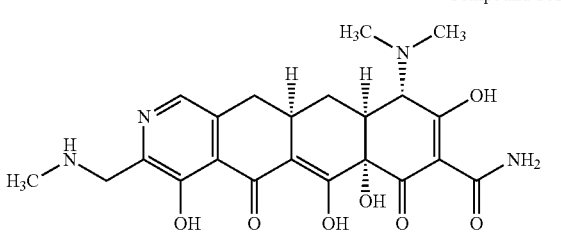

Compound 161

¹H NMR (400 MHz, CD₃OD) δ 8.17 (s, 1H), 4.53 (m, 2H), 4.12 (s, 1H), 3.08-2.92 (m, 9H), 2.83 (s, 3H), 2.32-2.08 (m, 2H), 1.70-1.60 (m, 1H); MS (ESI) m/z 459.36 (M+H).

Compound 164

¹H NMR (400 MHz, CD₃OD) δ 8.15 (s, 1H), 4.40 (s, 2H), 4.11 (s, 1H), 3.14-2.90 (m, 11H), 2.30-2.20 (m, 1H), 2.17-2.05 (m, 2H), 1.71-1.57 (m, 1H), 1.06 (d, J=6.4 Hz, 6H); MS (ESI) m/z 501.44 (M+H).

Compound 137

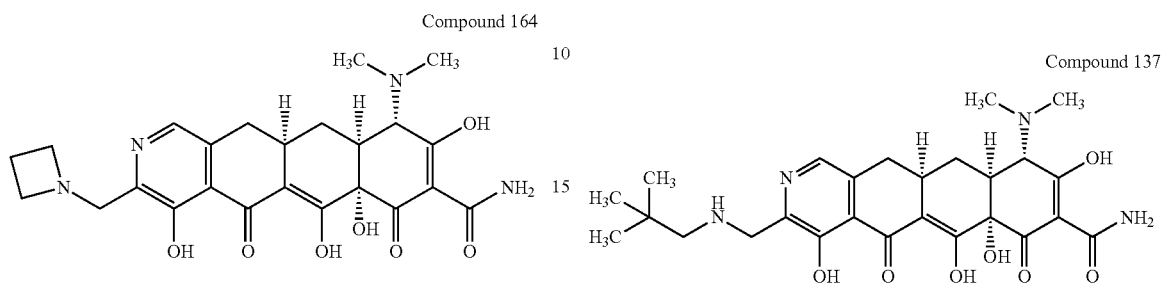

¹H NMR (400 MHz, CD₃OD) δ 8.17 (S, 1H), 4.54 (s, 2 h), 4.25-4.17 (m, 4H), 4.12 (s, 1H), 3.08-2.92 (m, 9H), 2.54-2.39 (m, 2H), 2.30-2.22 (m, 2H), 1.70-1.60 (m, 1H); MS (ESI) m/z 485.44 (M+H).

Compound 116

¹H NMR (400 MHz, CD₃OD) δ 8.34 (s, 1H), 4.50 (s, 2H), 4.11 (s, 1H), 3.14-2.90 (m, 11H), 2.48-2.39 (m, 1H), 2.30-2.22 (m, 1H), 1.69-1.55 (m, 1H), 1.10 (s, 9H); MS (ESI) m/z 515.46 (M+H).

Example 13

Preparation of Compounds of Formula I, wherein X and Z are Hydrogen and Y is $(C_1-C_6)$ alkylene-$N(R^1)(R^2)$ Compounds of Formula I, wherein X and Z are hydrogen and Y is $(C_1-C_6)$ alkylene-$N(R^1)(R^2)$ are synthesized using Scheme 12'.

Scheme 12'

Specific compounds of the invention prepared according to Scheme 12' are described below.

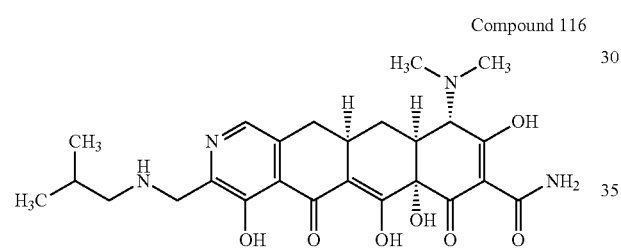

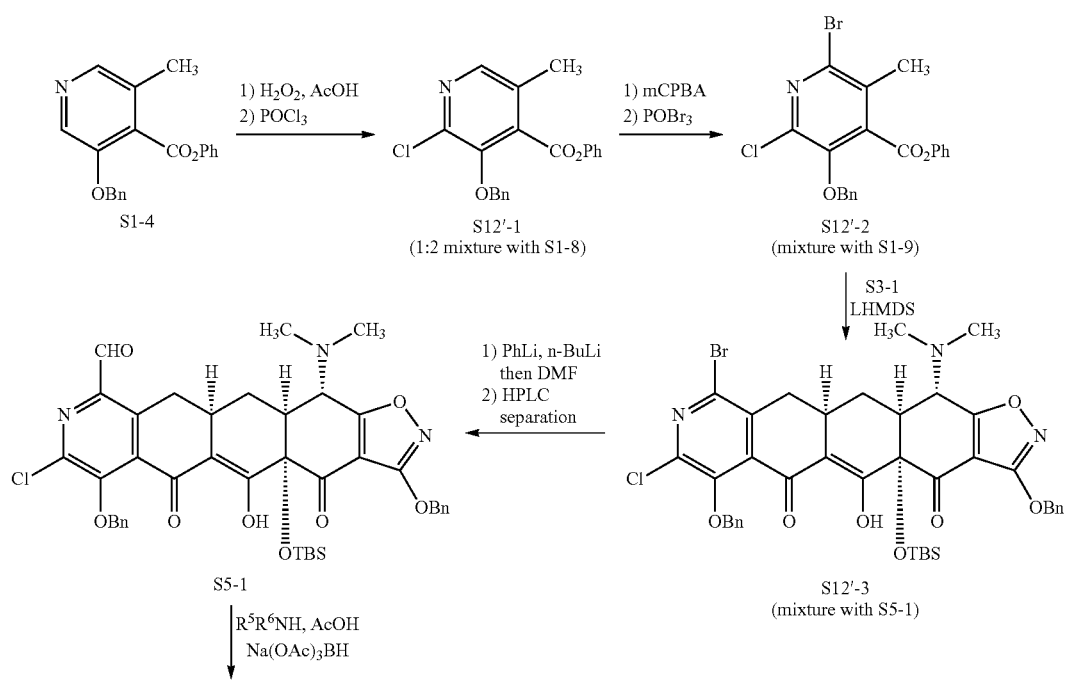

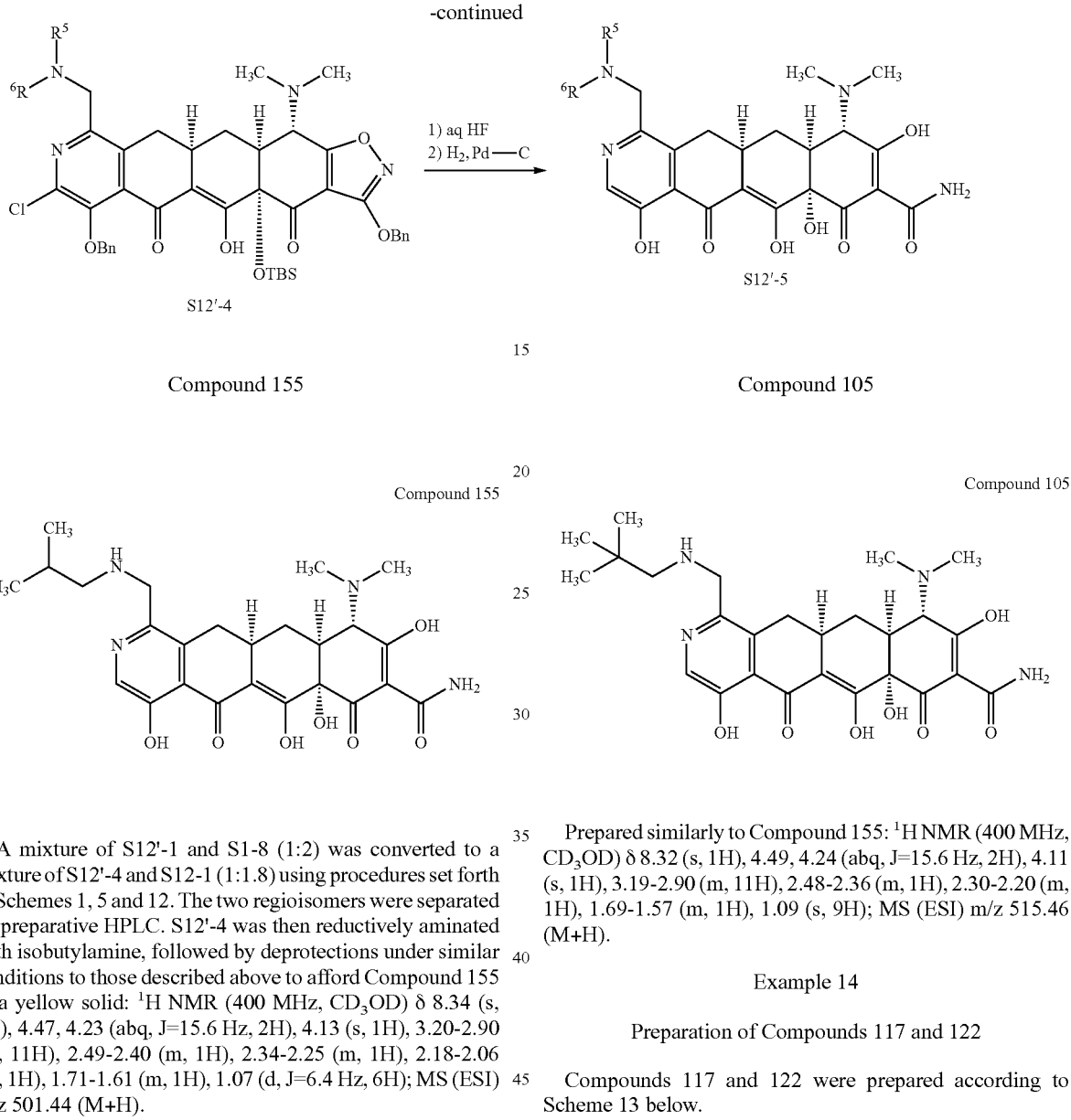

Compound 155

Compound 105

A mixture of S12'-1 and S1-8 (1:2) was converted to a mixture of S12'-4 and S12-1 (1:1.8) using procedures set forth in Schemes 1, 5 and 12. The two regioisomers were separated by preparative HPLC. S12'-4 was then reductively aminated with isobutylamine, followed by deprotections under similar conditions to those described above to afford Compound 155 as a yellow solid: $^1$H NMR (400 MHz, CD$_3$OD) δ 8.34 (s, 1H), 4.47, 4.23 (abq, J=15.6 Hz, 2H), 4.13 (s, 1H), 3.20-2.90 (m, 11H), 2.49-2.40 (m, 1H), 2.34-2.25 (m, 1H), 2.18-2.06 (m, 1H), 1.71-1.61 (m, 1H), 1.07 (d, J=6.4 Hz, 6H); MS (ESI) m/z 501.44 (M+H).

Prepared similarly to Compound 155: $^1$H NMR (400 MHz, CD$_3$OD) δ 8.32 (s, 1H), 4.49, 4.24 (abq, J=15.6 Hz, 2H), 4.11 (s, 1H), 3.19-2.90 (m, 11H), 2.48-2.36 (m, 1H), 2.30-2.20 (m, 1H), 1.69-1.57 (m, 1H), 1.09 (s, 9H); MS (ESI) m/z 515.46 (M+H).

Example 14

Preparation of Compounds 117 and 122

Compounds 117 and 122 were prepared according to Scheme 13 below.

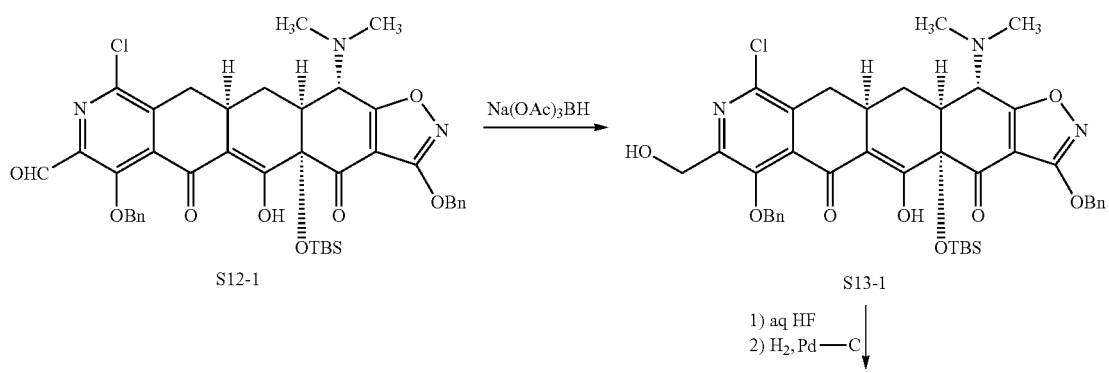

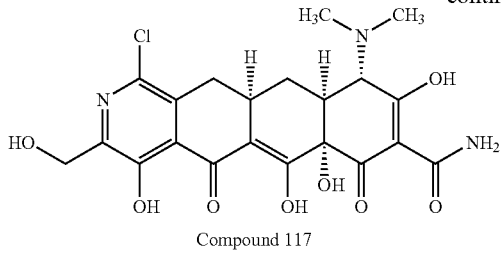

Compound 117

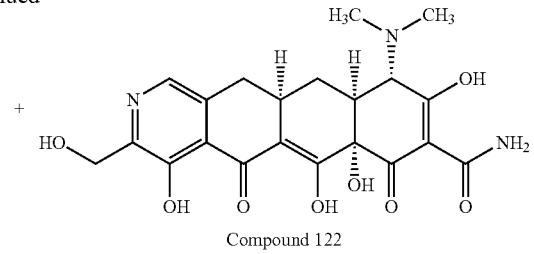

Compound 122

Compound 117

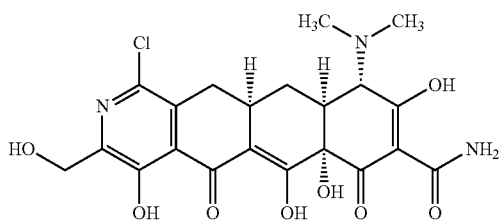

Compound 117

Sodium triacetoxyborohydride (16.5 mg, 0.078 mmol, 2 equiv) was added to a solution of S12-1 (30 mg, 0.039 mmol) in methylene chloride (2 mL) at 25° C. After stirring overnight, the reaction mixture was quenched by the addition of saturated aqueous sodium bicarbonate (10 mL) and was extracted with methylene chloride (2×15 mL). The combined organic extracts were dried over anhydrous sodium sulfate, filtered, and concentrated to give the alcohol intermediate. MS (ESI) m/z 772.51 (M+H). Aqueous HF (48-50%, 0.3 mL) was added to a solution of the intermediate in acetonitrile (1.5 mL) in a polypropylene reaction vessel at 25° C. The mixture was stirred vigorously at 25° C. overnight and poured into aqueous $K_2HPO_4$ (4.0 g dissolved in 20 mL water). The mixture was extracted with EtOAc (3×25 mL). The combined organic extracts were dried over anhydrous sodium sulfate, filtered, and concentrated. Pd—C (10 wt %, 5 mg) was added to a solution of the above crude product in a mixture of 1,4-dioxane (2 mL) and methanol (2 mL). The reaction vessel was sealed and purged with hydrogen by briefly evacuating the flask followed by flushing with hydrogen gas (1 atm). The resulting mixture was stirred at 25° C. for 2 hr. The reaction mixture was then filtered through a small Celite pad. The filtrate was concentrated. The residue was purified by preparative reverse phase HPLC on a Waters Autopurification system using a Phenomenex Polymerx 10μ RP-γ 100 A column [10 μm, 150×21.20 mm; flow rate, 20 mL/min; Solvent A: 0.05 N HCl/water; Solvent B: $CH_3CN$; injection volume: 3.0 mL (0.05 N HCl/water); gradient: 0→100% B over 10 min; mass-directed fraction collection]. Fractions containing the desired product were collected and freeze-dried to yield 4.2 mg (22%, 3 steps) of Compound 117 and 2.2 mg (13%) of Compound 122 as yellow solids. Data for Compound 117: $^1$H NMR (400 MHz, $CD_3OD$) δ 4.70 (s, 2H), 4.10 (s, 1H), 3.15-2.92 (m, 9H), 2.35-2.15 (m, 2H), 1.84-1.70 (m, 1H); MS (ESI) m/z 480.22 (M+H). and des-Cl compound (2.23 mg, 12.8%)

Compound 122

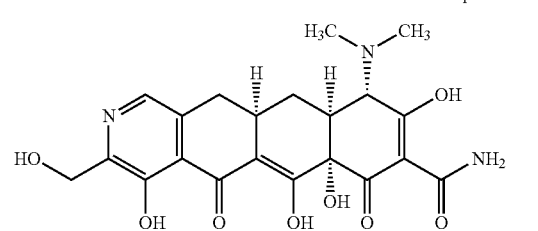

Compound 122

$^1$H NMR (400 MHz, $CD_3OD$) δ 7.68 (s, 1H), 4.15 (s, 1H), 4.04-3.90 (m, 2H), 3.14-2.90 (m, 9H), 2.30-2.12 (m, 2H), 1.80-1.71 (m, 1H); MS (ESI) m/z 446.26 (M+H).

Example 15

Preparation of Compounds of Formula I, wherein X is Hydrogen and Z is $C_1$-$C_6$ alkyl or Phenyl Compounds of Formula I, wherein X is hydrogen and Z is $C_1$-$C_6$ alkyl or phenyl (as well as compounds of Formula II, wherein Z is $C_1$-$C_6$ alkyl or phenyl were prepared according to Scheme 14.

Scheme 14

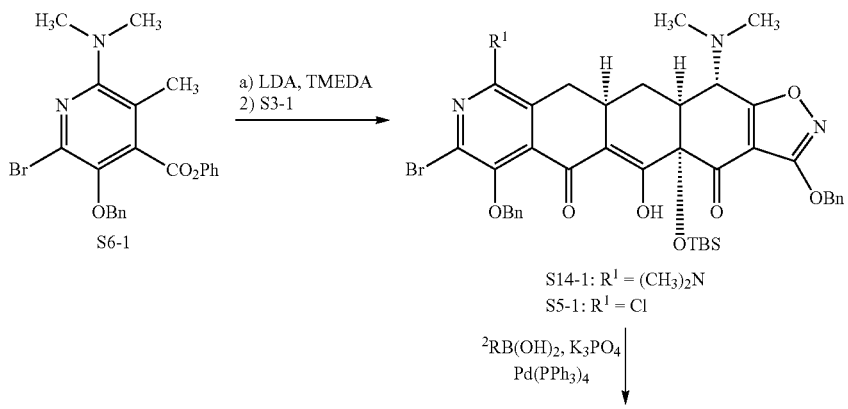

S14-1: $R^1$ = $(CH_3)_2N$
S5-1: $R^1$ = Cl $^2RB(OH)_2$, $K_3PO_4$
$Pd(PPh_3)_4$

101

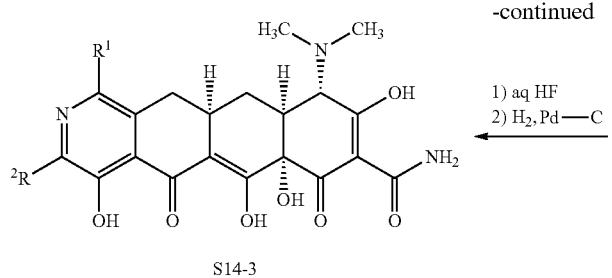

S14-3

1) aq HF
2) H₂, Pd—C

102

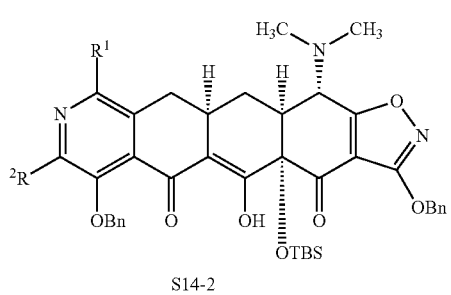

S14-2

Specific intermediates and compounds of the invention prepared by Scheme 14 are described in detail below.

Synthesis of S14-1

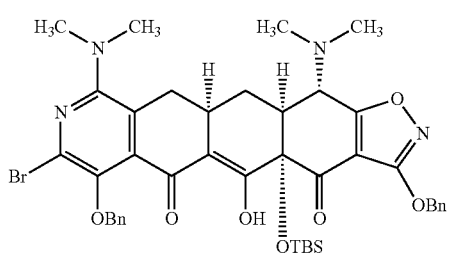

S14-1

Lithium diisopropylamide was prepared at −40° C. by the addition of n-BuLi (2.5 M solution in hexane, 0.60 mL, 0.1.5 mmol) to a solution of diisopropylamine (0.213 mL, 0.151 mmol) in THF (10 mL). The reaction mixture was cooled to −78° C. and TMEDA (0.542 mL, 3.62 mmol) was added. A solution of intermediate S6-1 (266 mg, 0.603 mmol) in THF (4 mL) was added drop wise, giving a dark red colored solution. After 5 min, a solution of S3-1 (242 mg, 0.502 mmol) in THF (2 mL) was added. The reaction mixture was allowed to warm to −20° C. over ~45 min. The reaction mixture was quenched by the addition of NH₄Cl (saturated, aqueous solution) and was extracted with EtOAc (2×). The extracts were dried over Na₂SO₄, filtered, and concentrated under reduced pressure. The material was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 90→100% B; mass-directed fraction collection], yielding 225 mg (54%) of the desired product as a yellow solid. MS (ESI) m/z 829.49, 831.48 (M+H).

Synthesis of S14-2-1

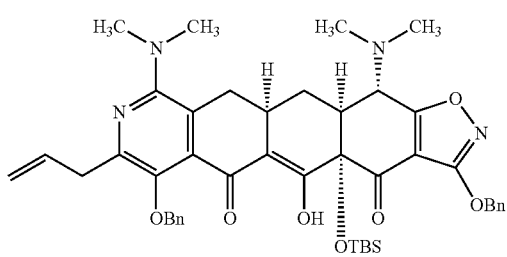

S14-2-1

Intermediate S14-1 (105 mg, 0.126 mmol), tetrakis(triphenyl-phosphine)palladium(0) (15 mg, 0.013 mmol) and potassium phosphate (80 mg, 0.379 mmol) were weighed into an 8 mL vial. This was sealed with a septum and was evacuated and back-flushed with nitrogen (3×). Toluene (1 mL), 1,4-dioxane (1 mL), and water (0.5 mL) were added, followed by allylboronic acid pinacol ester (63.7 mg, 0.379 mmol). The reaction mixture was heated to 90° C. After 2.5 h, the reaction mixture was cooled to rt and was concentrated under reduced pressure. The material was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 90→100% B; mass-directed fraction collection], yielding 28.6 mg (29%) of the desired product as a yellow solid. MS (ESI) m/z 791.64 (M+H).

Compound 141

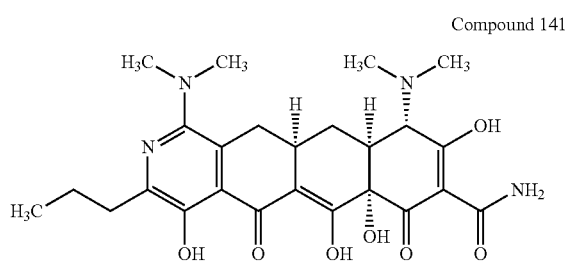 [SMILES: CCCc1nc(N(C)C)c2c(c1O)C(=O)C1=C(O)[C@]3(O)C(=O)C(C(N)=O)=C(O)[C@@H](N(C)C)[C@@H]3C[C@@H]1C2]

Compound 141

Aqueous HF (0.4 mL, 48%) was added to a solution of S14-2-1 (28.6 mg, 0.036 mmol) in 1,4-dioxane (1 mL) in a plastic vial. After 18 h, the reaction mixture was poured into a solution of K₂HPO₄ (4.8 g) in water. The mixture was extracted with EtOAc, and the combined extracts were dried over Na₂SO₄, filtered and concentrated under reduced pressure. The material was dissolved in methanol (1 mL), 0.5 M HCl in methanol (0.5 mL), and 1,4-dioxane (1 mL), and palladium on carbon (Degussa, 10 wt %, ~5 mg) was added. An atmosphere of hydrogen was introduced, and the reaction mixture was stirred for 1 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 0→70% B; mass-directed fraction collection]. Fractions with the desired MW were collected and freeze-dried to yield 14.3 mg (69%) of Compound 141 as a yellow solid. ¹H NMR (400 MHz, CD₃OD with 1 drop DCl) δ 4.20 (s, 1H), 3.38-3.15 (m, 7H), 3.14-2.94 (m, 8H), 2.91-2.82 (m, 2H), 2.56 (t, J=13.8 Hz, 1H), 2.40-2.32 (m, 1H), 1.86-1.76 (m, 2H), 1.74-1.62 (m, 1H), 1.01 (t, J=7.34 Hz, 3H); MS (ESI) m/z 501.35 (M+H).

The following compounds were prepared similarly to Compound 141 utilizing the appropriate starting materials and alkyl or aryl boronic acids.

Compound 104

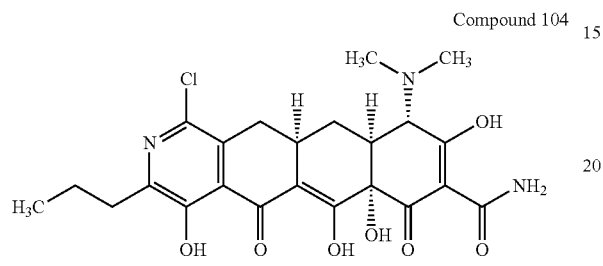

Compound 104

$^1$H NMR (400 MHz, CD$_3$OD) δ 4.10 (s, 1H), 3.22-2.92 (m, 9H), 2.81-2.74 (m, 2H), 2.49-2.38 (m, 1H), 2.26-2.19 (m, 1H), 1.77-1.60 (m, 3H), 0.97 (t, J=7.3 Hz, 3H); MS (ESI) m/z 492.27 (M+H).

Compound 103

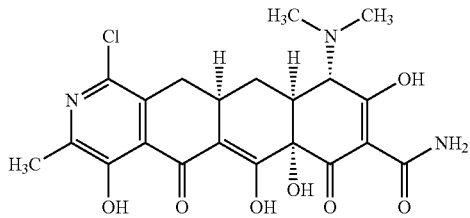

Compound 103

$^1$H NMR (400 MHz, CD$_3$OD) δ 4.09 (s, 1H), 3.22-2.92 (m, 9H), 2.85 (s, 3H), 2.49-2.38 (m, 1H), 2.26-2.19 (m, 1H), 1.77-1.60 (m, 1H); MS (ESI) m/z 464.30 (M+H).

Compound 158

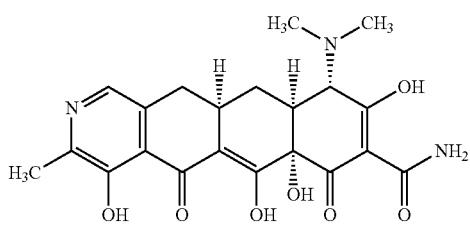

Compound 158

Isolated as a side-product in the synthesis of Compound 103. $^1$H NMR (400 MHz, CD$_3$OD) δ 7.78 (s, 1H), 4.12 (s, 1H), 3.22-2.91 (m, 9H), 2.78 (s, 3H), 2.49-2.21 (m, 1H), 1.77-1.62 (m, 1H); MS (ESI) m/z 430.46 (M+H).

Compound 136

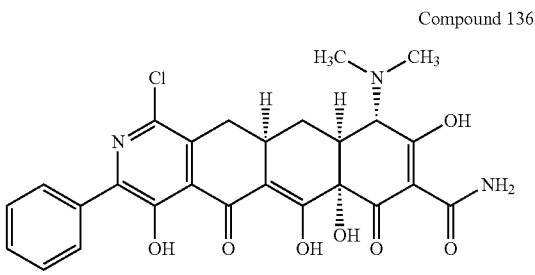 [SMILES: CN(C)[C@@H]1C(O)=C(C(N)=O)C(=O)[C@@]2(O)C(O)=C3C(=O)c4c(O)c(-c5ccccc5)nc(Cl)c4C[C@H]3C[C@@H]12]

Compound 136

$^1$H NMR (400 MHz, CD$_3$OD) δ 8.04-7.98 (m, 2H), 7.47-7.39 (m, 3H), 4.08 (s, 1H), 3.14-2.92 (m, 9H), 2.57-2.47 (m, 1H), 2.28-2.07 (m, 1H), 1.73-1.65 (m, 1H); MS (ESI) m/z 526.26 (M+H).

Compound 165

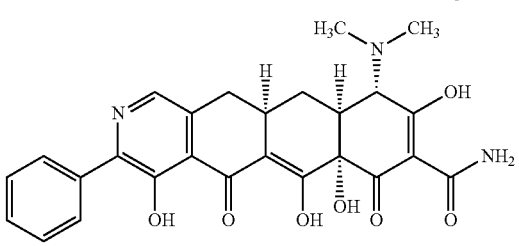

Compound 165

Compound 165 is isolated as a side-product in the synthesis of Compound 136. $^1$H NMR (400 MHz, CD$_3$OD) δ 8.29 (s, 1H), 7.98-7.81 (m, 2H), 7.47-7.32 (m, 3H), 4.07 (s, 1H), 3.14-2.92 (m, 9H), 2.61-2.49 (m, 1H), 2.28-2.18 (m, 1H), 1.78-1.65 (m, 1H); MS (ESI) m/z 492.30 (M+H).

Example 16

Preparation of Compound 145

Compound 145 is prepared according to Scheme 15.

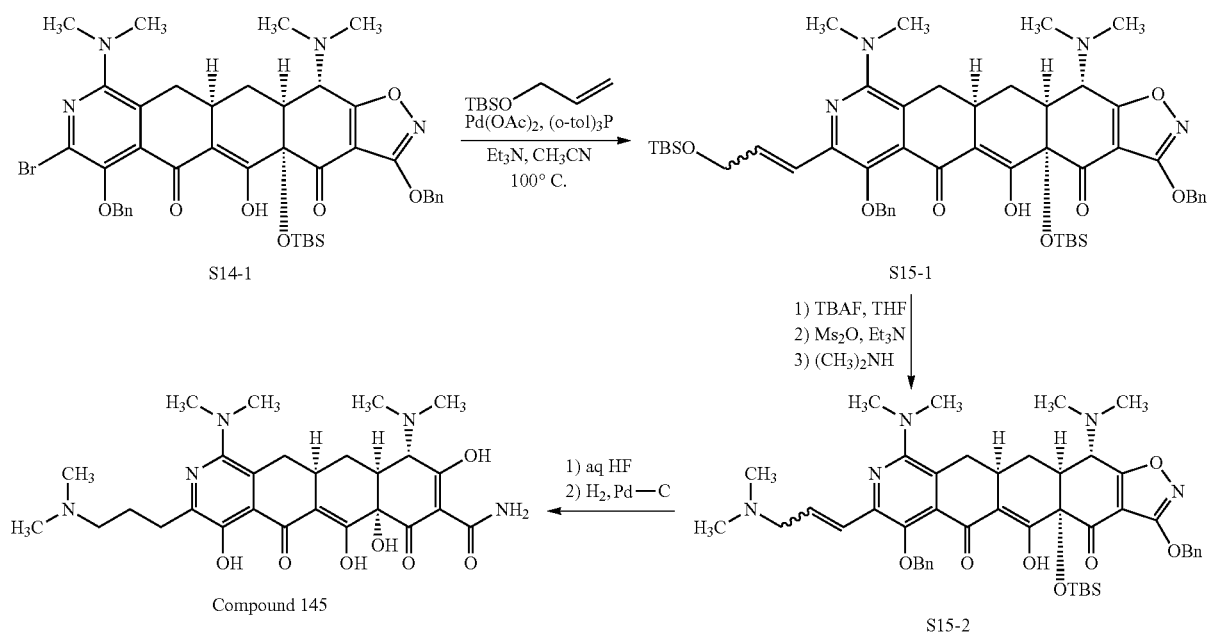

Scheme 15

Synthesis of S15-1

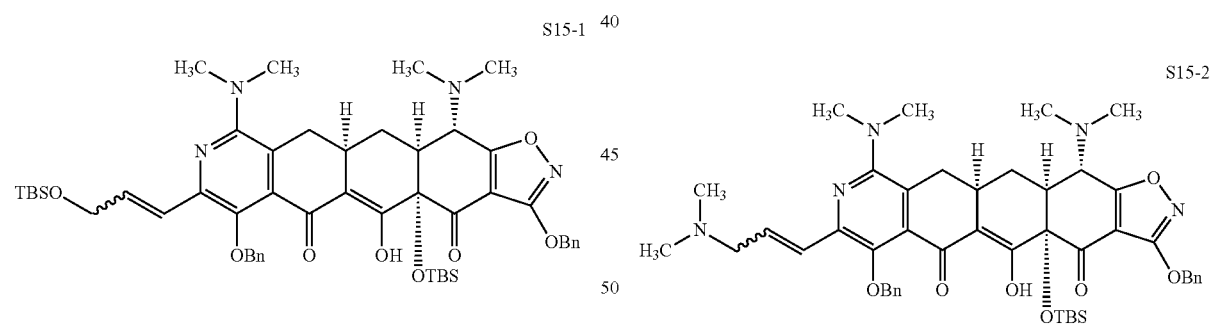

Intermediate S14-1 (95.7 mg, 0.115 mmol), Pd(OAc)$_2$ (2.7 mg, 0.012 mmol) and tri-(o-tolyl)phosphine (7.0 mg, 0.023 mmol) were weighed into an 8 mL vial. This was sealed with a septum and was evacuated and back-flushed with nitrogen (3×). Acetonitrile (2 mL), triethylamine (0.080 mL, 0.58 mmol), and allyloxy-t-butyldimethylsilane (0.049 mL, 0.23 mmol) were added. The reaction mixture was heated to 100° C. After 4 h, the reaction mixture was cooled to rt, was filtered through Celite, and was concentrated under reduced pressure. The material was purified on a Waters Autopurification system equipped with a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; gradient: 100→100% B; mass-directed fraction collection], yielding 55.5 mg (52%) of a mixture of the products as a yellow solid.

$^1$H NMR (400 MHz, CDCl$_3$) δ 15.6-15.5 (m, 1H), 7.92 (s, 1H), 7.45-7.24 (m, 10H), 6.22-5.98 (m, 0.3H), 5.27 (s, 2H), 4.86-4.78 (m, 1H), 4.78-4.50 (m, 1.3H), 4.36-4.30 (m, 0.7H), 3.98 (d, J=11.0 Hz, 1H), 3.65-3.55 (m, 0.7H), 2.98-2.88 (m, 1H), 2.87-2.55 (m, 8H), 2.54-2.30 (m, 9H), 2.11-2.04 (m, 1H), 0.84 (s, 9H), 0.71 (s, 9H), 0.17 (s, 3H), 0.06-0.05 (m, 9H); MS (ESI) m/z 921.74 (M+H).

Synthesis of S15-2

Tetrabutylammonium fluoride (1.0 M solution in THF, 1 mL, 1 mmol) was added to a solution of intermediate S15-1 (55 mg, 0.060 mmol) in THF (1 mL). After 1 h, the reaction mixture was concentrated under reduced pressure. The material was dissolved in EtOAc and was washed with water (3×) and brine. The material was dried over Na$_2$SO$_4$, filtered and concentrated under reduced pressure. The crude alcohol was dissolved in THF (2 mL) and methanesulfonic anhydride (10 mg, 0.060 mmol) and triethylamine (0.084 mL, 0.060 mmol) were added. After 30 min, an additional portion of methanesulfonic anhydride (10 mg, 0.060 mmol) was added. After 30 min, dimethylamine (2.0 M solution in THF (0.3 mL, 0.6 mmol) was added. After 30 min, the reaction mixture was concentrated under reduced pressure and was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 50→100% B; mass-directed fraction collection], yielding 14 mg (28%) of the desired product as a yellow solid. $^1$H NMR (400 MHz, CDCl$_3$) δ 15.25 (s, 1H), 7.52-7.46 (m, 2H), 7.42-7.24 (m, 8H), 6.98-6.92 (m, 1H), 6.88-6.78 (m, 1H), 5.36 (s, 2H), 4.90-4.75 (m, 2H), 4.08-4.00 (m, 1H), 3.75-3.66 (m, 2H), 3.06-3.00 (m, 1H), 2.84 (s, 6H), 2.82-2.70 (m, 8H), 2.65-2.40 (m, 8H), 2.21-2.13 (m, 1H), 0.79 (s, 9H), 0.26 (s, 3H), 0.11 (s, 3H); MS (ESI) m/z 834.70 (M+H).

Compound 145

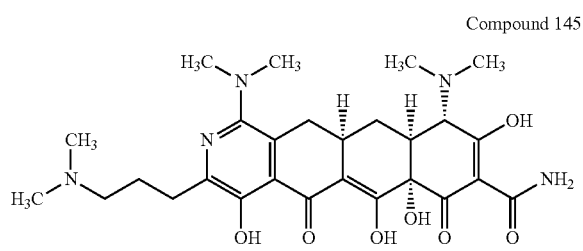 [SMILES: CN(C)CCCc1nc(N(C)C)c2c(c1O)C(=O)C1=C(O)[C@]3(O)C(=O)C(C(N)=O)=C(O)[C@@H](N(C)C)[C@@H]3C[C@@H]1C2]

Compound 145

Aqueous HF (0.4 mL, 48%) was added to a solution of S15-2 (14.0 mg, 0.0168 mmol) in 1,4-dioxane (0.6 mL) in a plastic vial. After 18 h, the reaction mixture was poured into a solution of K₂HPO₄ (4.8 g) in water (15 mL). The mixture was extracted with EtOAc (3×), and the combined extracts were dried over Na₂SO₄, filtered and concentrated under reduced pressure. The material was dissolved in methanol (1 mL), 0.5 M HCl in methanol (0.2 mL), and 1,4-dioxane (1 mL), and palladium on carbon (Degussa, 10 wt %, ~5 mg) was added. An atmosphere of hydrogen was introduced, and the reaction mixture was stirred for 3 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: CH₃CN; gradient: 0→70% B; mass-directed fraction collection]. Fractions with the desired MW were collected and freeze-dried to yield 5.5 mg (50%) of Compound 145 as a yellow solid. $^1$H NMR (400 MHz, CD$_3$OD with 1 drop DCl) δ 4.20 (s, 1H), 3.70-3.58 (m, 1H), 3.38-3.20 (m, 7H), 3.14-2.88 (m, 17H), 2.66-2.53 (m, 1H), 2.42-2.34 (m, 1H), 2.33-2.24 (m, 2H), 1.75-1.63 (m, 1H); MS (ESI) m/z 544.40 (M+H).

Example 17

Preparation of Compounds of Formula I, wherein Y is Hydrogen and Z is Hydrogen

Compounds of Formula I, wherein Y is hydrogen and Z is hydrogen (as well as compounds of Formula III, wherein Y is hydrogen) were prepared according to Scheme 16.

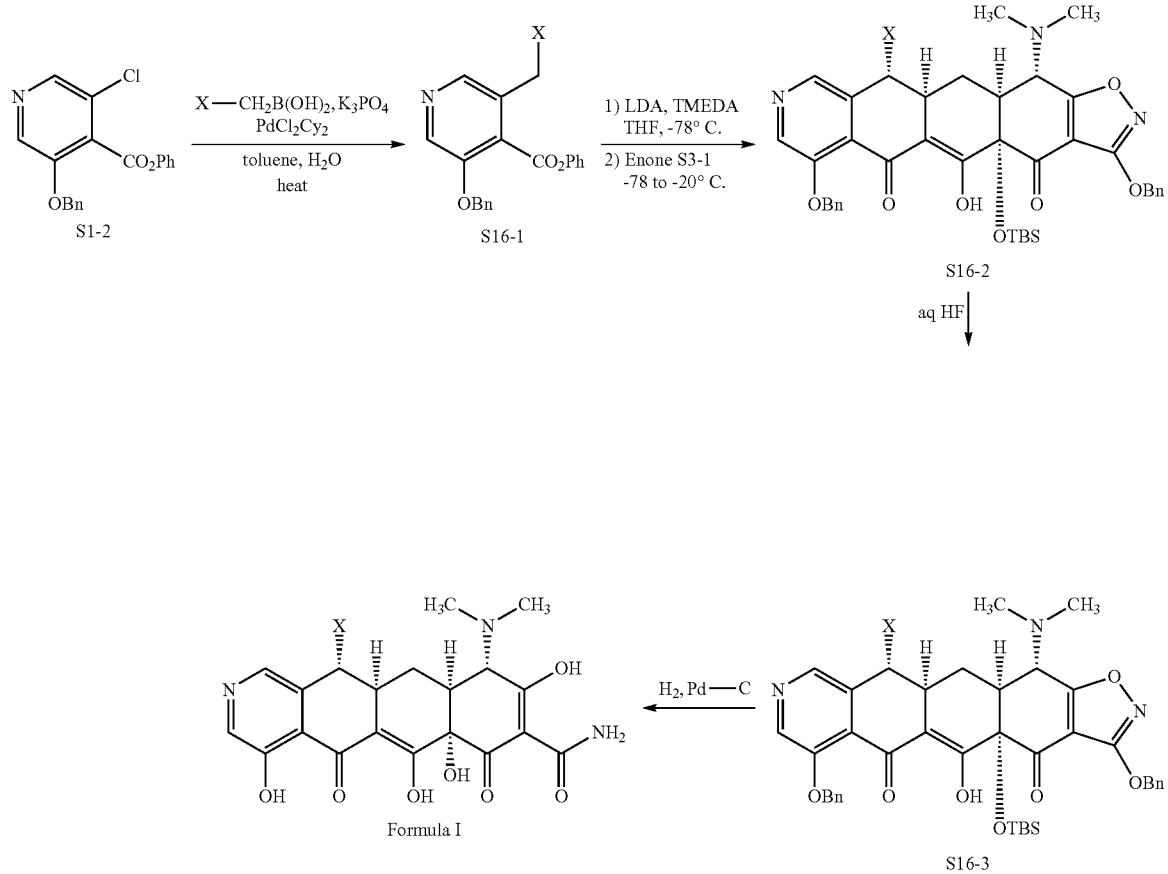

Synthesis of S16-1-1

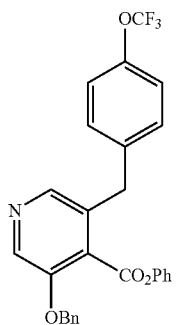

Intermediate S1-2 (326 mg, 0.959 mmol), 4-(trifluoromethoxy)-benzyl boronic acid (579 mg, 1.92 mmol), dichlorobis(tricyclohexylphosphine)-palladium(II) (16 mg, 0.048 mmol), and $K_3PO_4$ (814 mg, 17.7 mmol) were heated to 100° C. in toluene (4 mL) and water (1 mL). After 4 h, additional 4-(trifluoromethoxy)-benzylboronic acid (579 mg, 1.92 mmol) and dichlorobis(tricyclohexylphosphine)-palladium(II) (16 mg, 0.0048 mmol) were added. After another 4 h, additional 4-(trifluoromethoxy)benzylboronic acid (579 mg, 1.92 mmol) and dichlorobis-(tricyclohexylphosphine) palladium(II) (16 mg, 0.0048 mmol) were added. After heating overnight, the reaction mixture was allowed to cool to rt and was diluted with EtOAc (20 mL) This was washed with water (20 mL) and $NaHCO_3$ (saturated, aqueous solution, 20 mL), dried over $Na_2SO_4$, filtered, and concentrated under reduced pressure. The material was purified by column chromatography (Biotage 20 g column, 0 to 35% EtOAc/hexanes gradient), yielding 17.9 mg (4%) of the product as a white solid. $R_f$=0.21 in 30% EtOAc/hexanes. $^1$H NMR (400 MHz, $CDCl_3$) δ 8.42 (s, 1H), 8.26 (s, 1H), 7.45-7.15 (m, 12H), 6.78-6.71 (m, 2H), 5.26 (s, 2H), 4.14 (s, 2H).

Synthesis of S16-2-1

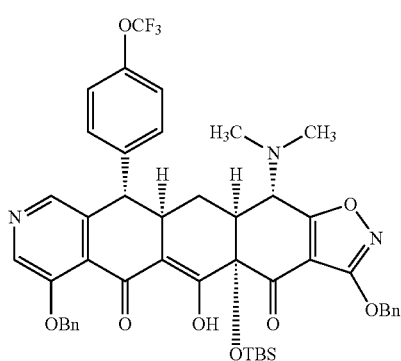

A solution of intermediate S16-1-1 (43.8 mg, 0.0907 mmol) in THF (0.5 mL) was added drop wise to a −78° C. solution of lithium diisopropylamide (1.8 M solution in hexanes, 0.050 mL, 0.091 mmol) and TMEDA (0.014 mL, 0.091 mmol) in THF (2 mL). After 5 min, a solution of S3-1 (14.6 mg, 0.0302 mmol) in THF (0.5 mL) was added drop wise. After complete addition, the reaction mixture was allowed to warm to −20° C. LC/MS indicated a lot of S16-1-1 and S3-1 remained. The reaction mixture was again cooled to −78° C., and additional lithium diisopropylamide (1.8 M solution in hexanes, 0.050 mL, 0.091 mmol) was added. The reaction mixture was allowed to warm to −10° C. and was quenched by the addition of ammonium chloride (saturated, aqueous solution), was diluted with water, and was extracted with EtOAc (2×20 mL). The combined extracts were dried over $Na_2SO_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 80→100% B; mass-directed fraction collection], yielding 3.9 mg (15%) of the desired product as a yellow solid. $^1$H NMR (400 MHz, $CDCl_3$) δ 16.10 (s, 1H), 8.38 (s, 1H), 7.58-7.24 (m, 15H), 5.40-5.30 (m, 5H), 3.96 (d, J=11.0 Hz, 1H), 3.90-3.83 (m, 1H), 3.42-3.36 (m, 1H), 2.55-2.48 (m, 7H), 2.00-1.92 (m, 1H), 0.84 (s, 9H), 0.25 (s, 3H), 0.18 (s, 3H); MS (ESI) m/z 868.58 (M+H).

Compound 111

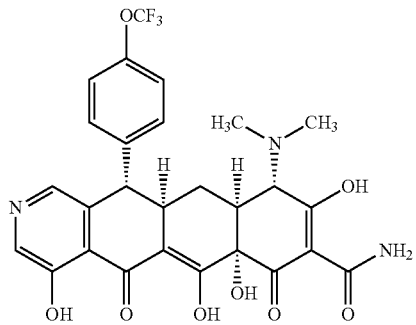

Aqueous HF (0.4 mL, 48%) was added to a solution of S16-2-1 (3.9 mg, 0.0045 mmol) in $CH_3CN$ (0.4 mL) in a plastic vial. After 18 h, the reaction mixture was poured into a solution of $K_2HPO_4$ (4.8 g) in water (20 mL). The mixture was extracted with EtOAc (2×20 mL). The combined EtOAc extracts were dried over $Na_2SO_4$, filtered and concentrated under reduced pressure. The material was dissolved in methanol (1 mL) and 1,4-dioxane (1 mL), and palladium on carbon (Degussa, 10 wt %, ~2 mg) was added. An atmosphere of hydrogen was introduced, and the reaction mixture was stirred for 1 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 10→100% B; mass-directed fraction collection]. Fractions with the desired MW were collected and freeze-dried to yield 1.7 mg (59%, 2 steps) of the desired product as a yellow solid. $^1$H NMR (400 MHz, $D_2O$) δ 8.29 (s, 1H), 7.40-7.20 (m, 5H), 3.95 (s, 1H), 3.70-3.00 (br m, 3H), 2.95-2.60 (m, 7H), 1.45-1.25 (m, 1H); MS (ESI) m/z 576.35 (M+H).

Synthesis of S16-1-2

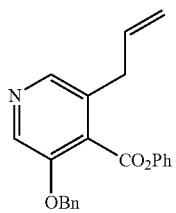

S16-1-2

Intermediate S1-2 (104 mg, 0.306 mmol), allylboronic acid pinacol ester (154 mg, 0.918 mmol), dichlorobis(tricyclohexylphosphine)palladium(II) (5 mg, 0.015 mmol), and $K_3PO_4$ (195 mg, 0.918 mmol) were heated to 200° C. in toluene (1 mL) and water (0.1 mL) via microwave for 5 min. The reaction mixture was diluted with EtOAc (10 mL). This was washed with water (5 mL) and brine (5 mL), dried over $Na_2SO_4$, filtered, and concentrated under reduced pressure. The material was purified by column chromatography (Biotage 10 g column, 0 to 30% EtOAc/hexanes gradient), yielding 74.6 mg (71%) of the product as a thick oil. $R_f$=0.43 in 50% EtOAc/hexanes. $^1$H NMR (400 MHz, DMSO-d6) δ 8.55 (s, 1H), 8.26 (s, 1H), 7.50-7.29 (m, 8H), 7.15-7.05 (m, 2H), 6.00-5.89 (m, 1H), 5.36 (s, 2H), 5.12-5.05 (m, 2H), 3.48 (d, J=6.44 Hz, 2H); MS (ESI) m/z 346.28 (M+H).

Synthesis of S16-2-2

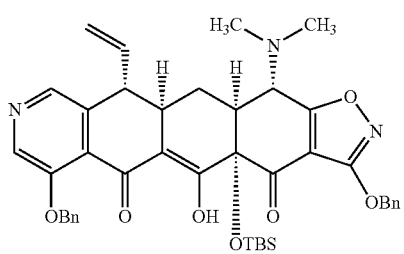

S16-2-2

A solution of intermediate S16-1-2 (72 mg, 0.21 mmol) in THF (0.5 mL) was added drop wise to a −78° C. solution of lithium diisopropylamide (1.8 M solution in hexanes, 0.23 mL, 0.42 mmol) and TMEDA (0.125 mL, 0.832 mmol) in THF (3 mL). After 5 min, a solution of S3-1 (50 mg, 0.10 mmol) in THF (0.5 mL) was added drop wise. After complete addition, the reaction mixture was allowed to warm to 0° C. over ~45 min. The reaction mixture was quenched by the addition of ammonium chloride (saturated, aqueous solution) and was extracted with EtOAc (3×). The combined extracts were dried over $Na_2SO_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 80→100% B; mass-directed fraction collection], yielding 18.7 mg (26%) of the desired product as a yellow solid. $^1$H NMR (400 MHz, CDCl$_3$) δ 16.09 (s, 1H), 8.42 (s, 1H), 8.24 (s, 1H), 7.52-7.24 (m, 10H), 5.80-5.70 (m, 1H), 5.62-5.56 (m, 1H), 5.41-5.26 (m, 5H), 3.89 (d, J=10.4 Hz, 1H), 3.26 (dd, J=14.0 Hz, J=9.76 Hz, 1H), 2.85 (t, J=11.3 Hz, 1H), 2.60-2.38 (m, 8H), 2.24-2.14 (m, 1H), 0.81 (s, 9H), 0.25 (s, 3H), 0.13 (s, 3H); MS (ESI) m/z 734.70 (M+H).

Compound 113

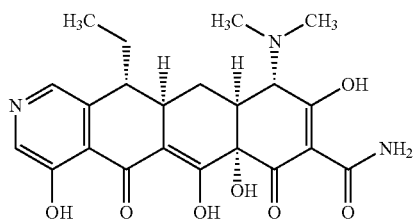

Compound 113

Aqueous HF (0.4 mL, 48%) was added to a solution of S16-2-2 (18.7 mg, 0.025 mmol) in $CH_3CN$ (0.6 mL) in a plastic vial. After 18 h, the reaction mixture was poured into a solution of $K_2HPO_4$ (4.8 g) in water (20 mL). The mixture was extracted with EtOAc (3×20 mL). The combined EtOAc extracts were dried over $Na_2SO_4$, filtered and concentrated under reduced pressure. The material was dissolved in methanol (2 mL) and 1,4-dioxane (2 mL), and HCl (conc., 2 drops) and palladium on carbon (Degussa, 10 wt %, 10 mg) was added. An atmosphere of hydrogen was introduced, and the reaction mixture was stirred for 2 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05 N HCl in water; Solvent B: $CH_3CN$; gradient: 0→50% B; mass-directed fraction collection]. Fractions with the desired MW were collected and freeze-dried to yield 6.9 mg (52%, 2 steps) of the desired product as a yellow solid. $^1$H NMR (400 MHz, CD$_3$OD with 1 drop DCl) δ 8.56 (s, 1H), 8.36 (s, 1H), 4.22 (s, 1H), 3.90-3.78 (m, 1H), 3.30-2.88 (m, 8H), 2.46-2.32 (m, 1H), 2.30-2.16 (m, 1H), 2.12-1.95 (m, 1H), 1.68-1.52 (m, 1H), 0.96 (br s, 3H); MS (ESI) m/z 444.46 (M+H).

Example 18

Preparation of Compounds of Formula I, wherein X is Hydrogen and Z is —N—C(O)—(C$_1$-C$_6$ alkyl)

Compounds of Formula I, wherein X is hydrogen and Z is —N—C(O)—(C$_1$-C$_6$ alkyl) (as well as compounds of Formula II, wherein Z is —N—C(O)—(C$_1$-C$_6$ alkyl)) were prepared according to Scheme 17.

Scheme 17

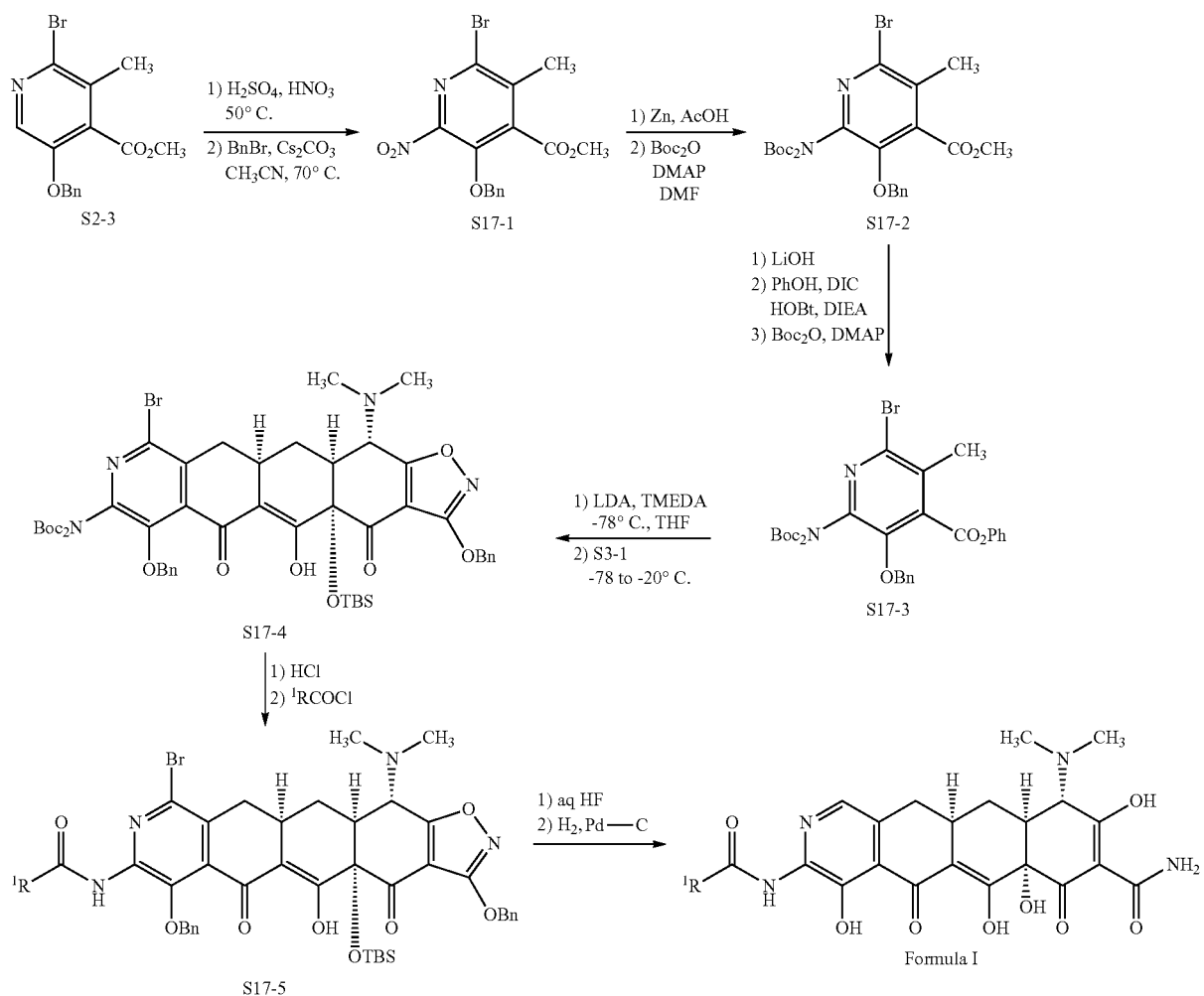

Specific intermediates and compounds of the invention prepared by Scheme 17 are described in detail below.

Synthesis of S17-1

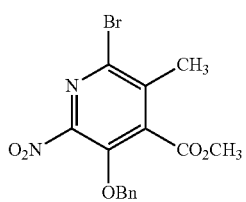

S17-1

Intermediate S2-3 (2.09 g, 6.22 mmol) was added to $H_2SO_4$ (conc., 25 mL) at 50° C. After 30 min, $HNO_3$ (conc., 1.18 mL) was added in 0.2 mL portions every 2 min. Starting material still remained by LC/MS, so an additional portion of $HNO_3$ (conc., 0.50 mL) was added. The reaction mixture was cooled to rt and was poured onto ice (100 mL). The reaction flask was rinsed with water (50 mL) and this was added to the ice mixture. This was extracted with EtOAc (3×100 mL), and the combined extracts were dried over $Na_2SO_4$, filtered, and concentrated under reduced pressure. The crude material, benzyl bromide (1.0 mL, 8.4 mmol) and $Cs_2CO_3$ were heated to 70° C. in acetonitrile (40 mL). After 2 h, the reaction mixture was cooled to room temperature and was diluted with water (50 mL). This was extracted with EtOAc (3×50 mL), and the combined extracts were dried over $Na_2SO_4$, filtered, and concentrated under reduced pressure. The material was purified by column chromatography (Biotage 20 g column, 0 to 10% EtOAc in hexanes gradient), yielding 972 mg (41%) of the product as a yellow solid. $R_f$=0.45 in 50% EtOAc/ hexanes. ¹H NMR (400 MHz, CDCl₃) δ 7.46-7.24 (m, 5H), 5.09 (s, 2H), 3.86 (s, 3H), 2.40 (s, 3H); MS (ESI) m/z 381.28 (M+H).

Synthesis of S17-2

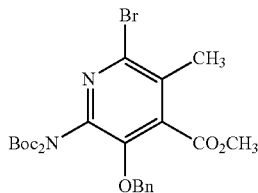

S17-2

Zinc powder (870 mg, 13.3 mmol) was added in ~200 mg portions to a solution of intermediate S17-1 (507 mg, 1.33 mmol) in acetic acid (4 mL) and THF (16 mL) over ~10 min. After 1 h, the material was filtered through Celite, and the filtrate was concentrated under reduced pressure. The material was dissolved in EtOAc (50 mL) and was washed NaHCO₃ (saturated, aqueous solution, 2×50 mL). The organics were dried over Na₂SO₄, filtered, and concentrated under reduced pressure. The crude material, di-t-butyldicarbonate (762 mg, 3.49 mmol) and 4-dimethylaminopyridine (14 mg, 0.12 mmol) were heated to 70° C. in N,N-dimethylformamide (5 mL). After heating overnight, an additional portion of di-t-butyldicarbonate (300 mg, 1.37 mmol) was added. After 30 min, the reaction mixture was cooled to room temperature, was diluted with EtOAc (20 mL), and was washed with water (3×20 mL) and brine (20 mL). The organics were dried over Na₂SO₄, filtered, and concentrated under reduced pressure. The material was purified by column chromatography (Biotage 10 g column, 0 to 14% EtOAc in hexanes gradient), yielding 464 mg (78%) of the product as a white, waxy solid. R$_f$=0.37 in 20% EtOAc/hexanes. ¹H NMR (400 MHz, DMSO-d6) δ 7.46-7.29 (m, 5H), 4.85 (s, 2H), 3.89 (s, 3H), 2.29 (s, 3H), 1.34 (s, 18H); MS (ESI) m/z 551.42, 553.42 (M+H).

Synthesis of S17-3

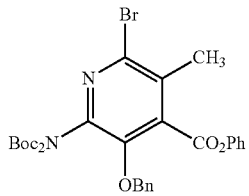

S17-3

Lithium hydroxide monohydrate (300 mg, 7.16 mmol) was added in to a solution of S17-2 (395 mg, 0.716 mmol) in methanol (5 mL), THF (5 mL) and water (50 mL). The reaction mixture was heated to 50° C. After heating overnight, the reaction mixture was brought to pH ~2 with 1 N HCl and was extracted with EtOAc (3×20 mL). The combined extracts were dried over Na₂SO₄, filtered, and concentrated under reduced pressure. The crude material, phenol (126 mg, 1.33 mmol), 1-hydroxybenzotriazole hydrate (153 mg, 0.998 mmol), diisopropylcarbodiimide (0.156 mL, 0.998 mmol) and diisopropylethylamine (0.347 mL, 2.00 mmol) were stirred for 2 h in N,N-dimethylformamide (1 mL) and methylene chloride (5 mL). An additional portion of phenol (126 mg, 1.33 mmol) was added, and the reaction mixture was heated to 40° C. After 3 h, the reaction mixture was cooled to room temperature, and the methylene chloride was removed under reduced pressure. Di-t-butyldicarbonate (725 mg, 3.33 mmol) and 4-dimethylaminopyridine (8 mg, 0.07 mmol) were added, and the reaction mixture was heated to 70° C. After 30 min, the reaction mixture was cooled to room temperature, was diluted with EtOAc (50 mL), and was washed with water (3×30 mL) and brine (30 mL). The organics were dried over Na₂SO₄, filtered, and concentrated under reduced pressure. The material was purified by column chromatography (Biotage 20 g column, 0 to 10% EtOAc in hexanes gradient), yielding 319 mg (78%) of the product as a thick, colorless oil. R$_f$=0.37 in 15% EtOAc/hexanes. ¹H NMR (400 MHz, CDCl₃) δ 7.39-7.30 (m, 8H), 6.98 (d, J=7.3 Hz, 2H), 5.00 (s, 2H), 2.49 (s, 3H), 1.40 (s, 18H); MS (ESI) m/z 613.49, 615.49 (M+H).

Synthesis of S17-4

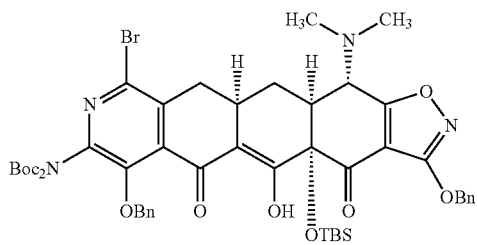

S17-4

Lithium diisopropylamide (10 wt % suspension in hexanes, 0.60 mL, 0.40 mmol) was added in ~0.020 mL portions to a −78° C. solution of intermediate S17-3 (76.2 mg, 0.124 mmol), TMEDA (0.070 mL, 0.58 mmol) and S3-1 (35 mg, 0.072 mmol) in THF (2 mL). At this point, a reddish colored solution persisted, and the reaction mixture was allowed to warm to 0° C. The reaction mixture was quenched by the addition of ammonium chloride (saturated, aqueous solution) and was extracted with EtOAc (2×). The combined extracts were dried over Na₂SO₄, filtered, and concentrated under reduced pressure. The material was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 80→100% B; mass-directed fraction collection], yielding 40 mg (55%) of the desired product as a yellow solid. ¹H NMR (400 MHz, CDCl₃) δ 15.46 (s, 1H), 7.56-7.24 (m, 10H), 5.36 (s, 2H), 4.93 (dd, J=36.0 Hz, J=9.8 Hz, 2H), 3.90 (d, J=11.0 Hz, 1H), 3.28 (dd, J=16.5 Hz, J=5.48 Hz, 1H), 3.14-3.05 (m, 1H), 2.65-2.42 (m, 9H), 2.17 (d, J=14.6 Hz, 1H), 1.40 (s, 18H), 0.81 (s, 9H), 0.26 (s, 3H), 0.12 (s, 3H); MS (ESI) m/z 1001.86, 1003.86 (M+H).

Synthesis of S17-5-1

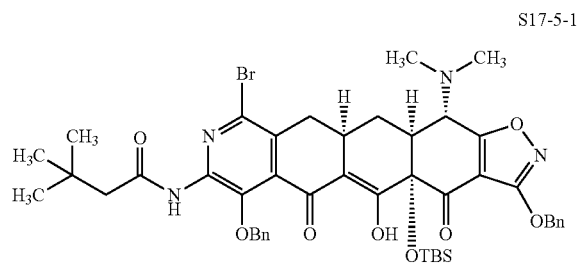 [SMILES: CN(C)[C@@H]1c2onc(OCc3ccccc3)c2C(=O)[C@@]2(O[Si](C)(C)C(C)(C)C)C(O)=C3C(=O)c4c(c(Br)nc(NC(=O)CC(C)(C)C)c4OCc4ccccc4)C[C@H]3C[C@@H]12]

S17-5-1

Intermediate S17-4 (84.1 mg, 0.0.0839 mmol) was stirred in 4 M HCl in 1,4-dioxane (2 mL) and 1,4-dioxane (2 mL) overnight. The reaction mixture was concentrated under reduced pressure. Approximately ⅓ of the material was dissolved in pyridine (0.25 mL), and t-butylacetylchloride (0.0039 mL, 0.028 mmol) was added. After 2 h, additional t-butylacetylchloride (2 drops) was added, and the reaction mixture was heated to 40° C. After 30 min, complete diacylation was observed by LC/MS. $Na_2CO_3$ (1 M aqueous solution, 1 mL), methanol (1 mL), and THF (1 mL) were added and heating was continued at 40° C. After heating overnight, the pH was adjusted to ~7 with 1 M aqueous HCl, and this was extracted with EtOAc (3×). The combined extracts were dried over $Na_2SO_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; gradient: 80→100% B; mass-directed fraction collection], yielding 7.6 mg (30%) of the desired product as a yellow solid. $^1H$ NMR (400 MHz, $CDCl_3$) δ 15.47 (s, 1H), 7.66 (s, 1H), 7.54-7.48 (m, 2H), 7.42-7.32 (m, 8H), 5.36 (s, 2H), 4.94 (dd, J=59.8 Hz, J=11.0 Hz, 2H), 3.88 (d, J=11.0 Hz, 1H), 3.23 (dd, J=16.5 Hz, J=4.88 Hz, 1H), 3.12-3.02 (m, 1H), 2.65-2.42 (m, 9H), 2.36-2.14 (m, 3H), 1.02 (s, 9H), 0.82 (s, 9H), 0.27 (s, 3H), 0.13 (s, 3H); MS (ESI) m/z 899.75, 901.74 (M+H).

Compound 127

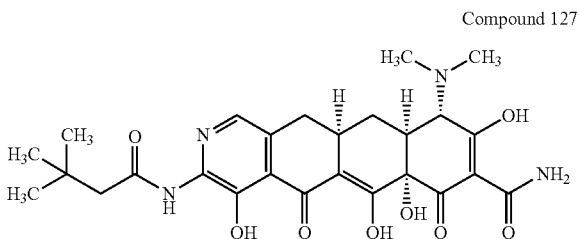 [SMILES: CN(C)[C@@H]1C(O)=C(C(N)=O)C(=O)[C@@]2(O)C(O)=C3C(=O)c4c(cnc(NC(=O)CC(C)(C)C)c4O)C[C@H]3C[C@@H]12]

Compound 127

Aqueous HF (0.4 mL, 48%) was added to a solution of S17-5-1 (7.6 mg, 0.0084 mmol) in $CH_3CN$ (0.6 mL) in a plastic vial. After 18 h, the reaction mixture was poured into a solution of $K_2HPO_4$ (4.8 g) in water (10 mL). The mixture was extracted with EtOAc (3×15 mL). The combined EtOAc extracts were dried over $Na_2SO_4$, filtered and concentrated under reduced pressure. The material was dissolved in metha-nol (1 mL) and 1,4-dioxane (1 mL), and palladium on carbon (Degussa, 10 wt %, ~15 mg) was added. An atmosphere of hydrogen was introduced, and the reaction mixture was stirred for 1 h. The reaction mixture was filtered through Celite, and the filtrate was concentrated under reduced pressure. The material was purified on a Waters Autopurification system equipped with a Phenomenex Polymerx 10μ RP 100A column [10 μm, 30×21.20 mm; flow rate, 20 mL/min; Solvent A: 0.05 N HCl in water; Solvent B: $CH_3CN$; gradient: 0→100% B; mass-directed fraction collection]. Fractions with the desired MW were collected and freeze-dried to yield 2.0 mg (42%, 2 steps) of the desired product as a yellow solid. $^1H$ NMR (400 MHz, $CD_3OD$ with 1 drop DCl) δ 7.82 (s, 1H), 4.18 (s, 1H), 3.40-2.95 (m, 9H), 2.65-2.54 (m, 3H), 2.36-2.28 (m, 1H), 1.70-1.59 (m, 1H), 1.12 (s, 9H); MS (ESI) m/z 529.54 (M+H).

Example 19

Antibacterial Assays

The antibacterial activities for the compounds of the invention were studied according to the following protocols.
Minimum Inhibitory Concentration Assay Frozen bacterial strains were thawed and subcultured onto Mueller Hinton Broth (MHB) or other appropriate media (*Streptococcus* requires blood and *Haemophilus* requires hemin and NAD). Following incubation overnight, the strains were subcultured onto Mueller Hinton Agar and again incubated overnight. Colonies were observed for appropriate colony morphology and lack of contamination. Isolated colonies were selected to prepare a starting inoculum equivalent to a 0.5 McFarland standard. The starting inoculum was diluted 1:125 using MHB for further use. Test compounds were prepared by dilution in sterile water to a final concentration of 5.128 mg/mL. Antibiotics (stored frozen, thawed and used within 3 hours of thawing) and compounds were further diluted to the desired working concentrations.

The assays were run as follows. Fifty μL of MHB was added to wells 2-12 of a 96-well plate. One hundred μL of appropriately diluted antibiotic or compound was added to well 1. Fifty μL of antibiotics or compound was removed from well 1 and added to well 2 and the contents of well 2 mixed by pipetting up and down five times. Fifty μL of the mixture in well 2 was removed and added to well 3 and mixed as above. Serial dilutions were continued in the same manner through well 12. Fifty μL was removed from well 12 so that all contained 50 μL. Fifty μL of the working inoculum was then added to all test wells. A growth control well was prepared by adding 50 μL of working inoculum and 50 μL of MHB to an empty well. The plates were then incubated at 37° C. overnight, removed from the incubator and each well was read on a plate reading mirror. The lowest concentration (MIC) of test compound that inhibited the growth of the bacteria was recorded.

Example

| | 1 | 2 | 3 | 4 | 5 | 6 | 7 | 8 | 9 | 10 | 11 | 12 |
|---|---|---|---|---|---|---|---|---|---|---|---|---|
| [Abt] | 32 | 16 | 8 | 4 | 2 | 1 | 0.5 | 0.25 | 0.125 | 0.06 | 0.03 | 0.015 |
| grow | − | − | − | − | − | + | + | + | + | + | + | + |

[abt] = antibiotic concentration in the well
Grow = bacterial growth (cloudiness)

Interpretation: MIC=2 μg/mL

Protocol for Determining Inoculum Concentration (Viable Count)

Ninety μl of sterile 0.9% NaCl was pipetted into wells 2-6 of a 96-well microtiter plate. Fifty 50 μl of the inoculum was pipetted into well 1. Ten μL from was removed from well 1 and added it to well 2 followed by mixing. Ten μL was removed from well two and mixed with the contents of well 3 and so on creating serial dilutions through well 6. Ten μL was removed from each well and spotted onto an appropriate agar plate. The plate was placed into a $CO_2$ incubator overnight.

The colonies in spots that contain distinct colonies were counted. Viable count was calculated by multiplying the number of colonies by the dilution factor.

| Spot from Well | 1 | 2 | 3 | 4 | 5 | 6 |
|---|---|---|---|---|---|---|
| Dilution Factor | $10^2$ | $10^3$ | $10^4$ | $10^5$ | $10^6$ | $10^7$ |

Bacterial Strains

Fifteen bacterial strains, listed below, were examined in minimum inhibitory concentration (MIC) assays.

| ORGANISM | STRAIN DESIGNATION | KEY PROPERTIES |
|---|---|---|
| *Staphylococcus aureus* | SA100 | ATCC 13709, MSSA, Smith strain |
| *Staphylococcus aureus* | SA101 | ATCC 29213, CLSI quality control strain, MSSA |
| *Staphylococcus aureus* | SA191 | HA-MRSA, tetracycline-resistant, lung infection model isolate |
| *Staphylococcus aureus* | SA161 | HA-MRSA, tetracycline-resistant, tet(M) |
| *Staphylococcus aureus aaaureusaureus* | SA158 | Tetracycline-resistant tet(K) |
| *Staphylococcus epidermidis* | SE164 | ATCC 12228, CLSI quality control strain, tetracycline-resistant |
| *Enterococcus faecalis* | EF103 | ATCC 29212, tet-I/R, control strain |
| *Enterococcus faecalis* | EF159 | Tetracycline-resistant, tet(M) |
| *Enterococcus faecalis* | EF327 | Wound isolate (US) tet(M) |
| *Enterococcus faecium* | EF404 | Blood isolate (US) tet(M) |
| *Streptococcus pneumoniae* | SP106 | ATCC 49619, CLSI quality control strain |
| *Streptococcus pneumoniae* | SP160 | Tetracycline-resistant, tet(M) |
| *Streptococcus pyogenes* | SP312 | 2009 clinical isolate, tet(M) |
| *Streptococcus pyogenes* | SP193 | *S. pyogenes* for efficacy models; tetS; sensitive to sulfonamides |
| *Haemophilus influenzae* | HI262 | Tetracycline-resistant, ampicillin-resistant |
| *Moraxella catarrhalis* | MC205 | ATCC 8176, CLSI quality control strain |
| *Escherichia coli* | EC107 | ATCC 25922, CLSI quality control strain |
| *Escherichia coli* | EC155 | Tetracycline-resistant, tet(A) |
| *Escherichia coli* | EC878 | MG1655 tolC::kan |
| *Escherichia coli* | EC880 | lpxA |
| *Escherichia coli* | EC882 | impA |
| *Escherichia coli* | EC200 | MDR uropathogenic; serotype O17:K52:H18; UMN 026; trimeth/sulfa-R; BAA-1161 |
| *Enterobacter cloacae* | EC108 | ATCC 13047, wt |
| *Enterobacter cloacae* | EC603 | Urine isolate (Spain) |
| *Klebsiella pneumoniae* | KP109 | ATCC 13883, wt |
| *Klebsiella pneumoniae* | KP153 | Tetracycline-resistant, tet(A), MDR, ESBL[+] |
| *Klebsiella pneumoniae* | KP457 | 2009 ESBL[+], CTX-M, OXA |
| *Proteus mirabilis* | PM112 | ATCC 35659 |
| *Proteus mirabilis* | PM385 | Urine ESBL[+] isolate |
| *Pseudomonas aeruginosa* | PA111 | ATCC 27853, wt, control strain |
| *Pseudomonas aeruginosa* | PA169 | Wt, parent of PA170-173 |
| *Pseudomonas aeruginosa* | PA173 | PA170 ΔmexX; MexXY-(missing a functional efflux pump) |
| *Pseudomonas aeruginosa* | PA555 | ATCC BAA-47, wild type strain PAO1 |
| *Pseudomonas aeruginosa* | PA556 | Multiple-Mex efflux pump knockout strain |
| *Pseudomonas aeruginosa* | PA689 | Blood isolate (US) |
| *Acinetobacter baumannii* | AB110 | ATCC 19606, wt |
| *Acinetobacter baumannii* | AB250 | Cystic fibrosis isolate, MDR |
| *Stenotrophomonas maltophilia* | SM256 | Cystic fibrosis isolate, MDR |
| *Burkholderia cenocepacia* | BC240 | Cystic fibrosis isolate, MDR |

*MDR, multidrug-resistant; MRSA, methicillin-resistant *S. aureus*; MSSA, methicillin-sensitive *S. aureus*; HA-MRSA, hospital-associated MRSA; tet(K), major gram-positive tetracycline efflux mechanism; tet(M), major gram-positive tetracycline ribosome-protection mechanism; ESBL[+], extended spectrum β-lactamase Results Values of minimum inhibition concentration (MIC) for the compounds of the invention are provided in Table 2.

TABLE 2

MIC Values for Compounds of the Invention Compared to Sancycline, Minocycline and Tigecycline.

| Cmpd | SA101 29213 | SA100 13709 | SA161 MRSA, tetM | SA158 tetK | EF103 29212 | EF159 tetM | SP106 49619 | SP160 tetM |
|---|---|---|---|---|---|---|---|---|
| 100 | C | C | C | C | B | C | C | B |
| 101 | A | A | B | B | B | B | A | B |
| 102 | B | B | C | C | C | C | B | C |
| 103 | C | C | B | C | B | B | C | B |
| 104 | C | B | B | B | B | B | C | B |
| 105 | C | C | C | C | C | C | C | C |
| 106 | C | C | C | C | C | B | C | B |
| 107 | C | C | B | B | B | B | C | C |
| 108 | B | B | B | B | B | B | B | B |
| 109 | A | B | C | B | B | C | B | B |
| 110 | A | A | B | B | B | B | B | B |
| 111 | C | C | NT | B | B | B | C | B |
| 112 | B | B | B | B | B | B | C | B |
| 113 | B | B | C | C | C | C | NT | C |
| 114 | B | B | B | B | B | B | C | B |
| 115 | C | B | B | B | B | B | C | B |
| 116 | C | C | C | C | C | C | C | C |
| 117 | C | C | C | C | C | C | C | C |
| 118 | C | C | C | C | C | C | C | C |
| 119 | C | C | B | B | B | C | C | B |
| 120 | C | C | C | C | B | C | C | B |
| 121 | B | B | B | B | B | C | B | C |
| 122 | C | C | C | C | C | C | C | C |
| 123 | C | B | C | C | C | C | C | C |
| 124 | A | A | B | B | B | B | B | B |
| 125 | B | B | B | C | B | B | B | B |
| 126 | B | B | B | B | B | B | C | C |
| 127 | C | C | C | C | C | C | C | C |
| 128 | C | C | C | C | C | C | C | C |
| 129 | B | B | B | B | B | B | B | B |
| 130 | C | C | C | B | B | B | C | B |
| 131 | C | C | B | B | B | B | C | C |
| 132 | C | C | C | C | B | C | C | C |
| 133 | C | B | B | B | B | B | C | B |
| 134 | C | C | C | C | C | C | C | C |
| 135 | C | C | C | B | B | B | C | B |
| 136 | C | B | B | B | B | B | C | B |
| 137 | C | C | C | C | C | C | C | C |
| 138 | C | C | C | C | C | C | C | C |
| 139 | C | B | B | B | B | B | C | C |
| 140 | C | C | B | B | B | B | C | B |
| 141 | B | B | B | B | B | B | C | B |
| 142 | C | C | C | C | B | B | C | B |
| 143 | B | B | C | C | B | C | B | B |
| 144 | A | B | B | C | B | C | A | B |
| 145 | C | C | C | C | C | C | C | B |
| 146 | C | B | C | C | B | C | C | C |
| 147 | B | A | B | C | B | C | A | B |
| 148 | C | B | B | B | B | B | C | C |
| 149 | C | C | C | C | B | B | C | B |
| 150 | A | A | B | B | B | B | B | B |
| 151 | B | B | B | B | B | B | A | B |
| 152 | B | B | C | B | C | C | B | C |
| 153 | B | B | B | B | B | B | B | B |
| 154 | B | B | B | B | B | B | C | C |
| 155 | C | C | C | C | C | C | C | C |
| 156 | A | B | B | B | B | B | B | B |
| 157 | C | B | B | B | B | B | C | C |
| 158 | C | C | C | C | C | C | C | C |
| 159 | C | C | C | C | C | C | C | C |
| 160 | B | B | C | B | B | C | B | B |
| 161 | C | C | C | C | C | C | C | C |
| 162 | B | B | B | B | B | B | C | B |
| 163 | C | C | C | C | B | B | C | B |
| 164 | C | C | C | C | C | C | C | C |
| 165 | C | C | B | C | B | B | C | B |
| San. | 0.5 | 1 | NT | 4 | 8 | 8 | 0.25 | 8 |
| Mino. | 0.06 | 0.06 | 8 | 0.03 | 1 | 16 | <0.015 | 2 |

TABLE 2-continued

MIC Values for Compounds of the Invention Compared to Sancycline, Minocycline and Tigecycline.

| Tige. | 0.06 | 0.06 | 0.125 | 0.06 | 0.03 | 0.06 | 0.0156 | 0.0156 |
|---|---|---|---|---|---|---|---|---|
| Cmpd | EC107 25922 | EC155 tetA | AB110 19606 | PA111 27853 | EC108 13047 | KP109 13883 | KP153 tetA | |
| 100 | C | C | C | C | C | C | C |
| 101 | B | B | A | A | B | B | B |
| 102 | B | C | C | A | B | B | C |
| 103 | B | C | C | C | C | B | C |
| 104 | C | B | C | C | C | C | C |
| 105 | C | C | C | C | C | C | C |
| 106 | C | C | C | C | C | C | C |
| 107 | C | C | C | C | C | C | C |
| 108 | B | B | C | C | B | B | B |
| 109 | B | C | C | A | B | B | C |
| 110 | B | B | A | B | B | B | B |
| 111 | C | C | C | C | C | C | C |
| 112 | C | C | C | C | C | C | C |
| 113 | B | C | B | C | B | B | C |
| 114 | B | B | B | B | B | B | B |
| 115 | C | C | C | C | C | C | C |
| 116 | C | C | C | C | C | C | C |
| 117 | C | C | C | C | C | C | C |
| 118 | C | C | C | C | C | C | C |
| 119 | B | C | C | C | C | C | C |
| 120 | B | C | C | C | C | C | C |
| 121 | B | C | C | C | B | B | C |
| 122 | C | C | C | C | C | C | C |
| 123 | B | C | C | C | B | B | C |
| 124 | B | B | A | B | B | B | B |
| 125 | B | C | C | A | B | B | C |
| 126 | C | C | C | C | C | C | C |
| 127 | C | C | C | C | C | C | C |
| 128 | C | C | C | C | C | C | C |
| 129 | B | B | C | C | B | B | B |
| 130 | B | B | C | C | B | B | B |
| 131 | C | C | C | C | C | C | C |
| 132 | B | C | C | C | B | B | C |
| 133 | B | B | C | C | B | B | B |
| 134 | C | C | C | C | C | C | C |
| 135 | B | B | C | C | C | C | B |
| 136 | C | C | C | C | C | C | C |
| 137 | C | C | C | C | C | C | C |
| 138 | C | C | C | C | C | C | C |
| 139 | C | C | C | C | C | C | C |
| 140 | B | B | C | C | B | B | B |
| 141 | C | C | C | C | C | C | C |
| 142 | B | C | C | C | C | B | C |
| 143 | B | C | C | C | B | B | C |
| 144 | B | C | B | A | B | B | C |
| 145 | B | C | C | C | C | C | C |
| 146 | B | C | C | A | B | B | C |
| 147 | B | C | C | A | B | B | C |
| 148 | C | C | C | C | C | C | C |
| 149 | C | C | C | C | C | C | C |
| 150 | B | B | B | C | B | B | C |
| 151 | B | B | C | C | B | B | B |
| 152 | B | C | C | B | B | B | C |
| 153 | B | C | B | C | C | C | C |
| 154 | C | C | C | C | C | C | C |
| 155 | C | C | C | C | C | C | C |
| 156 | B | B | C | C | C | B | B |
| 157 | C | C | C | C | C | C | C |
| 158 | B | C | C | C | B | B | C |
| 159 | B | C | C | C | B | C | C |
| 160 | B | C | B | C | B | B | C |
| 161 | C | C | C | C | C | C | C |
| 162 | C | C | C | C | C | C | C |
| 163 | B | C | C | C | C | C | C |
| 164 | C | C | C | C | C | C | C |
| 165 | C | C | C | C | C | C | C |

TABLE 2-continued

MIC Values for Compounds of the Invention Compared to Sancycline, Minocycline and Tigecycline.

| San. | 8 | 32 | 0.25 | >32 | 8 | 8 | 32 |
|---|---|---|---|---|---|---|---|
| Mino. | 0.5 | 8 | 0.06 | 16 | 2 | 1 | 8 |
| Tige. | 0.03 | 0.5 | 0.25 | 8 | 0.25 | 0.125 | 1 |

A = lower than or equal to lowest MIC among three control compounds;
B = greater than lowest MIC among three control compounds, but lower than highest MIC among three control compounds;
C = greater than MIC of all three control compounds.

Example 20

In Vitro Studies of Selected Compounds 108, 124, 141, 133 and 151

Antibacterial Activities

The antibacterial activities of Compounds 108, 124, 141, 133, and 151 were evaluated against panels of *E. faecalis*, *S. pneumoniae*, and *S. aureus* clinical isolates in the antibacterial assay protocols described above.

$MIC_{50}$ and $MIC_{90}$ are the Minimum Inhibitory Concentrations required to inhibit the growth of 50% of organisms or 90% of a collection of organisms respectfully. Both values, as well as the MIC range (the lowest and highest MIC value observed for a collection of organisms), were determined for the isolates listed in Table 3.

Results to express either protein upon arabinose induction. Genes encoding tet(M) and tet(K) were cloned by PCR from tetracycline-resistant *S. pneumoniae* (SP160) and *S. aureus* (SA158), respectively, using primers enabling cloning into the NcoI and XhoI sites of arabinose-inducible expression vector, pBAD/Myc-His (Invitrogen, Carlsbad, Calif.). Constructs were transformed into *E. coli* DH10B for expression. Recombinant strains were pre-induced under optimized conditions with L-arabinose prior to use as inocula in CLSI standardized MIC assays. Optimal pre-induction of DH10B (pBAD-tetM), expressing tet(M), and DH10B(pBAD-tetK), expressing tet(K), was with 1% L-arabinose at 35° C. and 0.1% L-arabinose at room temperature, respectively. MIC assays were incubated overnight at 35° C.

TABLE 3

| | S. pneumoniae 19 isolates | | | MRSA 30 isolates | | | E. faecalis 24 isolates | | |
|---|---|---|---|---|---|---|---|---|---|
| Compound | $MIC_{50}$ | $MIC_{90}$ | Range | $MIC_{50}$ | $MIC_{90}$ | Range | $MIC_{50}$ | $MIC_{90}$ | Range |
| 124 | 1 | 4 | <=0.016-8 | 0.5 | 2 | 0.25-4 | 4 | 4 | 0.008-4 |
| 151 | 0.063 | 0.25 | <=0.016-0.25 | 1 | 2 | 0.5-8 | 0.5 | 2 | 0.031-4 |
| 133 | 0.13 | 0.25 | <=0.016-0.25 | 1 | 2 | 0.5-8 | 1 | 2 | 0.25-4 |
| 141 | 4 | 4 | 0.25-8 | 4 | 4 | 2-4 | 8 | 8 | 1-8 |
| 108 | 0.0312 | 0.125 | <=0.016-0.13 | 0.5 | 2 | 0.5-8 | 0.5 | 2 | 0.063-4 |
| tetracycline | 32 | >32 | 0.031->32 | 0.25 | >32 | 0.25->32 | >32 | >32 | 0.5->32 |
| tigecycline | <=0.016 | <=0.016 | ≤0.016 | 0.13 | 0.13 | 0.063-0.25 | 0.063 | 0.13 | <=0.016-0.13 |
| doxycycline | 4 | 16 | <=0.016-16 | 0.25 | 8 | 0.063-8 | 8 | 16 | 0.063-16 |

Activity of Compounds Against *E. coli* Recombinantly Expressing tet(M) or tet(K)

The first tetracycline antibiotics were discovered more than 50 years ago, and represented a significant advance in the treatment of many gram-positive and gram-negative bacterial infections. However, following their initial widespread use, a high incidence of tetracycline resistance among many bacteria led to tetracyclines being relegated to second- or third-line therapy. The two main acquired tetracycline-resistance mechanisms are ribosomal protection and active drug efflux. Ribosomal protection is mediated by one of 14 classes of proteins that remove tetracycline and related compounds from their binding site in the 30S ribosomal subunit and include proteins like Tet(M) and Tet(O) (see on the world wide web at faculty.washington.edu/marilynr for complete list). Tetracyclinje-specific efflux pumps can be arranged into 26 classes and include tet(K) and tet(L) found predominantly in gram-positive bacteria and tet(A) and tet(B) found primarily in gram-negative bacteria.

Construction of DH10B(pBAD-tetM) and DH10B(pBAD-tetK)

To determine if novel tetracyclies were equally active in the presence or absence of tetracycline-resistant mechanisms Tet (M) and Tet(K), recombinant *E. coli* strains were constructed Results As shown below unlike tetracycline and doxycycline, of the compounds tested, the activities of compound 151, compound 108 and compound 133 are minimally affected by expression of (tet)M and unaffected by expression of (tet)K. As expected, the activities of non-tetracycline antibiotics (levofloxacin, amikacin and ceftriaxone) were unaffected by tet-gene expression whereas the MICs of tetracycline and doxycycline in the presence of tet(K) expression were >8- and 4-fold higher respectively than when tet(K) was not expressed. Similarly, the MICs of tetracycline and doxycycline were impacted when the ribosomal protection protein Tet(M) was expressed. Thus, compounds 151, 108, and 133 are equally active as measured by whole cell activity in the presence of either type of major tetracycline-resistance mechanism.

TABLE 4

Potency of compounds in the presence of Tet (K) efflux

| Compound | Uninduced | TetK Induced | TetM Ratio |
|---|---|---|---|
| 124 | 8 | 16 | 2 |
| 151 | 1 | 1 | 1 |

TABLE 4-continued

Potency of compounds in the presence of Tet (K) efflux

| Compound | Uninduced | TetK Induced | TetM Ratio |
|---|---|---|---|
| 108 | 4 | 2 | 0.5 |
| 133 | 2 | 1 | 0.5 |
| 141 | >32 | 32 | na |
| Tetracycline | 4 | >32 | >8 |
| Doxycycline | 2 | 8 | 4 |
| Levofloxacine | 0.0156 | 0.0156 | 1 |
| Amikacin | 8 | 8 | 1 |
| Ceftriaxone | 0.125 | 0.25 | 2 |

TABLE 5

Potency of Compounds against TetM ribosome protection

| Compounds | Uninduced | TetM induced | Ratio |
|---|---|---|---|
| 124 | 4 | 16 | 4 |
| 151 | 0.5 | 1 | 2 |
| 108 | 2 | 2 | 1 |
| 133 | 0.5 | 2 | 4 |
| 141 | 32 | 32 | 1 |
| Tetracycline | 4 | >32 | >8 |
| Doxycycline | 4 | 32 | 8 |
| Levofloxacine | 0.0156 | 0.0156 | 1 |
| Amikacin | 4 | 4 | 1 |
| Ceftriaxone | 0.0625 | 0.125 | 2 |

In Vitro Transcription/Translation Assay

Compound stocks prepared and diluted in sterile deionized water were assayed for inhibition of coupled in vitro transcription/translation using an *E. coli* S30 extract system with a firefly luciferase readout from Promega (Cat #L1020, Madison, Wis.). Briefly, compounds were diluted into water and added to reaction mix aliquoted to back-walled 96-well microtiter plates (Cat #3650, Costar, Corning, N.Y.). An appropriate three-point titration was used for each compound, and reactions were run in duplicate. The final total reaction volume was 20 μl. Plates were incubated at 37° C. for one hour and then placed on ice for 5 minutes to arrest transcription/translation. Luciferase substrate (25 μl, Promega Cat #E1500) was added to each well and luminescence was detected on a BMG LabTech LUMIstar-OPTIMA instrument. Positive assay control values, from reactions without inhibitor, were averaged per plate to determine percent inhibition of luciferase production. Results were plotted using Microsoft Excel and fifty percent inhibition values (IC50) were determined.

Results

Representative compounds of this class, compounds 151, 108 and 133 were shown in Table 6 to have sub-μg/ml IC50 values (0.7, 0.62, 0.6 μg/ml, respectively) in an in vitro transcription/translation system, supporting an anti-translation mechanism of action.

TABLE 6

In vitro transcription/translation assay

| Compound | TnT IC50 |
|---|---|
| 124 | >4.5 |
| 151 | 0.89 |
| 108 | 0.6 |
| 133 | 0.56 |
| 141 | >4.5 |

TABLE 6-continued

In vitro transcription/translation assay

| Compound | TnT IC50 |
|---|---|
| Tetracycline | 1.7 |
| Doxycycline | 2.63 |
| TIG | 0.3 |
| Levofloxacine | |
| Amikacin | |
| Ceftriaxone | |

Representative compounds of this class, compounds 109, 125, 132, 120, 149, 119 and 151 were shown in Table 7 to have sub-μg/ml IC50 values in an in vitro transcription/translation system, supporting an anti-translation mechanism of action.

TABLE 7

Transcription/Translation (TnT) assay data.

| Compound | TnT IC$_{50}$ (μg/mL) |
|---|---|
| 109 | 0.76 |
| 147 | 1.1 |
| 125 | 0.93 |
| 132 | 0.78 |
| 120 | 0.36 |
| 149 | 0.71 |
| 119 | 0.58 |
| 151 | 0.70 |
| 104 | 5.3 |
| 114 | 2.8 |
| 141 | 3.4 |
| Tetracycline | 2.0 |
| Tigecycline | 0.47 |

Example 21

In Vitro Studies of Compounds 109, 123, 144, 151, 108 and 133

Antibacterial Activities

The antibacterial activities of Compounds 109, 123, 144, 151, 108, 133 were studied according to the antibacterial assay described above. The antibacterial activities of Compounds MIC values were determined according to CLSI methodology. Recent clinical isolates were obtained from Eurofins-Medinet. Antibiotics were obtained from standard commercial sources.

Results

Results showed that, unlike tetracycline whose activity was severely abrogated by these mechanisms, the antibacterial activity of Compounds 108, 151 and 133 compounds remained potent against tet(M) and tet(S) strains of *E. faecalis* (≤4 μg/ml)), tet(M) strains of *S. pneumoniae* (≤0.25 μg/ml), tet(M) strains of *S. aureus* (≤8 μg/ml), and tet(K) strains of *S. aureus* (≤1 μg/ml).

TABLE 8

Representative Compounds and Spectrum of Activity

| Compound | E. coli TnT µg/ml | S. aureus ATCC 29213 µg/ml | S. aureus MRSA, tetM µg/ml | S. aureus tetK µg/ml | E. faecalis ATCC 29212 µg/ml | E. faecalis tetM µg/ml | S. pneumoniae ATCC 49619 µg/ml | S. pneumoniae tetM µg/ml | E. coli ATCC 25922 µg/ml | E. coli tetA µg/ml |
|---|---|---|---|---|---|---|---|---|---|---|
| tetracycline | 1.7 | 0.25 | 64 | 16 | 8 | 64 | 0.063 | 16 | 1 | >64 |
| doxycycline | 2.6 | 0.13 | 8 | 2 | 4 | 4 | 0.06 | 4 | 1 | 32 |
| minocycline | 3.1 | 0.06 | 8 | 0.03 | 1 | 16 | ≤0.016 | 2 | 0.5 | 8 |
| 109 | 0.9 | 0.031 | 16 | 2 | 1 | 32 | 0.031 | 8 | 0.13 | >32 |
| 123 | n/a | 1 | 32 | 32 | 32 | >32 | 1 | 32 | 2 | >32 |
| 144 | n/a | 0.031 | 8 | 8 | 4 | 32 | 0.016 | 8 | 0.25 | >32 |
| 151 | 0.7 | 0.25 | 2 | 0.13 | 0.25 | 2 | 0.063 | 0.5 | 0.5 | 8 |
| 108 | 0.62 | 0.25 | 2 | 0.13 | 0.5 | 2 | 0.031 | 0.25 | 2 | 8 |
| 133 | 0.6 | 1 | 2 | 0.5 | 0.5 | 2 | 0.5 | 1 | 1 | 8 |

Example 22

In Vitro and In Vivo Activities of Compound 109 and 151

Antibacterial Activity

Compound 109 and Compound 151 were tested for antibacterial activity according to the protocols described above.

MIC, $MIC_{50}$ and $MIC_{90}$ values were determined according to CLSI methodology. S. pneumoniae and H. influenzae isolates were obtained from Eurofins-Medinet and are recent clinical isolates. S. aureus strains were collected from various geographical sources.

TABLE 9

MICs (µg/ml) against screening panel of bacterial pathogens.

| Cmpd. | S. aureus ATCC 29213 | S. aureus ATCC 13709 | MRSA (tet)M SA161 | S. aureus SA158 (tet)K | E. faecalis ATCC 29212 | E. faecalis EF159 (tet)M | S. pneum ATCC 49619 | S. pneum SP160 (tet)M |
|---|---|---|---|---|---|---|---|---|
| 109 | 0.03 | 0.13 | 32 | 1 | 1 | 32 | 0.03 | 8 |
| 151 | 0.25 | 0.5 | 2 | 0.125 | 0.25 | 2 | 0.016 | 0.125 |
| Tetracycline | 0.5 | 1 | 32 | >32 | 16 | >32 | 0.25 | >32 |
| Doxycycline | 0.5 | 0.13 | 8 | 2 | 4 | 8 | 0.25 | 8 |

| Cmpd. | E. coli ATCC 25922 | E. coli EC155 (tet)A | A. baum AB110 | P. aeruginosa ATCC 27853 | Enterobacter cloaceae ATCC 13047 | Klebsiella pneum ATCC 13883 | S. Klebsiella pneum KP153 (tet)A |
|---|---|---|---|---|---|---|---|
| 109 | 0.13 | >32 | 0.5 | 8 | 1 | 0.5 | >32 |
| 151 | 0.5 | 8 | 2 | 32 | 2 | 2 | 8 |
| Tetracycline | 2 | >32 | 1 | 32 | 2 | 4 | >32 |
| Doxycycline | 1 | 32 | 2 | >32 | 4 | 2 | 32 |

TABLE 10

$MIC_{50}$ and $MIC_{90}$ analysis (µg/ml)

| Cmpd. | S. aureus (n = 20) MIC range | $MIC_{50}$ | $MIC_{90}$ | S. pneumoniae (n = 20) MIC range | $MIC_{50}$ | $MIC_{90}$ | H. influenzae (n = 12) MIC range | $MIC_{50}$ | $MIC_{90}$ |
|---|---|---|---|---|---|---|---|---|---|
| 109 | ≤0.016-1 | ≤0.016 | ≤0.016 | ≤0.016-8 | 2 | 4 | 0.063-4 | 0.5 | 2 |
| 151 | 0.063-0.5 | 0.13 | 0.25 | ≤0.016-0.063 | ≤0.016 | 0.063 | 0.25-2 | 1 | 1 |
| Tetracycline | 0.06-32 | 0.13 | 0.25 | 0.13->32 | >32 | >32 | 0.25-16 | 0.5 | 16 |
| Doxycycline | ND | ND | ND | ≤0.016-16 | 8 | 8 | 0.5-4 | 1 | 4 |
| Oxacillin/Amoxicillin | 0.06-64 | 8 | 64 | ≤0.016-8 | 8 | 8 | 2-32 | 4 | 16 |

Pharmacokinetic Analysis of Compound 109 and Compound 151

The pharmacokinetic properties of Compound 109 and Compound 151 were determined in Sprague-Dawley rats (n=5 and 3, respectively) after a single dose of 1 mg/kg or IV/10 mg/kg PO using PHARSIGHT® WinNonlin, version 5.2 modeling software. The oral bioavailability of tetracycline in rats is 12.1%.

Results:

The following pharmacokinetic parameters for Compound 109 were obtained after IV dosing: AUC 1087 ng*h/mL, Cl 919 mL/h/kg, Vz 4177 mL/kg, and T½ 3 h. The oral bioavailability in the rat was 13%.

TABLE 11

Pharmacokinetics of Compound 109 and Compound 151 in Sprague-Dawley rats.

| Parameter | 151, IV (n = 3) | | 151, PO (n = 3) | | 109, IV (n = 5) | | 109, PO (n = 5) | |
|---|---|---|---|---|---|---|---|---|
| | Mean | SD | Mean | SD | Mean | SD | Mean | SD |
| Half-life (hr) | 4.30 | 0.10 | 5.21 | 0.42 | 3.14 | 0.51 | 4.51 | 2.59 |
| Tmax (hr) | 0.22 | 0.24 | 0.83 | 0.29 | 0.08 | 0.00 | 1.40 | 0.55 |
| $Cl_{obs}$ (mL/hr/kg) | 202.34 | 14.07 | — | — | 918.65 | 68.61 | — | — |
| $Vz_{obs}$ (mL/kg) | 1256.14 | 102.39 | — | — | 4176.97 | 861.89 | — | — |
| $AUC_{last}$ (hr · ng/mL) | 4872.33 | 359.13 | 394.91 | 92.72 | 1086.51 | 86.55 | 1247.57 | 206.78 |
| Cmax (ng/mL) | 2404.67 | 1534.79 | 69.77 | 4.88 | 602.80 | 286.03 | 192.20 | 32.22 |
| % F. | | | 0.80% | | | | 12.74% | |

Mouse Systemic Infection Models

Compounds were screened for antibacterial activity in vivo in a mouse systemic infection (septicemia) model. In the model, CD-1 female mice (18-20 grams) were injected IP with a inoculum that results in 0% survival within 24 to 48 hours. The bacterial dose required to achieve this effect was previously been established through virulence studies. At one hour post infection, mice received either 3 mg/ml IV or 30 mg/ml PO. Typically, six mice were treated per dose group. Animal survival was assessed and recorded for 48 hours. Percent survival at 48 hours was recorded for each compound.

a.) S. aureus Septicemia Model

S. aureus ATCC 13709 (Smith) was mixed with 5% mucin and inoculated by intraperitoneal injection at $2.1 \times 10^6$/mouse. One hour post-challenge, mice received intravenous treatment with either compound 109, compound 151, tetracycline or tigecycline at concentrations ranging from 0.05-10 mg/kg. The $PD_{50}$ in mg/kg was calculated as survival after 48 hours.

b.) E. coli Septicemia Model

E. coli ATCC 25922 at was mixed with 5% mucin and inoculated by intraperitoneal injection at $2.0 \times 10^7$ cfu/mouse. One hour post-challenge, mice received treatment with compound 109, compound 151, tetracycline or tigecycline in concentrations ranging from 30 to 0.3 mg/kg. Survival was assessed after 48 hours and $PD_{50}$ values were calculated.

Results

The $PD_{50}$ of Compound 109 and Compound 151 in the mouse septicemia model was <0.3 and 0.36 mg/kg against S. aureus and 4.3 and 17.0 mg/kg against E. coli, respectively.

TABLE 12

| | S. aureus ATCC 13709 | | | E. coli ATCC 25922 | | |
|---|---|---|---|---|---|---|
| Compound | MIC (µg/ml) | $PD_{50}$ (mg/kg) | 95% C.I. | MIC (µg/ml) | $PD_{50}$ (mg/kg) | 95% C.I. |
| 109 | 0.25 | <0.30 | — | 0.13 | 4.3 | 4.1-4.6 |
| 151 | 0.5 | 0.36 | 0.36-0.56 | 0.25 | 17.0 | 4.1-30 |
| Tetracycline | 0.5 | 0.35 | 0.34 -0.37 | 1 | 17.0 | 7.3-26.8 |
| Tigecycline | 0.13 | 0.35 | 0.24-0.47 | 0.13 | 2.1 | 1.8-2.4 |

While this invention has been particularly shown and described with references to example embodiments thereof, it will be understood by those skilled in the art that various changes in form and details may be made therein without departing from the scope of the invention encompassed by the appended claims.

What is claimed is:

1. A method of therapeutically treating a bacterial infection in a subject comprising administering to the subject an effective amount of a compound of Formula I:

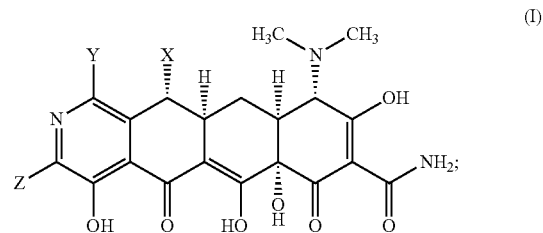

or a pharmaceutically acceptable salt thereof, wherein:

X is selected from hydrogen, $C_1$-$C_6$ alkyl, phenyl and $C_1$-$C_6$ alkoxy, wherein each $C_1$-$C_6$ alkyl and $C_1$-$C_6$ alkoxy represented by X is optionally substituted with halo, unsubstituted $C_1$-$C_6$ alkyl, halo($C_1$-$C_6$)alkyl, unsubstituted $C_1$-$C_6$ alkoxy or halo($C_1$-$C_6$)alkoxy;

Y is selected from hydrogen, fluoro, chloro, $C_1$-$C_6$ alkyl, $C_1$-$C_6$ alkoxy, ($C_0$-$C_6$) alkylene-N($R^1$)($R^2$) and phenyl, wherein each $C_1$-$C_6$ alkyl, $C_0$-$C_6$ alkylene and $C_1$-$C_6$ alkoxy represented by Y is optionally substituted with halo, unsubstituted $C_1$-$C_6$ alkyl, halo($C_1$-$C_6$)alkyl, unsubstituted $C_1$-$C_6$ alkoxy or halo($C_1$-$C_6$)alkoxy;

each of $R^1$ and $R^2$ is independently selected from hydrogen, and $C_1$-$C_6$ alkyl; and Z is selected from hydrogen, halo, $C_1$-$C_6$ alkyl, phenyl, —N($R^3$)($R^4$), ($C_1$-$C_6$) alkylene-N($R^5$)($R^6$), wherein $R^3$ is selected from hydrogen, $C_1$-$C_6$ alkyl, —($C_1$-$C_6$ alkylene)-phenyl, phenyl, —($C_1$-$C_6$ alkylene)-($C_3$-$C_7$ cycloalkyl), —(C$_1$-C$_6$ alkylene)-O—(C$_1$-C$_6$ alkyl), —(C$_1$-C$_6$ alkylene)-N(R$^5$)(R$^6$), —C(O)—(C$_0$-C$_6$ alkylene)-N(R$^5$)(R$^6$), —C(O)—(C$_1$-C$_6$ alkyl), —C(O)H, —C(O)-phenyl, and —S(O)$_2$—R$^5$;

R$^4$ is selected from hydrogen, C$_1$-C$_6$ alkyl; or

R$^3$ and R$^4$ are taken together with the nitrogen atom to which they are bound to form a (4-7 membered) heterocyclic ring optionally containing one additional heteroatom selected from S, O or N; and R$^5$ is selected from hydrogen, C$_1$-C$_6$ alkyl, and phenyl;

R$^6$ is selected from hydrogen and C$_1$-C$_6$ alkyl; or

R$^5$ and R$^6$ are taken together with the nitrogen atom to which they are bound to form a (4-7 membered) heterocyclic ring optionally containing one additional heteroatom selected from S, O or N, wherein each (C$_1$-C$_6$) alkyl, (C$_1$-C$_6$) alkylene or a (4-7 membered) heterocyclic ring in the group represented by Z is optionally substituted with fluoro, —OH, or —CH$_3$; and wherein each phenyl in the group represented by X, Y, Z, R$^3$ and R$^5$ is optionally substituted with halo, unsubstituted C$_1$-C$_6$ alkyl, halo(C$_1$-C$_6$) alkyl, unsubstituted C$_1$-C$_6$ alkoxy, halo(C$_1$-C$_6$) alkoxy, cyano or nitro, wherein Y and Z are not simultaneously hydrogen.

2. The method of claim 1, wherein the compound is of Formula II:

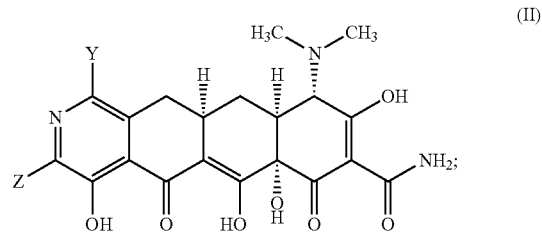

or a pharmaceutically acceptable salt thereof.

3. The method of claim 1, wherein Z is selected from hydrogen, C$_1$-C$_6$ alkyl, phenyl and N(R$^3$)(R$^4$), wherein the phenyl in the group represented by Z is optionally substituted with halo, unsubstituted C$_1$-C$_6$ alkyl, halo(C$_1$-C$_6$)alkyl, unsubstituted C$_1$-C$_6$ alkoxy, halo(C$_1$-C$_6$)alkoxy, cyano or nitro.

4. The method of claim 1, wherein Y is selected from hydrogen, chloro, fluoro, —N(CH$_3$)(CH$_3$), —OCH$_3$, the phenyl and (C$_1$-C$_6$)alkyl, wherein phenyl in the group represented by Y is optionally substituted with halo, unsubstituted C$_1$-C$_6$ alkyl, halo(C$_1$-C$_6$)alkyl, unsubstituted C$_1$-C$_6$ alkoxy, halo(C$_1$-C$_6$)alkoxy, cyano or nitro.

5. The method of claim 4, wherein:

Z is selected from hydrogen, —NH$_2$, —NH(CH$_2$)$_2$CH$_3$, —NH(CH$_2$)$_2$OCH$_3$, —NHCH$_2$CF$_3$, and —NHCH$_2$C(CH$_3$)$_2$CH$_2$N(CH$_3$)CH$_3$.

6. The method of claim 5 wherein:

Y is selected from hydrogen, chloro, fluoro, and —N(CH$_3$)(CH$_3$).

7. The method of claim 1, wherein for the compound of Formula I, X, Y and Z are as defined in the table below:

| Compound # | X | Y | Z |
|---|---|---|---|
| 100 | H— | F— | H$_3$C—N(CH$_3$)—CH$_2$—C(O)—NH— |
| 101 | H— | Cl— | H$_3$C—NH— |
| 103 | H— | Cl— | H$_3$C— |
| 104 | H— | Cl— | H$_3$C—CH$_2$—CH— |
| 105 | H— | (H$_3$C)$_2$C(CH$_3$)—CH$_2$—N— | H— |

-continued

| Compound # | X | Y | Z |
|---|---|---|---|
| 106 | H— | F— | N-methylpiperazinyl |
| 107 | H— | Cl— | (R)-1-phenylethylamino |
| 108 | H— | Cl— | 3-(pyrrolidin-1-yl)-2,2-dimethylpropylamino |
| 109 | H— | (H₃C)₂N— | H— |
| 110 | H— | Cl— | ethylamino |
| 112 | H— | Cl— | isobutylamino |
| 114 | H— | F— | propylamino |
| 115 | H— | Cl— | neopentylamino |
| 116 | H— | H— | isobutylamino |
| 117 | H— | Cl— | 2-hydroxyethyl |
| 118 | H— | (H₃C)₂N— | propylamino |
| 119 | H— | Cl— | 3-(dimethylamino)propylamino |

-continued
| Compound # | X | Y | Z |
|---|---|---|---|
| 120 | H— | F— |  |
| 121 | H— | H₃CO— | H— |
| 122 | H— | H— |  |
| 123 | H— | Cl— | H— |
| 124 | H— | Cl— | 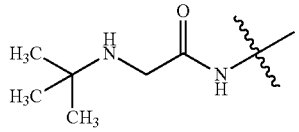 |
| 125 | H— | F— | H₂N— |
| 126 | H— | Cl— |  |
| 127 | H— | H— | 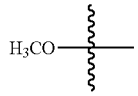 |
| 128 | H— | H— |  |
| 129 | H— | Cl— |  |
| 130 | H— | H— |  |
| 131 | H— | Cl— | 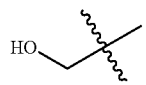 |

-continued

| Compound # | X | Y | Z |
|---|---|---|---|
| 132 | H– | Cl– | H3C–C(CH3)(CH3)–NH–CH2–C(=O)–NH–⁎ |
| 133 | H– | F– | (H3C)2N–CH2–C(CH3)2–CH2–NH–⁎ |
| 134 | H– | Cl– | H3C–CH(CH3)–NH–CH2CH2CH2–NH–⁎ |
| 135 | H– | H– | (H3C)3C–NH–CH2–C(CH3)2–CH2–NH–⁎ |
| 136 | H– | Cl– | C6H5–⁎ |
| 137 | H– | H– | (H3C)3C–CH2–NH–⁎ |
| 138 | H– | F– | Br– |
| 139 | H– | Cl– | C6H5–NH–⁎ |
| 140 | H– | Cl– | (H3C)2N–CH2CH2–NH–⁎ |
| 141 | H– | (H3C)2N– | H3C–CH2–CH(CH3)–⁎ |
| 142 | H– | (H3C)2N– | H3C–NH–C(=O)–NH–⁎ |
| 143 | H– | Cl– | H3C–NH–C(=O)–NH–⁎ |

-continued

| Compound # | X | Y | Z |
|---|---|---|---|
| 144 | H- | F- | H- |
| 145 | H- | (H₃C)₂N- | (H₃C)₂N-CH₂CH₂CH₂- (N,N-dimethyl with CH₃ branch) |
| 146 | H- | H- | H₂N- |
| 147 | H- | Cl- | H₂N- |
| 148 | H- | Cl- | (H₃C)₃C-CH₂CH₂-NH- |
| 149 | H- | (H₃C)₂N- | (H₃C)₃C-NH-CH₂-C(=O)-NH- |
| 150 | H- | Cl- | H₃C-O-CH₂CH₂-NH- |
| 151 | H- | Cl- | (H₃C)₂N-CH₂-C(CH₃)₂-CH₂-NH- |
| 152 | H- | H₃C- | H- |
| 153 | H- | Cl- | (H₃C)₂CH-O-CH₂CH₂-NH- |
| 154 | H- | Cl- | H₃C-CH₂CH₂CH₂-NH- |
| 155 | H- | (H₃C)₂CH-CH₂-NH- | H- |
| 156 | H- | Cl- | H₃C-CH₂-NH- |

| Compound # | X | Y | Z |
|---|---|---|---|
| 157 | H— | Cl— | isopropylamino (CH(CH₃)₂-NH-) |
| 158 | H— | H— | H₃C— |
| 159 | H— | H— | (CH₃)₂N— |
| 160 | H— | phenyl | H— |
| 161 | H— | H— | H₃C-NH-CH₂- |
| 162 | H— | Cl— | cyclopropylmethyl-NH-CH₂- |
| 163 | H— | F— | pyrrolidin-1-yl-CH₂-C(O)-NH-CH₂- |
| 164 | H— | H— | azetidin-1-yl-CH₂- |
| 165 | H— | H— | benzyl | or a pharmaceutically acceptable salt of any of the foregoing.

8. The method of claim 7 wherein the compound is selected from any one of Compound 101, 109, 110, 124, 125, 144, 146, 147, 150, 151, and 156, or a pharmaceutically acceptable salt thereof.

9. The method of claim 1 or claim 7, wherein the infection is caused by a Gram-positive organism.

10. The method of claim 1 or claim 7, wherein the infection is caused by a Gram-negative organism.

11. The method of claim 1 or claim 7, wherein the infection is caused by an organism selected from the group consisting of rickettsiae, chlamydiae, and *Mycoplasma pneumoniae*.

12. The method of claim 1 or claim 7, wherein the infection is caused by an organism resistant to tetracycline.

13. The method of claim 1 or claim 7, wherein the infection is caused by an organism resistant to methicillin.

14. The method of claim 1 or claim 7, wherein the infection is caused by an organism resistant to vancomycin.

* * * * *